US009514358B2

(12) United States Patent
Konofagou et al.

(10) Patent No.: US 9,514,358 B2
(45) Date of Patent: *Dec. 6, 2016

(54) SYSTEMS AND METHODS FOR MATCHING AND IMAGING TISSUE CHARACTERISTICS

(71) Applicant: The Trustees of Columbia University in the City of New York, New York, NY (US)

(72) Inventors: Elisa Konofagou, New York, NY (US); Jean Provost, New York, NY (US)

(73) Assignee: THE TRUSTEES OF COLUMBIA UNIVERSITY IN THE CITY OF NEW YORK, New York, NY (US)

( * ) Notice: Subject to any disclaimer, the term of this patent is extended or adjusted under 35 U.S.C. 154(b) by 542 days.

This patent is subject to a terminal disclaimer.

(21) Appl. No.: 13/848,436

(22) Filed: Mar. 21, 2013

(65) Prior Publication Data

US 2013/0315491 A1 Nov. 28, 2013

Related U.S. Application Data

(63) Continuation of application No. 13/019,029, filed on Feb. 1, 2011, now Pat. No. 8,428,687, which is a
(Continued)

(51) Int. Cl.
*A61B 8/00* (2006.01)
*G06K 9/00* (2006.01)
(Continued)

(52) U.S. Cl.
CPC ............ *G06K 9/00536* (2013.01); *A61B 8/08* (2013.01); *A61B 8/485* (2013.01); *G01S 7/52042* (2013.01);
(Continued)

(58) Field of Classification Search
CPC .................................. A61B 8/08; A61B 8/485
See application file for complete search history.

(56) References Cited

U.S. PATENT DOCUMENTS 3,598,111 A   8/1971 Kahn
4,463,608 A   8/1984 Takeuchi et al.
(Continued)

FOREIGN PATENT DOCUMENTS

EP   0 221 409   5/1987
EP   0 627 206   12/1994
(Continued)

OTHER PUBLICATIONS

U.S. Appl. No. 12/077,612, Sep. 22, 2014 Amendment and Request for Continued Examination (RCE).
(Continued)

*Primary Examiner* — Rajeev Siripurapu
(74) *Attorney, Agent, or Firm* — Baker Botts L.L.P.

(57) ABSTRACT

Systems and methods for matching a characteristic of multiple sectors of a moving tissue to verify an overlap thereof are disclosed herein. In an exemplary method, tissue data for at least a first sector and a second sector of a moving tissue is acquired. A characteristic of at least a portion of the first and second sectors is estimated from the acquired tissue data, and the estimated characteristics are matched to verify whether a portion of the first sector overlaps with a portion of the second sector. Estimating can include estimating a displacement such as an axial displacement and/or lateral displacements. Estimating can further include estimating a strain, a velocity, a strain rate and/or a stiffness or equivalent.

16 Claims, 69 Drawing Sheets

Related U.S. Application Data continuation-in-part of application No. PCT/US2009/052563, filed on Aug. 3, 2009.

(60) Provisional application No. 61/085,709, filed on Aug. 1, 2008, provisional application No. 61/086,112, filed on Aug. 4, 2008, provisional application No. 61/108,470, filed on Oct. 24, 2008.

(51) Int. Cl.
*A61B 8/08* (2006.01)
*G01S 7/52* (2006.01)
*A61B 5/055* (2006.01)
*A61B 6/03* (2006.01)
*A61B 6/00* (2006.01)
*G01S 15/89* (2006.01)

(52) U.S. Cl.
CPC ............ *G01S 7/52071* (2013.01); *A61B 5/055* (2013.01); *A61B 6/03* (2013.01); *A61B 6/503* (2013.01); *A61B 6/504* (2013.01); *A61B 8/0891* (2013.01); *G01S 15/8977* (2013.01)

(56) References Cited

U.S. PATENT DOCUMENTS

| | | |
|---|---|---|
| 4,777,599 A | 10/1988 | Dorogi et al. |
| 4,832,941 A | 5/1989 | Berwing et al. |
| 4,858,613 A | 8/1989 | Fry et al. |
| 4,882,679 A | 11/1989 | Tuy et al. |
| 5,038,787 A | 8/1991 | Antich et al. |
| 5,107,837 A | 4/1992 | Ophir et al. |
| 5,178,147 A | 1/1993 | Ophir et al. |
| 5,309,914 A | 5/1994 | Iinuma |
| 5,433,708 A | 7/1995 | Nichols et al. |
| 5,435,310 A | 7/1995 | Sheehan et al. |
| 5,457,754 A | 10/1995 | Han et al. |
| 5,601,084 A | 2/1997 | Sheehan et al. |
| 5,606,971 A | 3/1997 | Sarvazyan |
| 5,662,113 A | 9/1997 | Liu |
| 5,722,411 A | 3/1998 | Suzuki et al. |
| 5,741,522 A | 4/1998 | Violante et al. |
| 5,752,515 A | 5/1998 | Jolesz et al. |
| 5,769,790 A | 6/1998 | Watkins et al. |
| 5,810,731 A | 9/1998 | Sarvazyan et al. |
| 5,840,028 A | 11/1998 | Chubachi et al. |
| 5,928,151 A | 7/1999 | Hossack et al. |
| 6,026,173 A | 2/2000 | Svenson et al. |
| 6,028,066 A | 2/2000 | Unger |
| 6,102,864 A | 8/2000 | Hatfield et al. |
| 6,102,865 A | 8/2000 | Hossack et al. |
| 6,106,465 A | 8/2000 | Napolitano et al. |
| 6,123,669 A | 9/2000 | Kanda et al. |
| 6,152,878 A | 11/2000 | Nachtomy et al. |
| 6,193,951 B1 | 2/2001 | Ottoboni et al. |
| 6,200,266 B1 | 3/2001 | Shokrollahi et al. |
| 6,241,675 B1 | 6/2001 | Smith et al. |
| 6,246,895 B1 | 6/2001 | Plewes |
| 6,259,943 B1 | 7/2001 | Cosman et al. |
| 6,270,459 B1 | 8/2001 | Konofagou et al. |
| 6,309,355 B1 | 10/2001 | Cain et al. |
| 6,312,382 B1 | 11/2001 | Mucci et al. |
| 6,352,507 B1 | 3/2002 | Torp et al. |
| 6,413,216 B1 | 7/2002 | Cain et al. |
| 6,425,867 B1 | 7/2002 | Vaezy et al. |
| 6,447,450 B1 | 9/2002 | Olstad |
| 6,488,629 B1 | 12/2002 | Saetre et al. |
| 6,491,636 B2 | 12/2002 | Chenal et al. |
| 6,508,768 B1 | 1/2003 | Hall et al. |
| 6,529,770 B1 | 3/2003 | Grimblatov |
| 6,537,217 B1 | 3/2003 | Bjœrum et al. |
| 6,537,221 B2 | 3/2003 | Criton et al. |
| 6,671,541 B2 | 12/2003 | Bishop et al. |
| 6,683,454 B2 | 1/2004 | Rehwald et al. |
| 6,685,641 B2 | 2/2004 | Liu et al. |
| 6,689,060 B2 | 2/2004 | Phelps et al. |
| 6,701,341 B1 | 3/2004 | Wu |
| 6,770,033 B1 | 8/2004 | Fink et al. |
| 6,875,176 B2 | 4/2005 | Mourad et al. |
| 6,936,151 B1 | 8/2005 | Lock et al. |
| 6,994,673 B2 | 2/2006 | Lysyansky et al. |
| 7,016,719 B2 | 3/2006 | Rudy et al. |
| 7,055,378 B2 | 6/2006 | Su et al. |
| 7,136,518 B2 | 11/2006 | Griffin et al. |
| 7,257,244 B2 | 8/2007 | Miga |
| 7,331,926 B2 | 2/2008 | Varghese et al. |
| 7,344,509 B2 | 3/2008 | Hynynen et al. |
| 7,421,101 B2 | 9/2008 | Georgescu et al. |
| 7,429,249 B1 | 9/2008 | Winder et al. |
| 7,449,306 B2 | 11/2008 | Elson et al. |
| 7,601,122 B2 | 10/2009 | Zagzebski et al. |
| 7,753,847 B2 | 7/2010 | Greenleaf et al. |
| 7,809,426 B2 | 10/2010 | Kim et al. |
| 7,896,821 B1 | 3/2011 | Magnin et al. |
| 8,029,444 B2 | 10/2011 | Pedrizzetti et al. |
| 8,150,128 B2 | 4/2012 | Konofagou et al. |
| 8,208,709 B2 | 6/2012 | Ding et al. |
| 9,063,220 B2 | 6/2015 | Yoda et al. |
| 2002/0034757 A1 | 3/2002 | Cubicciotti |
| 2002/0038086 A1 | 3/2002 | Hynynen et al. |
| 2002/0039594 A1 | 4/2002 | Unger |
| 2002/0065461 A1 | 5/2002 | Cosman |
| 2002/0095081 A1 | 7/2002 | Vilsmeier |
| 2002/0151792 A1 | 10/2002 | Conston et al. |
| 2002/0169394 A1 | 11/2002 | Eppstein et al. |
| 2002/0193784 A1 | 12/2002 | McHale et al. |
| 2003/0097068 A1 | 5/2003 | Hossack et al. |
| 2003/0125621 A1 | 7/2003 | Drukker et al. |
| 2003/0171672 A1 | 9/2003 | Varghese et al. |
| 2003/0174890 A1 | 9/2003 | Yamauchi |
| 2003/0220556 A1 | 11/2003 | Porat et al. |
| 2004/0006266 A1 | 1/2004 | Ustuner et al. |
| 2004/0049134 A1 | 3/2004 | Tosaya et al. |
| 2004/0054357 A1 | 3/2004 | O'Donnell |
| 2004/0059224 A1 | 3/2004 | Varghese et al. |
| 2004/0092816 A1 | 5/2004 | Ossmann et al. |
| 2004/0097805 A1 | 5/2004 | Verard et al. |
| 2004/0172081 A1 | 9/2004 | Wang |
| 2004/0210134 A1 | 10/2004 | Hynynen et al. |
| 2004/0210135 A1 | 10/2004 | Hynynen |
| 2004/0234113 A1 | 11/2004 | Miga |
| 2004/0236219 A1 | 11/2004 | Liu et al. |
| 2004/0249580 A1 | 12/2004 | Pourcelot et al. |
| 2004/0258760 A1 | 12/2004 | Wheatley et al. |
| 2005/0004466 A1 | 1/2005 | Hynynen et al. |
| 2005/0026262 A1 | 2/2005 | Yoshitani et al. |
| 2005/0054930 A1 | 3/2005 | Rickets et al. |
| 2005/0059876 A1 | 3/2005 | Krishnan |
| 2005/0080336 A1 | 4/2005 | Byrd et al. |
| 2005/0080469 A1 | 4/2005 | Larson et al. |
| 2005/0084538 A1 | 4/2005 | Dayton et al. |
| 2005/0124892 A1* | 6/2005 | Weitzel ............... A61B 8/485 600/449 |
| 2005/0175541 A1 | 8/2005 | Lanza et al. |
| 2005/0201942 A1 | 9/2005 | Dugstad et al. |
| 2005/0203395 A1 | 9/2005 | Sui et al. |
| 2005/0203399 A1 | 9/2005 | Vaezy et al. |
| 2005/0259864 A1 | 11/2005 | Dickinson et al. |
| 2005/0267695 A1 | 12/2005 | German |
| 2005/0277824 A1 | 12/2005 | Aubry et al. |
| 2005/0277835 A1 | 12/2005 | Angelsen et al. |
| 2006/0034904 A1 | 2/2006 | Weimann |
| 2006/0058651 A1 | 3/2006 | Chiao et al. |
| 2006/0058671 A1 | 3/2006 | Vitek et al. |
| 2006/0058673 A1 | 3/2006 | Aase et al. |
| 2006/0074315 A1 | 4/2006 | Liang et al. |
| 2006/0078501 A1 | 4/2006 | Goertz et al. |
| 2006/0173320 A1 | 8/2006 | Radulescu |
| 2006/0241529 A1 | 10/2006 | Hynynen et al. |
| 2007/0049824 A1 | 3/2007 | Konofagou et al. |
| 2007/0055179 A1 | 3/2007 | Deem et al. |
| 2007/0071683 A1 | 3/2007 | Dayton et al. |
| 2007/0207194 A1 | 9/2007 | Grayburn et al. |

(56) References Cited

U.S. PATENT DOCUMENTS

| | | |
|---|---|---|
| 2007/0219447 A1 | 9/2007 | Kanai et al. |
| 2007/0232962 A1 | 10/2007 | Zumeris et al. |
| 2007/0239001 A1 | 10/2007 | Mehi et al. |
| 2007/0276242 A1 | 11/2007 | Konofagou et al. |
| 2007/0276245 A1 | 11/2007 | Konofagou et al. |
| 2008/0194957 A1 | 8/2008 | Hoctor et al. |
| 2008/0200417 A1 | 8/2008 | Semple et al. |
| 2008/0243214 A1 | 10/2008 | Koblish |
| 2008/0260802 A1 | 10/2008 | Sawhney et al. |
| 2008/0269606 A1 | 10/2008 | Matsumura |
| 2008/0269668 A1 | 10/2008 | Keenan et al. |
| 2008/0285819 A1 | 11/2008 | Konofagou et al. |
| 2008/0319375 A1 | 12/2008 | Hardy |
| 2009/0005711 A1 | 1/2009 | Konofagou et al. |
| 2009/0191244 A1 | 7/2009 | Kheir et al. |
| 2009/0221916 A1 | 9/2009 | Konofagou et al. |
| 2009/0247911 A1 | 10/2009 | Novak et al. |
| 2009/0270790 A1 | 10/2009 | Raghavan |
| 2010/0049036 A1 | 2/2010 | Kimh |
| 2010/0286527 A1 | 11/2010 | Cannon et al. |
| 2011/0098562 A1 | 4/2011 | Salgo et al. |
| 2011/0177005 A1 | 7/2011 | Rapoport et al. |
| 2011/0208038 A1 | 8/2011 | Konofagou et al. |
| 2011/0295105 A1 | 12/2011 | Konofagou et al. |
| 2011/0313328 A1 | 12/2011 | Nita |
| 2012/0004693 A1 | 1/2012 | Lo et al. |
| 2013/0038479 A1 | 2/2013 | Eldar et al. |
| 2013/0195313 A1 | 8/2013 | Gauthier et al. |
| 2013/0289398 A1 | 10/2013 | Borden et al. |
| 2013/0304407 A1 | 11/2013 | George et al. |
| 2014/0114216 A1 | 4/2014 | Konofagou et al. |
| 2015/0045724 A1 | 2/2015 | Chen et al. |
| 2015/0065871 A1 | 3/2015 | Konofagou et al. |
| 2016/0074678 A1 | 3/2016 | Konofagou et al. |

FOREIGN PATENT DOCUMENTS

| | | |
|---|---|---|
| WO | WO 99/37938 | 8/1999 |
| WO | WO 2007/0148279 | 12/2007 |
| WO | WO 2008/015012 | 2/2008 |
| WO | WO 2008/027520 | 3/2008 |
| WO | WO 2008/062342 | 5/2008 |
| WO | WO 2008/131217 | 10/2008 |
| WO | WO 2008/131302 | 10/2008 |
| WO | WO 2008/157422 | 12/2008 |
| WO | WO 2010/044385 | 4/2010 |
| WO | WO 2010/063951 | 6/2010 |
| WO | WO 2011/028690 | 3/2011 |
| WO | WO 2011/035312 | 3/2011 |

OTHER PUBLICATIONS

U.S. Appl. No. 12/096,254, Sep. 22, 2014 Amendment and Request for Continued Examination (RCE).
U.S. Appl. No. 13/529,239, Sep. 3, 2014 Non-Final Office Action.
European Search Report for EP Application No. 10838238, dated May 6, 2014.
International Search Report and Written Opinion for PCT/US2011/034704, dated Aug. 18, 2011.
Borden et al., "Ultrasound Radiation Force Modulates Ligand Availability on Target Contrast Agents", Mol. Imaging, 5:139-147 (2006).
"Vial", Retrieved from http://en.wikipedia.org/w/index.php?title=Vial&oldid=603936258 [Downloaded on May 20, 2014].
U.S. Appl. No. 14/091,010, filed Nov. 26, 213.
U.S. Appl. No. 11/697,573, Oct. 17, 2013 Final Office Action.
U.S. Appl. No. 13/353,148, Oct. 17, 2013 Final Office Action.
U.S. Appl. No. 13/045,070, Nov. 7, 2013 Amendment and Request for Continued Examination (RCE).
U.S. Appl. No. 13/529,239, Dec. 31, 2013 Final Office Action.
U.S. Appl. No. 13/529,239, Dec. 3, 2013 Response to Non-Final Office Action.
U.S. Appl. No. 13/529,239, Nov. 18, 2013 Applicant-Initiated Interview Summary.
U.S. Appl. No. 12/096,254, Dec. 23, 2013 Response to Non-Final Office Action.
U.S. Appl. No. 13/096,254, Dec. 17, 213 Applicant Initiated Interview Summary.
U.S. Appl. No. 12/077,612, Jan. 30, 2014 Response to Non-Final Office Action.
U.S. Appl. No. 12/077,612, Jan. 2, 2014 Applicant Initiated Interview Summary.
Ginat, et al., "High-Resolution Ultrasound Elastography of Articular Cartilage in Vitro", *Proceedings of the 28th IEEE EMBS Annual International Conference*, New York City, USA, pp. 6644-6647 (Aug. 30-Sep. 3, 2006).
U.S. Appl. No. 13/353,148, filed Jan. 18, 2012.
U.S. Appl. No. 13/529,239, filed Jun. 21, 2012.
U.S. Appl. No. 13/426,400, filed Mar. 21, 2012.
U.S. Appl. No. 11/697,573, May 10, 2013 Non-Final Office Action.
U.S. Appl. No. 11/697,573, Jan. 18, 2013 Amendment and Request for Continued Examination (RCE).
U.S. Appl. No. 11/697,573, Jul. 18, 2012 Final Office Action.
U.S. Appl. No. 11/697,573, Jun. 27, 2012 Response to Non-Final Office Action.
U.S. Appl. No. 11/697,573, Jan. 26, 2012 Non-Final Office Action.
U.S. Appl. No. 11/697,573, Aug. 18, 2011 Amendment and Request for Continued Examination (RCE).
U.S. Appl. No. 11/697,573, Mar. 18, 2011 Final Office Action.
U.S. Appl. No. 11/697,573, Dec. 22, 2010 Response to Non-Final Office Action.
U.S. Appl. No. 11/697,573, Jun. 23, 2010 Non-Final Office Action.
U.S. Appl. No. 12/077,612, Oct. 26, 2011 Amendment and Request for Continued Examination (RCE).
U.S. Appl. No. 12/077,612, May 26, 2011 Final Office Action.
U.S. Appl. No. 12/077,612, Mar. 23, 2011 Response to Non-Final Office Action.
U.S. Appl. No. 12/077,612, Nov. 16, 2010 Non-Final Office Action.
U.S. Appl. No. 12/096,254, Nov. 30, 2012 Amendment and Request for Continued Examination (RCE).
U.S. Appl. No. 12/096,254, May 31, 2012 Final Office Action.
U.S. Appl. No. 12/096,254, Apr. 4, 2012 Response to Non-Final Office Action.
U.S. Appl. No. 12/096,254, Oct. 5, 2011 Non-Final Office Action.
U.S. Appl. No. 13/019,029, Dec. 26, 2012 Notice of Allowance.
U.S. Appl. No. 13/045,070, May 9, 2013 Final Office Action.
U.S. Appl. No. 13/045,070, Dec. 21, 2012 Response to Non-Final Office Action.
U.S. Appl. No. 13/045,070, Jun. 22, 2012 Non-Final Office Action.
U.S. Appl. No. 11/697,579, Nov. 28, 2011 Notice of Abandonment.
U.S. Appl. No. 11/697,579, Apr. 29, 2011 Final Office Action.
U.S. Appl. No. 11/697,579, Feb. 7, 2011 Response to Non-Final Office Action.
U.S. Appl. No. 11/697,579, Aug. 6, 2010 Non-Final Office Action.
U.S. Appl. No. 11/697,579, May 17, 2010 Response to Non-Final Office Action.
U.S. Appl. No. 11/697,579, Nov. 17, 2009 Non-Final Office Action.
U.S. Appl. No. 11/697,579, Oct. 15, 2009 Amendment and Request for Continued Examination (RCE).
U.S. Appl. No. 11/697,579, Jul. 15, 2009 Response to Final Office Action.
U.S. Appl. No. 11/697,579, Apr. 15, 2009 Final Office Action.
U.S. Appl. No. 11/697,579, Jan. 16, 2009 Response to Non-Final Office Action.
U.S. Appl. No. 11/697,579, Jul. 18, 2008 Non-Final Office Action.
U.S. Appl. No. 11/899,004, Jan. 3, 2012 Issue Fee payment.
U.S. Appl. No. 11/899,004, Nov. 3, 2011 Decision on Petition.
U.S. Appl. No. 11/899,004, Oct. 4, 2011 Petition and Amendment after Notice of Allowance.
U.S. Appl. No. 11/899,004, Oct. 3, 2011 Notice of Allowance.
U.S. Appl. No. 11/899,004, Sep. 23, 2011 Amendment and Request for Continued Examination (RCE).
U.S. Appl. No. 11/899,004, Sep. 19, 2011 Decision on Petition.
U.S. Appl. No. 11/899,004, Jul. 18, 2011 Notice of Allowance.

(56) References Cited

OTHER PUBLICATIONS

U.S. Appl. No. 11/899,004, May 10, 2011 Response to Non-Final Office Action.
U.S. Appl. No. 11/899,004, Feb. 8, 2011 Non-Final Office Action.
U.S. Appl. No. 11/433,510, Mar. 30, 2012 Request for Continued Examination (RCE).
U.S. Appl. No. 11/433,510, Mar. 28, 2012 Advisory Action.
U.S. Appl. No. 11/433,510, Dec. 29, 2011 Response to Final Office Action.
U.S. Appl. No. 11/433,510, Sep. 30, 2011 Final Office Action.
U.S. Appl. No. 11/433,510, May 23, 2011 Response to Non-Final Office Action.
U.S. Appl. No. 11/433,510, Jan. 21, 2011 Non-Final Office Action.
U.S. Appl. No. 11/433,510, Oct. 28, 2010 Response to Non-Final Office Action.
U.S. Appl. No. 11/433,510, Apr. 28, 2010 Non-Final Office Action.
U.S. Appl. No. 11/433,510, Apr. 13, 2010 Amendment and Request for Continued Examination (RCE).
U.S. Appl. No. 11/433,510, Nov. 12, 2009 Final Office Action.
U.S. Appl. No. 11/433,510, Aug. 6, 2009 Response to Non-Final Office Action.
U.S. Appl. No. 11/433,510, Mar. 17, 2009 Non-Final Office Action.
Abbott, et al., "Astrocyte-Endothelial Interactions at the Blood-Brain Barrier", *Nat. Rev. Neurosci.*, 7(1):41-53 (2006).
Ammi, et al., "Ultrasonic contrast agent shell rupture detected by inertial cavitation and rebound signals", *IEEE Transactions*, 53(1):126-136 (2006).
Ashikaga, et al., "Transmural Dispersion of Myofiber Mechanics: Implications for Electrical Heterogeneity In Vivo", *Journal of the American College of Cardiology*, 49(8):909-916 (2007).
Aubry, et al., "Experimental Demonstration of Noninvasive Transskull Adaptive Focusing Based on Prior Computed Tomography Scans", *The Journal of the Acoustical Society of America*, 113:84 (2003).
Avolio, et al., "Effects of aging on changing arterial compliance and left ventricular load in a northern Chinese urban community", *Circulation*, 68(1):50-58 (1983).
Azuma, et al., "Bubble Generation by Standing Wave in Water Surrounded by Cranium With Transcranial Ultrasonic Beam", *Japanese Journal of Applied Physics*, 44:4625-4630 (2005).
Badke, et al., "Effects of Ventricular Pacing on Regional Left Ventricular Performance in the Dog", *Am J Physiol Heart Circ Physiol.*, 238:H858-867 (1980).
Baron, et al., "Simulation of Intracranial Acoustic Fields in Clinical Trials of Sonothrombolysis", *Ultrasound Med. Biol.*, 35(7):1148-1158 (2009).
Baseri, et al., "Multi-Modality Safety Assessment of Blood-Brain Barrier Opening Using Focused Ultrasound and Definity Microbubbles: A Short-Term Study", *Ultrasound Med. Biol.*, 6(9):1445-1459 (2010).
Behrens, et al., "Low-Frequency, Low-Intensity Ultrasound Accelerates Thrombolysis Through the Skull", *Ultrasound in Medicine & Biology*, 25:269-273 (1999).
Bercoff, et al., "Supersonic Shear Imaging: A New Technique for Soft Tissue Elasticity Mapping", *IEEE Transactions on Ultrasonics Ferroelectrics and Frequency Control*, 51:396-409 (2004).
Berger, et al., "Single-Beat Noninvasive Imaging of Cardiac Electrophysiology of Ventricular Pre-Excitation", *Journal of the American College of Cardiology*, 48:2045-2052 (2006).
Bers, "Cardiac Excitation-Contraction Coupling", *Nature*, 415:198-205 (2002).
Bonnefous, et al, "Time Domain Formulation of Pulse-Doppler Ultrasound and Blood Velocity Estimation by Cross Correlation", *Ultrason Imaging*, 8(2):73-85 (1986).
Brekke, et al., "Tissue Doppler Gated (TDOG) Dynamic Three-Dimensional Ultrasound Imaging of the Fetal Heart", *Ultrasound Obstet Gynecol.*, 24(2):192-198 (2004).
Brooks, et al., "Electrical Imaging of the Heart", *IEEE Signal Processing Magazine*, 14:24-42 (1997).

Brundin, et al., "Restorative Therapies in Parkinson's Disease", *Springer Verlag* (2006).
Campbell, et al., "Mechanisms of Transmurally Varying Myocyte Electromechanics in an Integrated Computational Model", *Philos Transact a Math Phys Eng Sci.*, 366:3361-3380 (2008).
Caskey, et al., "Direct Observations of Ultrasound Microbubble Contrast Agent Interaction With the Microvessel Wall", *J. Acoust. Soc. Amer.*, 122(2):1191-1200 (2007).
Caskey, et al., "Microbubble Oscillation in Tubes With Diameters of 12, 25, and 195 Microns", *Appl. Phys. Lett.*, 88(3):033902-1-033902-3 (2006).
Cavaglia, et al., "Regional Variation in Brain Capillary Density and Vascular Response to Ischemia", *Brain Res.*, 910(1-2):81-93 (2001).
Chan, "Transgenic Nonhuman Primates for Neurodegenerative Diseases", *Reproductive Biology and Endocrinology*, 2:39 (2004).
Chang, et al., "3-D US Frame Positioning Using Speckle Decorrelation and Image Registration", *Ultrasound in Medicine and Biology*, pp. 801-812 (2003).
Chen, et al., "Optimization of Ultrasound Parameters for Cardiac Gene Delivery of Adenoviral or Plasmid Deoxyribonucleic Acid by Ultrasound-Targeted Microbubble Destruction", *J. Amer. Coll. Cardiol.*, 42(2):301-308 (2003).
Chen, et al., "Estimation of Displacement Vectors and Strain Tensors in Elastography Using Angular Insonifications", *IEEE Transactions on Medical Imaging*, 23(12):1479-1489 (2004).
Chen, et al., "Engineering Acoustics and ASA Committee on Standards: Sound Intensity Measurements", *J. Acoust. Soc. Am.; 164th Meeting: Acoustical Society of America*, 132(3, Pt. 2):1984 (Sep. 2012).
Chen, et al., "Architectural Acoustics and Noise: Advancements and Best Practices in Instrumentation for Architectural Acoustics and Noise", *J. Acoust. Soc. Am.; 164th Meeting: Acoustical Society of America*, 132(3, Pt. 2):1977-2018 (Sep. 2012).
Choi, et al., "Feasibility of Transcranial, Localized Drug-Delivery in the Brain of Alzheimer's-Model Mice Using Focused Ultrasound", *2005 IEEE Ultrasonics Symposium*, pp. 988-991 (Sep. 18-21, 2005).
Choi, et al., "Molecules of Various Pharmacologically-Relevant Sizes Can Cross the Ultrasound-Induced Blood-Brain Barrier Opening In Vivo", *Ultrasound in Medicine & Biology*, 36(1):58-67 (2009).
Choi, et al., "Noninvasive, Transcranial and Localized Opening of the Blood-Brain Barrier Using Focused Ultrasound in Mice", *Ultrasound in Medicine & Biology*, 33(1):95-104 (2007).
Choi, et al., "Spatio-Temporal Analysis of Molecular Delivery Through the Blood-Brain Barrier Using Focused Ultrasound", *Physics in Medicine and Biology*, 52:5509-5530, (2007).
Choi, et al., "Focused Ultrasound-Induced Molecular Delivery Through the Blood-Brain Barrier", *Presented at the IEEE Symp. Ultrason. Ferroelect. Freq. Control*, New York, NY, pp. 1192-1195 (2007).
Choi, et al., "Delivery of pharmacologically-relevant sized molecules through the ultrasound-induced blood-brain barrier opening in vivo", *Neuroscience*, Chicago, IL, USA, Oct. 17-21. 2009.
Choi, et al., "Noninvasive and Transient Blood-Brain Barrier Opening in the Hippocampus of Alzheimer's Double Transgenic Mice Using Pulsed Focused Ultrasound", *Ultrasonic Imaging*, pp. 189-200 (2008).
Choi, et al., "Optimization of Blood-Brain Barrier Opening in Mice using Focused Ultrasound", *2006 IEEE Ultrasounics Symposium* [online], Jun. 2007.
Choi, et al., "Microbubble-size dependence of focused ultrasound-induced blood-brain barrier opening in mice in vivo", *IEEE transactions on Biomedical Engineering*, 57(1):145-154 (2010).
Chomas, et al., "Threshold of Fragmentation for Ultrasonic Contrast Agents", *J. Biomed. Opt.*, 6(2):141-150 (2001).
Clement, et al., "A Hemisphere Array for Non-Invasive Ultrasound Brain Therapy and Surgery", *Phys Med Biol.*, 45:3707-3719 (2000).
Cobbold, R.S.C., "Foundations of biomedical ultrasound", Biomedical engineering series, Oxford University Press, pp. 422-423(2006).

(56) References Cited

OTHER PUBLICATIONS

Connor, et al., "A Unified Model for the Speed of Sound in Cranial Bone Based on Genetic Algorithm Optimization", *Physics in Medicine and Biology*, 47:3925-3944 (2002).
Connor, "Simulation Methods and Tissue Property Models for Non-Invasive Transcranial Focused Ultrasound Surgery", *Ph.D. Thesis* (2005).
Cordeiro, et al., "Transmural Heterogeneity of Calcium Activity and Mechanical Function in the Canine Left Ventricle",*Am J Physiol. Heart Circ. Physiol.*, 286:H1471-1479 (2004).
Coyle, "Spatial Features of the Rat Hippocampal Vascular System", *Exp. Neurol.*, 58(3): 549-561 (1978).
Coyle, "Arterial Patterns of the Rat Rhinencephalon and Related Structures", *Exp. Neurol.*, 49(3): 671-690 (1975).
Coyle, "Vascular Patterns of the Rat Hippocampal Formation", *Exp. Neurol.*, 52(3): 447-458 (1976).
Crum, et al., "Bjerknes Forces on Bubbles in a Stationary Sound Field", *The Journal of the Acoustical Society of America*, 57(6): 1363-1370 (1975).
Cutnell, et al., (1998). Physics, Fourth Edition. New York. Table of Contents.
Daffertshofer, et al., "Transcranial Low-Frequency Ultrasound-Mediated Thrombolysis in Brain Ischemia: Increased Risk of Hemorrhage With Combined Ultrasound and Tissue Plasminogen Activator: Results of a Phase II Clinical Trial", *Stroke*, 36:1441-146 (2005).
Damianou, et al., "Dependence of ultrasonic attenuation and absorption in dog soft tissues on temperature and thermal dose", *J Acoust Soc Am*, 102(1):628-634 (1997).
Datta, et al., "Correlation of Cavitation With Ultrasound Enhancement of Thrombolysis", *Ultrasound in Medicine & Biology*, 32(8): 1257-1267 (2006).
Declerck, et al., "Left ventricular motion reconstruction from planar tagged MR images: a comparison", *Phys Med Biol.*, 45(6): 1611-1632 (2000).
De Craene, et al., "Temporal diffeomorphic free-form deformation: Application to motion and strain estimation from 3D echocardiography", *Medical Image Analysis*, 16(2):427-450 (2012).
Deffieux, et al., "Transcranial Focused Ultrasound for Blood-Brain Barrier Opening—Numerical Simulations With In Vitro Validation in Human and Monkey Skulls", *Title page and Table of Contents for the AIUM Annual Convention*, San Diego, CA, (2010).
DeLong, "Primate Models of Movement Disorders of Basal Ganglia Origin", *Trends Neurosci.*, 13(7): 281-285 (1990).
DuBose, et al., "Confusion and Direction in Diagnostic Doppler Sonography", *Journal of Diagnostic Medical Sonography*, 25(3):173-177 (2009).
Duck, "Physical Properties of Tissue: A Comprehensive Reference Book", *Academic Press*, London, UK, 1990.
Duerinckx, et al., "In vivo acoustic attenuation in liver: correlations with blood tests and histology", *Ultrasound Imaging*, 14(5):405-413 (1988).
Durrer, et al., "Total Excitation of the Isolated Human Heart", *Circulation*, 41:899-912 (1970).
Edwards, et al., "Effects of Ischemia on Left-Ventricular Regional Function in the Conscious Dog", *American Journal of Physiology*, 240, H413-H420 (1981).
Erpelding, et al., "Bubble-Based Acoustic Radiation Force Using Chirp Insonation to Reduce Standing Wave Effects", *Ultrasound in Medicine & Biology*, 33(2):263-269 (2007).
Everbach, et al., "Cavitational Mechanisms in Ultrasound-Accelerated Thrombolysis at 1 Mhz", *Ultrasound in Medicine & Biology*, 26(7): 1153-1160 (2000).
Faris, et al., "Novel Technique for Cardiac Electromechanical Mapping With Magnetic Resonance Imaging Tagging and an Epicardial Electrode Sock", *Ann Biomed Eng.*, 31:430-440 (2003).
Farook, et al., "Preparation of Microbubble Suspensions by Co-Axial Electrohydrodynamic Atomization", *Med. Eng. Phys.*, 29(7): 749-754 (2007).

Fenster, et al., "Three-dimensional ultrasound imaging", *Phys Med Biol*, 46(5):R67-R99 (2001).
Feshitan et al., "Microbubble Size Isolation by Differential Centrifugation", *Journal of Colloid and Interface Science*, 329: 316-324 (2009).
Fiske, et al., "Special Focus Section: Gene Therapy for Parkinson's Disease", *Experimental Neurology*, 209:28-29 (2008).
Fry, et al., "A Focused Ultrasound System for Tissue Volume Ablation in Deep Seated Brain Sites", *IEEE 1986 Ultrasonics Symposium*, pp. 1001-1004 (1986).
Fry, "Transkull Transmission of an Intense Focused Ultrasonic Beam", *Ultrasound in Medicine & Biology*, 3, p. 179 (1977).
Fujii, et al., "A new method for attenuation coefficient measurement in the liver", *Journal of Ultrasound Medicine*, 21(7):783-788 (2002).
Fung, (1993). Biomechanics—Mechanical Properties of Living Tissues. New York. Table of Contents.
Ganan-Calvo, et al., "Perfectly Monodisperse Microbubbling by Capillary Flow Focusing", *Phys. Rev. Lett.*, 87(27) Pt 1: 274501-1-274501-4 (2001).
Gaud et al., "Acoustic Characterization of Single Ultrasound Contrast Agent Microbubbles", *The Journal of the Acoustic Society of America*, 124(6): 4091 (2008).
Ghosh, et al., "Cardiac Memory in Patients With Wolff-Parkinson-White Syndrome: Noninvasive Imaging of Activation and Repolarization Before and After Catheter Ablation", *Circulation*, 118:907-915 (2008).
Giacobini, "Alzheimer Disease, From Molecular Biology to Therapy", *Advances in Experimental Medicine and Biology*429:235-245 (1997).
Greenstein, et al., "Mechanisms of Excitation-Contraction Coupling in an Integrative Model of the Cardiac Ventricular Myocyte", *Biophysical Journal*, 90:77-91 (2006).
Greenwald, "Pulse Pressure and Arterial Elasticity", *Qjm-an International Journal of Medicine*, 95(2): 107-112 (2002).
Gupta, et al., "Changes in Passive Mechanical Stiffness of Myocardial Tissue with Aneurysm Formation", *Circulation*, 89:2315-2326 (1994).
Gurev, et al., "Distribution of Electromechanical Delay in the Heart: Insights From a Three-Dimensional Electromechanical Model", *Biophysical Journal*, 99:745-754 (2010).
Gurev, et al., "In Silico Characterization of Ventricular Activation Pattern by Electromechanical Wave Imaging", *Supplement to Heart Rhythm.*, 6:S357 (2009).
Heimdal, et al., "Real-time Strain Rate Imaging of the Left Ventricle by Ultrasound", *J Am Soc EchocardioG.*, 11(11): 1013-1019 (1998).
Henderson, et al., "Series Elasticity of Heart Muscle During Hypoxia", *Cardiovascular Research*, 5:10-14 (1971).
Housden, et al., "Ultrasonic imaging of 3D displacement vectors using a simulated 2D array and beamsteering", *Ultrasonics*, 53(2):615-621 (2013).
Huang, et al. "Watershed Segmentation for Breast Tumor in 2-D Sonography", *Ultrasound in Medicine and Biology*, pp. 625-632 (2004).
Hynynen, et al., "Demonstration of Potential Noninvasive Ultrasound Brain Therapy Through an Intact Skull", *Ultrasound in Medicine & Biology*, 24(2): 275-283 (1998).
Hynynen, et al., "Noninvasive MR Imaging—Guided Focal Opening of the Blood-Brain Barrier in Rabbits", *Radiology*, 220(3): 640-646 (2001).
Hynynen, et al., "Trans-Skull Ultrasound Therapy: The Feasibility of Using Image-Derived Skull Thickness Information to Correct the Phase Distortion", *IEEE Transactions on Ultrasonics, Ferroelectrics and Frequency Control*, 46(3): 752-755, (1999).
Hynynen, et al., "Focal Disruption of the Blood-Brain Barrier Due to 260-Khz Ultrasound Bursts: A Method for Molecular Imaging and Targeted Drug Delivery", *J Neurosurg.*, 105(3): 445-454 (2006).
International Search Report for PCT/US2007/019149 dated Feb. 29, 2008.
International Preliminary Report on Patentability, dated Jun. 11, 2008 and Written Opinion for PCT/US2006/061809, dated Oct. 4, 2007.

(56) References Cited

OTHER PUBLICATIONS

International Preliminary Report on Patentability, dated Nov. 14, 2007 and Written Opinion for PCT/US2006/018454, dated Aug. 9, 2007.
International Preliminary Report on Patentability, dated Apr. 17, 2007 and Written Opinion for PCT/US2005/037669, Jun. 13, 2006.
International Preliminary Report on Patentability, dated Apr. 17, 2007 and Written Opinion for PCT/US2005/037670, dated Nov. 22, 2006.
International Search Report and Written Opinion for PCT/US2010/049681, dated Dec. 7, 2010.
International Search Report and Written Opinion for PCT/US2010/061742, dated Mar. 1, 2011.
International Search Report and Written Opinion for PCT/US2009/056513, dated Oct. 30, 2009.
International Search Report and Written Opinion for PCT/US2009/052563 dated Oct. 8, 2009.
EPO Search Report and Opinion and Office Action for EP0684017.2 dated Dec. 7, 2009 and Mar. 8, 2010.
International Search Report and Written Opinion for PCT/US2009/056565 dated Nov. 2, 2009.
International Search Report and Written Opinion for PCT/US2006/036460, dated Sep. 5, 2007; International Preliminary Report dated Mar. 26, 2008.
Jagannathan, et al., "High-Intensity Focused Ultrasound Surgery of the Brain: Part 1—A Historical Perspective With Modern Applications", *Neurosurgery*, 64(2): 201-211 (2009).
Jasaityte, et al., "Current state of three-dimensional myocardial strain estimation using echocardiography", *J Am Soc Echocardiogr.*, 26(1):15-28 (2013).
Jensen, et al., "Calculation of Pressure Fields From Arbitrarily Shaped, Apodized, and Excited Ultrasound Transducers", *IEEE Transactions on Ultrasonics, Ferroelectrics and Frequency Control*, 39(2): 262-267 (1992).
Kallel, et al., "A Least-Squares Strain Estimator for Elastography", *Ultrasonic Imaging*, 19:195-208 (1997).
Kanai, et al. "Propagation of Spontaneously Actuated Pulsive Vibration in Human Heart Wall and in Vivo Viscoelasticity Estimation", *IEEE Transactions on Ultrasonics, Ferroelectrics, and Frequency Control*, 52(11): 1931-1942 (2005).
Kanai, et al., "Myocardial Rapid Velocity Distribution", *Ultrasound Med Biol.*, 27(4): 481-498 (2001).
Kanai, et al., "Transcutaneous Measurement of Frequency Dispersion in the Regional Pulse Wave Velocity", *2000 IEEE Ultrasonics Symposium*, pp. 1-4 (2000).
Kanai, et al., "A New Method for Measuring Small Local Vibrations in the Heart Using Ultrasound", *IEEE Transactions on Biomedical Engineering*, 40(12): 1233-1242 (1993).
Kaufman, et al., "Ultrasound Simulation in Bone," *IEEE Transactions on Ultrasonics Ferroelectrics and Frequency Control*, 55(6): 1205-1218 (2008).
Kimber, et al., "A Comparison of Unipolar and Bipolar Electrodes During Cardiac Mapping Studies", *Pacing Clin Electro.*, 19:1196-1204 (1996).
Kinoshita, et al., "Noninvasive Localized Delivery of Herceptin to the Mouse Brain by MRI-Guided Focused Ultrasound-Induced Blood-Brain Barrier Disruption", *Proceedings of the National Academy of Sciences*, 103(31): 11719-11723 (2006).
Kinoshita, et al., "Targeted Delivery of Antibodies Through the Blood-Brain Barrier by MRI-Guided Focused Ultrasound", *Biochemical and Biophysical Research Communications*, 340:1085-1090 (2006).
Klein, et al., "Interdependency of Local Capillary Density, Blood Flow, and Metabolism in Rat Brains", *Amer. J. Physiol.*, 251(6) Pt 2: H1333-H1340 (1986).
Klempner, et al., "Neutrophil Plasma Membranes I. High-Yield Purification of Human Neutrophil Plasma Membrane Vesicles by Nitrogen Cavitation and Differential Centrifugation", Journal of Cell Biology, 86:21-28 (1980).
Konofagou, et al., "Noninvasive electromechanical wave imaging and conduction-relevant velocity estimation in vivo", *Ultrasonics*, 50(2):208-215 (2010).
Konofagou, et al., "Mechanism and Safety at the Threshold of The Blood-Brain Barrier Opening In Vivo", *International Society on Therapeutic Ultrasound (ISTU)*, Aix-en-Provence, France, Sep. 21-24, 2009.
Konofagou, et al., "Noninvasive Electromechanical Wave Imaging and Conduction Velocity Estimation In Vivo", *2007 IEEE Ultrasonics Symposium*, pp. 969-972 (2007).
Konofagou, et al., "A New Elastographic Method for Estimation and Imaging of Lateral Strains, Corrected Axial Strains and Poison's Ratios in Tissues", *Ultrasound in Medicine and Biology*, 24(8):1183-1199 (1998).
Konofagou, et al., "Three-Dimensional Motion Estimation in Elastography", *IEEE Proceedings of the Symposium of Ultrasonics, Ferroelectrics and Frequency Control in Sendai*, Japan, pp. 1745-1748 (1998).
Konofagou, et al., "Myocardial Elastography—Feasibility Study in Vivo", *Ultrasound Med & Biol.*, 28(4):475-482 (2002).
Konofagou, et al. "Elastographic Imaging of the Strain Distribution at the Anterior Cruciate Ligament and ACL-Bone Insertions", *Proceedings of the 2005 IEEE 27th Annual International Conference of the Engineering in Medicine and Biology Society*, pp. 972-975 (Shanghai, China Sep. 1-4, 2005).
Korecka, et al., "Cell-Replacement and Gene-Therapy Strategies for Parkinson's and Alzheimers Disease", *Regen. Med.*, 2(4): 425-446 (2007).
Kremkau, et al., "Ultrasonic Attenuation and Propagation Speed in Normal Human Brain", *The Journal of the Acoustical Society of America*, 70:29 (1981).
Kunz, et al, "The Finite Difference Time Domain Method for Electromagnetics," *CRC Press*, Boca Raton, USA (1993).
Kvale, et al., "Size Fractionation of Gas-Filled Microspheres by Flotation", *Separations Technol.*, 6(4): 219-226 (1996).
Lai, et al., "Introduction to Continuum Mechanics" (Pergamon Pr). 3rd Ed. (1993).
Lee, et al., "Improving Stereotactic Surgery Using 3-D Reconstruction", *IEEE Engineering in Medicine and Biology Magazine*, 21:109-116 (2002).
Lee, et al., "Theoretical Quality Assessment of Myocardial Elastography With In Vivo Validation", *IEEE Transactions, Ultrasonics, Ferroelectrics and Frequency Control*, 54:2233-2245 (2007).
Liu, et al., "Hemorrhage Detection During Focused-Ultrasound Induced Blood-Brain-Barrier Opening by Using Susceptibility-Weighted Magnetic Resonance Imaging", *Ultrasound in Med. & Biol.*, 34(4): 598-606 (2008).
Liu, et al., "Magnetic Resonance Imaging Enhanced by Superparamagnetic Iron Oxide Particles: Usefulness for Distinguishing Between Focused Ultrasound-Induced Blood-Brain-Barrier Disruption and Brain Hemorrhage", *J. of Magnetic Resonance Imaging*, 29:31-38 (2009).
Lu, et al., "Design and Experiment of 256-Element Ultrasound Phased Array for Noninvasive Focused Ultrasound Surgery", *Ultrasonics*, 44:e325-e330 (2006).
Luo, et al., "A Fast Normalized Cross-Correlation Method for Motion Estimation", *IEEE Transactions, Ultrasonics, Ferroelectrics and Frequency Control*, 57(6): 1347-1357 (2010).
Luo, et al., "High-Frame Rate, Full-View Myocardial Elastography With Automated Contour Tracking in Murine Left Ventricles In Vivo", *IEEE Transactions, Ultrasonics, Ferroelectrics and Frequency Control*, 55(1): 240-248 (2008).
Luo, et al., "Myocardial Elastography at Both High Temporal and Spatial Resolution for the Detection of Infarcts", *Ultrasound Med. Biol.*, 33(8): 1206-1223 (2007).
Luo, et al., "Pulse Wave Imaging of Normal and Aneurysmal Abdominal Aortas In Vivo", *IEEE Trans. Med. Imaging*, 28(4): 477-486 (2009).
Maleke, et al., "In Vivo Feasibility of Real-Time Monitoring of Focused Ultrasound Surgery (FUS) Using Harmonic Motion Imaging (HMI)", *IEEE Trans, Biomed. Eng.*, 57(1): 7-11 (2010).

(56) References Cited

OTHER PUBLICATIONS

Maleke, et al., "Single-Element Focused Ultrasound Transducer Method for Harmonic Motion Imaging", *Ultrasonic Imaging*, 28(3): 144-158 (2006).
Marquet, et al., "Non-Invasive Transcranial Ultrasound Therapy Based on a 3D CT Scan: Protocol Validation and In Vitro Results", *Phys. Med. Biol.*, 54:2597-2613 (2009).
Mazziotta, et al., "A Probabilistic Atlas of the Human Brain: Theory and Rationale for Its Development the International Consortium for Brain Mapping (ICBM)", *Neuroimage*, 2:89-101 (1995).
McDannold, et al., "Targeted Disruption of the Blood-Brain Barrier With Focused Ultrasound: Association With Cavitations Activity", *Physics in Medicine and Biology*, 51:793-808 (2006).
McDannold, et al., "Use of Ultrasound Pulses Combined With Definity for Targeted Blood-Brain Barrier Disruption: A Feasibility Study", *Ultrasound in Medicine & Biology*, 33(4): 584-590 (2007).
McDannold, et al., "MRI-Guided Targeted Blood-Brain Barrier Disruption With Focused Ultrasound: Histological Findings in Rabbits", *Ultrasound Med. Biol.*, 31(11): 1527-1537 (2005).
McDannold, et al., "Blood-Brain Barrier Disruption Induced by Focused Ultrasound and Circulating Preformed Microbubbles Appears to be Characterized by the Mechanical Index", *Ultrasound Med Biol.*, 34(5):834-840 (2008).
McLaughlin, et al., "Piezoelectric Sensor Determination of Arterial Pulse Wave Velocity", *Physiol Meas.*, 24(3): 693-702 (2003).
McNally, et al., "Computer Vision Elastography: Speckle Adaptive Motion Estimation for Elastography Using Ultrasound Sequences", *IEEE Transactions on Medical Imaging*, 24(6):755-766 (2005).
Melodelima, et al., "Thermal Ablation by High-Intensity-Focused Ultrasound Using a Toroid Transducer Increases the Coagulated Volume. Results of Animal Experiments", *Ultrasound in Medicine & Biology*, 35(3): 425-435 (2009).
Mitri, et al., "Chirp Imaging Vibro-Acoustography for Removing the Ultrasound Standing Wave Artifact", *IEEE Transactions on Medical Imaging*, 24(10): 1249-1255 (2005).
Mychaskiw, et al., "Optison (FS069) Disrupts the Blood-Brain Barrier in Rats", *Anesthesia & Analgesia*, 91:798 (2000).
Nichols, et al., "Vascular Impedance. In McDonald's: Blood Flow in Arteries: Theoretical, Experimental and Clinical Principles", *E. Arnold. London, Oxford University Press*, Table of Contents (1998).
Ophir, et al., "Elastography: A Quantitative Method for Imaging the Elasticity of Biological Tissues", *Ultrasonic Imaging*, 3(2): 111-134 (1991).
Otani, "Use of ultrasound imaging to map propagating action potential waves in the heart", *Computers in Cardiology*, 36:617-620 (2009).
Palmeri, et al., "Characterizing acoustic attenuation of homogeneous media using focused impulsive acoustic radiation force", *Ultrason Imaging*, 28(2):114-128 (2006).
Papadakis, Emmauel P., "Ultrasonic Instruments & Devices", Academic Press, 8 pages (1999).
Pardridge, "Drug Targeting to the Brain", *Pharmaceutical Research*, 24:1733-1744 (2007).
Pardridge, "The Blood-Brain Barrier: Bottleneck in Brain Drug Development", *NeuroRx*, 2:3-14 (2005).
Patel, et al., "GDNF Delivery for Parkinson's Disease", *ACTA Neurochirurgica-Supplementum*, 97(2): 135-154 (2007).
Pernot, et al., "ECG-Gated, Mechanical and Electromechanical Wave Imaging of Cardiovascular Tissues In Vivo", *Ultrasound in Medicine & Biology*, 33(7):1075-1085 (2007).
Pernot, et al., "Electromechanical Imaging of the Myocardium at Normal and Pathological States", 2005 IEEE Ultrasonics Symposium, pp. 1091-1094 (2005).
Philippens, "Non-Human Primate Models for Parkinson's Disease", *Drug Discovery Today: Disease Models*, 5:105-111 (2008).
Pichardo, et al., "Multi Frequency Characterization of Speed of Sound for Longitudinal Transmission on Freshly Excised Human Skulls" *9th International Society on Therapeutic Ultrasound*, p. 136 (2009.).

Prinzen, et al., "The Time Sequence of Electrical and Mechanical Activation During Spontaneous Beating and Ectopic Stimulation", *Eur. Heart J.*, 13:535-543 (1992).
Provost, et al., "Electromechanical Wave Imaging of Normal and Ischemic Hearts In Vivo", *IEEE Trans. Med. Imaging*, 29:625-635 (2010).
Provost, et al., "Mapping of cardiac electrical activation with electromechanical wave imaging: An in silico-in vivo reciprocity study", *Heart Rhythm.*, 8(5):752-759 (2011).
Provost, et al., "Imaging the electromechanical activity of the heart in vivo", *PNAS*, 108(21):8565-8570 (2011).
Qin, et al., "Acoustic Response of Compliable Microvessels Containing Ultrasound Contrast Agents", *Phys. Med. Biol.*, 51:5065-5088 (2006).
Qin, et al., "The Natural Frequency of Nonlinear Oscillation of Ultrasound Contrast Agents in Microvessels", *Ultrasound in Med. & Biol.*, 33(7):1140-1148 (2007).
Ramanathan, et al., "Activation and Repolarization of the Normal Human Heart Under Complete Physiological Conditions", *Proceedings of the National Academy of Sciences*, 103:6309-6314 (2006).
Ramanathan, et al., "Noninvasive Electrocardiographic Imaging for Cardiac Electrophysiology and Arrhythmia", *Nat Med.*, 10:422-428 (2004).
Raymond, et al., "Ultrasound Enhanced Delivery of Molecular Imaging and Therapeutic Agents in Alzheimer's Disease Mouse Models", *PLoS One*, 3(5):e2175 (2008).
Rice, et al., "Approximate Model of Cooperative Activation and Crossbridge Cycling in Cardiac Muscle Using Ordinary Differential Equations", *Biophys. J.*, 95:2368-2390 (2008).
Rockenstein, et al., "Transgenic Animal Models of Neurodegenerative Diseases and Their Application to Treatment Development", *Adv. Drug Del. Rev.*, 59(11):1093-1102 (2007).
Rogers, et al., "Age-Associated Changes in Regional Aortic, Pulse Wave Velocity", *J Am Coll Cardiol.*, 38(4):1123-1129 (2001).
Roth, "Influence of a Perfusing Bath on the Foot of the Cardiac Action Potential", *Circulation Research*, 86:E19-E22 (2000).
Sabraoui, et al., "Feedback Loop Process to Control Acoustic Cavitation", *Ultrasonics Sonochemistry*, 18(2):589-594 (2011).
Samuel, et al., "An Ex Vivo Study of the Correlation Between Acoustic Emission and Microvascular Damage", *Ultrasound Med. Biol.*, 35(9):1574-1586 (2009).
Sanberg, et al., "Brief Communication: Neural Transplants Disrupt the Blood-Brain Barrier and Allow Peripherally Acting Drugs to Exert a Centrally Mediated Behavioral Effect", *Experimental Neurology*, 102:149-152 (1988).
Sandrin, et al., "Time-Resolved Pulsed Elastography with Ultrafast Ultrasonic Imaging", *Ultrason. Imaging*, 21(4): 259-72 (1999).
Sarvazyan, et al., "Shear Wave Elasticity Imaging: A New Ultrasonic Technology of Medical Diagnostics", *Ultrasound Med Biol.*, 24(9): 1419-1435 (1998).
Sassaroli, et al., "Forced Linear Oscillations of Microbubbles in Blood Capillaries", *J. Acoust. Soc. Am.*, 115(6):3235-3243 (2004).
Sassaroli, et al., "Resonance Frequency of Microbubbles in Small Blood Vessels: a Numerical Study", *Phys. Med. Biol.*, 50:5293-5305 (2005).
Sassaroli, et al., "Cavitation Threshold of Microbubbles in Gel Tunnels by Focused Ultrasound", *Ultrasound in Med. & Biol.*, 33(10):1651-1660 (2007).
Schenk, et al., "Immunization With Amyloid-Beta Attenuates Alzheimer-Disease-Like Pathology in the PDAPP Mouse",*Nature*, 400:173-177 (1999).
Scher, et al., "The Pathway of Ventricular Depolarization in the Dog", *Circ Res.*, 4:461-469 (1956).
Schilling, et al., "Simultaneous Endocardial Mapping in the Human Left Ventricle Using a Noncontact Catheter: Comparison of Contact and Reconstructed Electrograms During Sinus Rhythm", *Circulation*, 98:887-98 (1998).
Sengupta, et al., "Electromechanical Activation Sequence in Normal Heart", *Heart Fail Clin.*, 4:303-314 (2008).
Shehata, et al., "Myocardial Tissue Tagging With Cardiovascular Magnetic Resonance", *Journal of Cardiovascular Magnetic Resonance*, 11:55 (2009).

(56) References Cited

OTHER PUBLICATIONS

Sheikov, et al., "Brain Arterioles Show More Active Vesicular Transport of Blood-Borne Tracer Molecules Than Capillaries and Venules After Focused Ultrasound-Evoked Opening of the Blood-Brain Barrier", *Ultrasound Med. Biol.*, 32(9): 1399-1409 (2006).

Sheikov, et al., "Cellular Mechanisms of the Blood-Brain Barrier Opening Induced by Ultrasound in Presence of Microbubbles", *Ultrasound Med. Biol.*, 30(7): 979-989 (2004).

Sheikov, et al., "Effect of Focused Ultrasound Applied With an Ultrasound Contrast Agent on the Tight Junctional Integrity of the Brain Microvascular Endothelium", *Ultrasound Med. Biol.*, 34(7): 1093-1104 (2008).

Silva, "Nanotechnology Approaches to Crossing the Blood-Brain Barrier and Drug Delivery to the CNS", *BMC Neruosci.*, 9(Suppl 3): S4 (2008).

Siegel, et al., "Neurotrophic Factors in Alzheimer's and Parkinson's Disease Brain", *Brain Research Reviews*, 33:199-227 (2000).

Sinkus, et al., "High-Resolution Tensor MR Elastography for Breast Tumour Detection", *Phys Med Biol.*, 45(6): 1649-1664 (2000).

Sirsi, et al., "Effect of Microbubble Size on Fundamental Mode High Frequency Ultrasound Imaging in Mice", *Ultrasound in Med. & Bio.*, 36(6): 935-948 (2010).

Spach, et al., "Extracellular Discontinuities in Cardiac Muscle—Evidence for Capillary Effects on the Action Potential Foot", *Circulation Research*, 83:1144-1164 (1998).

Stewart, et al., "Blood-Eye Barriers in the Rat: Correlation of Ultrastructure With Function", *J. Comp. Neurol.*, 340(4): 566-576 (1994).

Stieger, et al., "Enhancement of Vascular Permeability With Low-Frequency Contrast-Enhanced Ultrasound in the Chorioallantoic Membrane Model", *Radiology*, 243(1): 112-121 (2007).

Styner, et al., "Automatic Brain Segmentation in Rhesus Monkeys" *2007 Medical Imaging, Proc. of SPIE*, 6512:65122L-1-65122L-8 (2007).

Sutherland, "Color Doppler Myocardial Imaging—Potential Applications in Acquired and Congenital Heart-Disease", *Acta Paediatr.*, 84:40-48 (1995).

Sykova, et al., "Diffusion in Brain Extracellular Space", *Physiol, Rev.*, 88(4): 1277-1340 (2008).

Talu, et al., "Tailoring the Size Distribution of Ultrasound Contrast Agents: Possible Method for Improving Sensitivity in Molecular Imaging" *Mol. Imag.*, 6(6): 384-392 (2007).

Tang, et al., "Standing-Wave Suppression for Transcranial Ultrasound by Random Modulation", *IEEE transactions on Biomedical Engineering*, 57(1):203-205 (2010).

Tanter, et al., "Ultrafast Compound Imaging for 2-D Motion Vector Estimation: Application to Transient Elastography", *IEEE Trans Ultrason Ferroelectr Freq Control*, 49(10): 1363-74 (2002).

Tanter, et al., "Focusing and Steering Through Absorbing and Aberrating Layers: Application to Ultrasonic Propagation Through the Skull", *The Journal of the Acoustical Society of America*, 103:2403-2410 (1998).

Tavarozzi, et al., "Magnetocardiography: Current Status and Perspectives Part II: Clinical Applications", *Ital Heart J.*, 3:151-165 (2002).

Techavipoo, et al., "Temperature dependence of ultrasonic propagation speed and attenuation in excised canine liver tissue measured using transmitted and reflected pulses", *The Journal of Acoustical Society of America*, 115(6):2859-2865 (2004).

Treat, et al., "Targeted Delivery of Doxorubicin to the Rat Brain at Therapeutic Levels Using MRI-Guided Focused Ultrasound", *Int. J. Cancer*, 121(4): 901-907 (2007).

Tung, et al., "Identifying the Inertial Cavitation Threshold and Skull Effects in a Vessel Phantom Using Focused Ultrasound and Microbubbles", *Ultrasound in Medicine & Biology*, 36(5): 840-852 (2010).

Tung, et al., "Identifying the Inertial Cavitation Threshold in a Vessel Phantom Using Focused Ultrasound and Microbubbles", *The Journal of the Acoustical Society of America*, 124:2486 (2008).

Tung, et al., "Feasibility of Noninvasive Cavitation-Guided Blood-Brain Barrier Opening Using Focused Ultrasound and Microbubbles in Nonhuman Primates", *Applied Physics Letters*, 98(16):163704 (2001).

Tung, et al., "Noninvasive In Vivo Cavitation Threshold Detection During Blood-Brain Barrier Opening Using Focused Ultrasound and the Contrast Agent and Definity", *Joint 159th Meeting of the Acoustic Society of America*, (Apr. 19, 2010).

Tuszynski, et al., "A Phase 1 Clinical Trial of Nerve Growth Factor Gene Therapy for Alzheimer Disease", *Nature Medicine*, 11:551-555 (2005).

Tuszynski, et al., "Nerve Growth Factor Gene Therapy in Alzheimer Disease" *Alzheimer Disease & Associated Disorders*, 21:179-189 (2007).

Unger, E.C. et al., "Therapeutic Applications of Lipid-Coated Microbubbles", *Advanced Drug Delivery Reviews*, 56(9):1291-1314 (2004).

Vappou, et al., "Quantitative Viscoelastic Parameters Measured by Harmonic Motion Imaging", *Phys. Med. Biol.*, 54:3579-3595 (2009).

Walker, et al., "A Fundamental Limit on the Performance of Correlation Based Phase Correction and Flow Estimation Techniques", *IEEE Transactions, Ultrasonics, Ferroelectrics and Frequency Control*, 41(5): 644-654 (1994).

Walker, et al., "A Fundamental Limit on Delay Estimation Using Partially Correlated Speckle Signals", *IEEE Transactions, Ultrasonics, Ferroelectrics and Frequency Control*, 42(2): 301-308 (1995).

Wang, et al., "A Composite Imaging Technique for High Frame-Rate and Full-View Cardiovascular Ultrasound and Elasticity Imaging", *IEEE Transactions, Ultrasonics, Ferroelectrics and Frequency Control*, 55(10): 2221-2233 (2008).

Wang, et al., "A Composite Imaging Technique for High Frame-Rate and Full-View Cardiovascular Ultrasound and Elasticity Imaging", *IEEE International Ultrasonics Symposium*, New York, NY, Oct. 28-31, 2007.

Wang et al., "Qualitative and Quantitative Analysis of the Molecular Delivery Through the Ultrasound-Enhanced Blood-Brain Barrier Opening in the Murine Brain," *presented at the IEEE Symp. Ultrason, Ferroelectr. Freq. Control*, Beijing, China, 2008.

Wang, et al., "Increased Aortic Stiffness Assessed by Pulse Wave Velocity in Apolipoprotein E-Deficient Mice", *Am J. Physiol Heart Circ Physiol.*, 278(2): H428-34 (2000).

Wenk, "A Primate Model of Alzheimer's Disease", *Behavioural Brain Research*, 57:117-122 (1993).

White, et al., "Longitudinal and Shear Mode Ultrasound Propagation in Human Skull Bone", *Ultrasound in Medicine & Biology*, 32:1085-1096 (2006).

Wyman, et al., "Mapping Propagation of Mechanical Activation in the Paced Heart With MRI Tagging", *Am J Physiol Heart Circ Physiol*, 276:H881-891 (1999).

Xu, et al., "Controllable Gas-Liquid Phase Flow Patterns and Monodisperse Microbubbles in a Microfluidic T-Junction Device", *Appl. Phys. Lett.*, 88(13): 133506-1-133506-3 (2006).

Yin, et al., "A Numerical Study of Transcranial Focused Ultrasound Beam Propagation at Low Frequency", *Physics in Medicine and Biology*, 50:1821-1836 (2005).

Yuh, et. al. "Delivery of Systemic Chemotherapeutic Agent to Tumors by Using Focused Ultrasound: Study in a Murine Model", *Radiology*, 234(2): 431-437 (2005).

Zerhouni, et al., "Human Heart: Tagging with MR Imaging—A Method for Noninvasive Assessment of Myocardial Motion", *Radiology*, 169(1): 59-63 (1988).

Zhang, et al., "Noninvasive Three-Dimensional Electrocardiographic Imaging of Ventricular Activation Sequence", *Am J Physiol Heart Circ Physiol*, 289:H2724-32 (2005).

Zheng, et al., "Ultrasound-Driven Microbubble Oscillation and Translation Within Small Phantom Vessels", *Ultrasound Med. Biol.*, 33(12): 1978-1987 (2007).

Zheng, et al. "High Resolution Ultrasound Elastomicroseopy Imaging of Soft Tissues: System Development and Feasibility; Ultrasound Elastomicroscopy", *Physics in Medicine and Biology*, 49(17):3925-3938 (2004).

(56) References Cited

OTHER PUBLICATIONS

Zlokovic, "The Blood-Brain Barrier in Health and Chronic Neurodegenerative Disorders", *Neuron*, 57(2): 178-201 (2008).
Zwanenburg, et al., "Timing of Cardiac Contraction in Humans Mapped by High-Temporal-Resolution MRI Tagging: Early Onset and Late Peak of Shortening in Lateral Wall", *Am J Physiol Heart Circ Physiol.*, 286:H1872-1880 (2004).
Konofagou et al., "Electromechanical Wave Imaging for Noninvasive Mapping of the 3D Electrical Activation Sequence in Canines and Humans In Vivo", Journal of Biomechanics, 45(5):856-864 (2012).
Ohtani, et al., "Transmural Ultrasound-Based Visualization of Patterns of Action Potential Wave Propogation in Cardiac Tissue", Annals Biomedical Engineering, 38(10):3112-3123 (2010).
U.S. Appl. No. 14/300,106, filed Jun. 9, 2014.
U.S. Appl. No. 12/077,612, Mar. 21, 2014 Final Office Action.
U.S. Appl. No. 12/096,254, Mar. 21, 2014 Final Office Action.
U.S. Appl. No. 11/697,573, Jun. 16, 2014 Non-Final Office Action.
U.S. Appl. No. 13/426,400, May 5, 2014 Non-Final Office Action.
U.S. Appl. No. 13/529,239, Jun. 30, 2014 Amendment and Request for Continued Examination (RCE).
Zheng, et al., "Ultrasonic measurement of depth-dependent transient behaviors of articular cartilage under compression", *Journal of Biomechanics*, 38:1830-1837 (2005).
Epstein-Barasg, et al., A microcomposite hydrogel for repeated on-demand ultrasound-triggered drug delivery, *Biomaterials*, 31(19):5208-5217 (2010).
Konofagou, et al., "Ultrasound-Induced Blood-Brain Barrier Opening", *Current Pharmaceutical Biotechnology*, 13(7):1332-1345 (2012).
Chen, et al., "The size of blood-brain barrier opening induced by focused ultrasound is dictated by the acoustic pressure", J. Cereb. Blood Flow Metab., 34:1197-1204 (2014).
Carman, et al., "Adenosine receptor signaling modulates permeability of the blood-brain barrier", *The Journal of Neuroscience*, 31(37):13272-13280 (2011).
Shinna, et al., "Realtime tissue elasticity imaging using the combined autocorrelation method", *J. Med. Ultrasonics*, 29(autumn):119-128 (2002).
U.S. Appl. No. 13/529,239, Jul. 5, 2013 Non-Final Office Action.
U.S. Appl. No. 13/353,148, Sep. 11, 2013 Response to Non-Final Office Action.
U.S. Appl. No. 13/353,148, Jun. 20, 2013 Non-Final Office Action.
U.S. Appl. No. 12/096,254, Aug. 23, 2013 Non-Final Office Action.
U.S. Appl. No. 11/697,573, Sep. 4, 2013 Response to Non-Final Office Action.
U.S. Appl. No. 12/077,612, Aug. 30, 2013 Non-Final Office Action.
U.S. Appl. No. 11/433,510, Jul. 23, 2014 Issue Fee Payment.
U.S. Appl. No. 11/433,510, Apr. 23, 2014 Notice of Allowance.
U.S. Appl. No. 11/433,510, Apr. 7, 2014 Applicant Initiated Interview Summary.
U.S. Appl. No. 11/433,510, Apr. 4, 2014 Response to Non-Final Office Action.
U.S. Appl. No. 11/433,510, Oct. 4, 2013 Non-Final Office Action.
U.S. Appl. No. 11/697,573, Jan. 12, 2015 Notice of Abandonment.
U.S. Appl. No. 12/077,612, Oct. 29, 2015 Notice of Abandonment.
U.S. Appl. No. 12/077,612, Apr. 9, 2015 Non-Final Office Action.
U.S. Appl. No. 12/096,254, Sep. 28, 2015 Notice of Abandonment.
U.S. Appl. No. 12/096,254, Feb. 27, 2015 Non-Final Office Action.
U.S. Appl. No. 13/019,029, Mar. 21, 2013 Issue Fee payment.
U.S. Appl. No. 13/045,070, Feb. 24, 2016 Issue Fee Payment.
U.S. Appl. No. 13/045,070, Jan. 15, 2016 Notice of Allowance.
U.S. Appl. No. 13/045,070, Jan. 15, 2016 Applicant Initiated Interview Summary.
U.S. Appl. No. 13/045,070, Jan. 7, 2016 Notice of Appeal Filed.
U.S. Appl. No. 13/045,070, Nov. 17, 2015 Response after Final Action.
U.S. Appl. No. 13/045,070, Jul. 7, 2015 Final Office Action.
U.S. Appl. No. 13/045,070, May 18, 2015 Applicant Initiated Interview Summary.
U.S. Appl. No. 13/045,070, May 15, 2015 Response to Non-Final Office Action.
U.S. Appl. No. 13/045,070, Jan. 16, 2015 Non-Final Office Action.
U.S. Appl. No. 13/353,148, Feb. 26, 2016 Notice of Abandonment.
U.S. Appl. No. 13/353,148, Aug. 12, 2015 Non-Final Office Action.
U.S. Appl. No. 13/353,148, Jul. 6, 2015 Amendment and Request for Continued Examination (RCE).
U.S. Appl. No. 13/353,148, Mar. 3, 2015 Final Office Action.
U.S. Appl. No. 13/353,148, Oct. 24, 2014 Response to Non-Final Office Action.
U.S. Appl. No. 13/353,148, Oct. 14, 2014 Applicant Initiated Interview Summary.
U.S. Appl. No. 13/353,148, Apr. 24, 2014 Non-Final Office Action.
U.S. Appl. No. 13/353,148, Feb. 25, 2014 Applicant Initiated Interview Summary.
U.S. Appl. No. 13/353,148, Feb. 5, 2016 Notice of Allowance.
U.S. Appl. No. 13/426,400, Dec. 4, 2015 Applicant Initiated Interview Summary.
U.S. Appl. No. 13/426,400, Dec. 4, 2015 Response to Non-Final Office Action.
U.S. Appl. No. 13/426,400, Jul. 2, 2015 Non-Final Office Action.
U.S. Appl. No. 13/426,400, Mar. 23, 2015 Amendment and Request for Continued Examination (RCE).
U.S. Appl. No. 13/426,400, Dec. 23, 2014 Final Office Action.
U.S. Appl. No. 13/426,400, Oct. 2, 2014 Response to Non-Final Office Action.
U.S. Appl. No. 13/529,239, Jan. 8, 2016 Notice of Abandonment.
U.S. Appl. No. 13/529,239, Jun. 4, 2015 Final Office Action.
U.S. Appl. No. 13/529,239, Mar. 5, 2015 Applicant Initiated Interview Summary.
U.S. Appl. No. 13/529,239, Mar. 3, 2015 Response to Non-Final Office Action.
U.S. Appl. No. 14/300,106, Dec. 22, 2015 Issue Fee Payment.
U.S. Appl. No. 14/300,106, Sep. 24, 2015 Notice of Allowance.
U.S. Appl. No. 14/457,023, Mar. 2, 2016 Non-Final Office Action.
Alam et al., "An Adaptive Strain Estimator for Elastography," IEEE Transactions on Ultrasonics, Ferroelectrics, and Frequency Control, vol. 45, No. 2, Mar. 1998, pp. 461-472.
Amin et al., "Therapy planning and monitoring of tissue ablation by high intensityfocused ultrasound (HIFU) using imaging and simulation", Conf Proc IEEE Eng Med Biol Soc. 2008, 4471.
Hynynen et al., "Local and reversible blood-brain barrier disruption by noninvasive focused ultrasound at frequencies suitable for transskull sonications" NeuroImage 24 (2005) 12-20.
International Search Report and Written Opinion dated Jul. 17, 2012 in International Application No. PCT/US12/34136.
International Search Report and Written Opinion dated Oct. 18, 2012 in International Application No. PCT/US12/35685.
Liu et al., "Opening of the Blood-Brain Barrier by Low-Frequency (28-kHz) Ultrasound: A Novel Pinhole-Assisted Mechanical Scanning Device", Ultrasound in Med & Biol., vol. 36, Issue 2, Feb. 2010, pp. 325-335.
Long et al., "An integrated system for therapy planning of high intensity focused ultrasound", Electro/Information Technology, 2008. EIT 2008. IEEE International Conference on May 18-20, 2008, pp. 461-464.
Spalazzi et al., "Elastographic Imaging of Strain Distribution within the Anterior Cruciate Ligament and at the AGL-Bone Insertions," IEEE Ultrasonics Symposium, Sep. 2005, pp. 1755-1758.
Vaezy et al., "Real-time visualization of high-intensity focused ultrasound treatment using ultrasound imaging", Ultrasound Med Biol., Jan. 2001, 27(1), pp. 33-42.
Zheng et al., "A Targeting Method Based on Acoustic Backscatter for Treatment Planning in Tissue Ablation Using Focused Ultrasound", IEEE Trans on Biomed Eng. vol. 57, No. 1, Jan. 2010, pp. 71-79.
Ziadloo et al., "Real-time 3D image-guided HIFU therapy", Conf Proc IEEE Eng Med Biol Soc. 2008, 4459-62.

\* cited by examiner

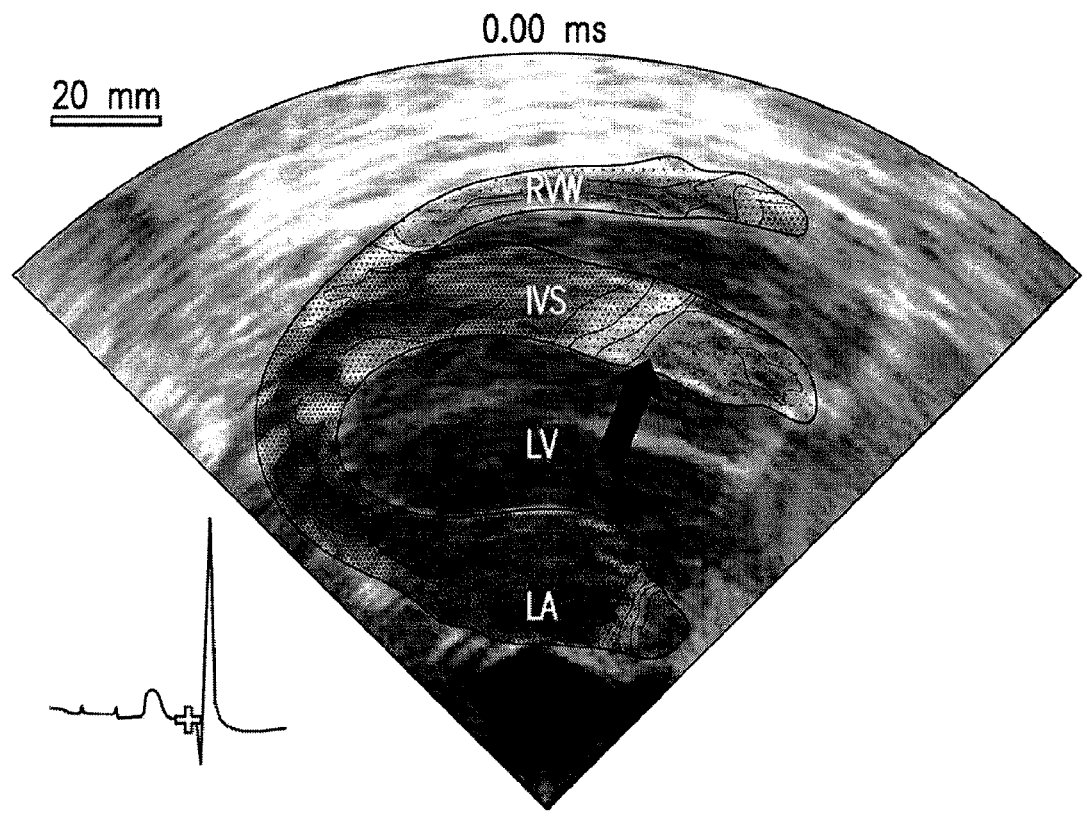
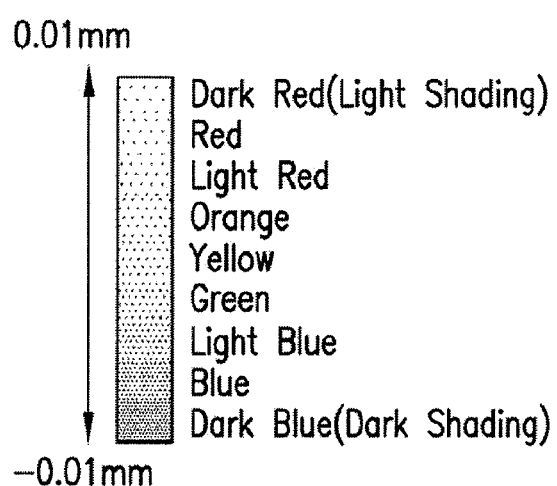
FIG.7(a)1

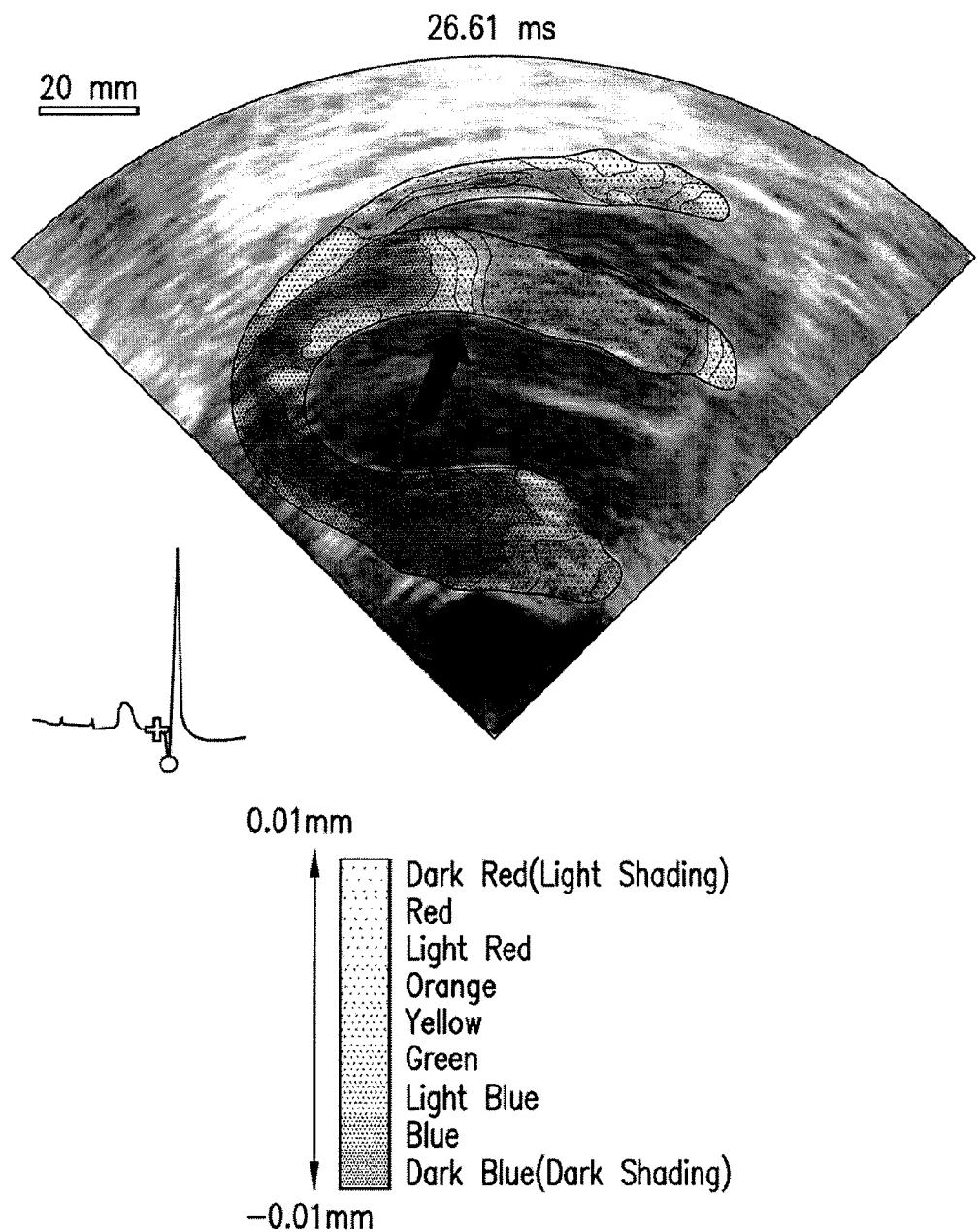
FIG.7(a)2

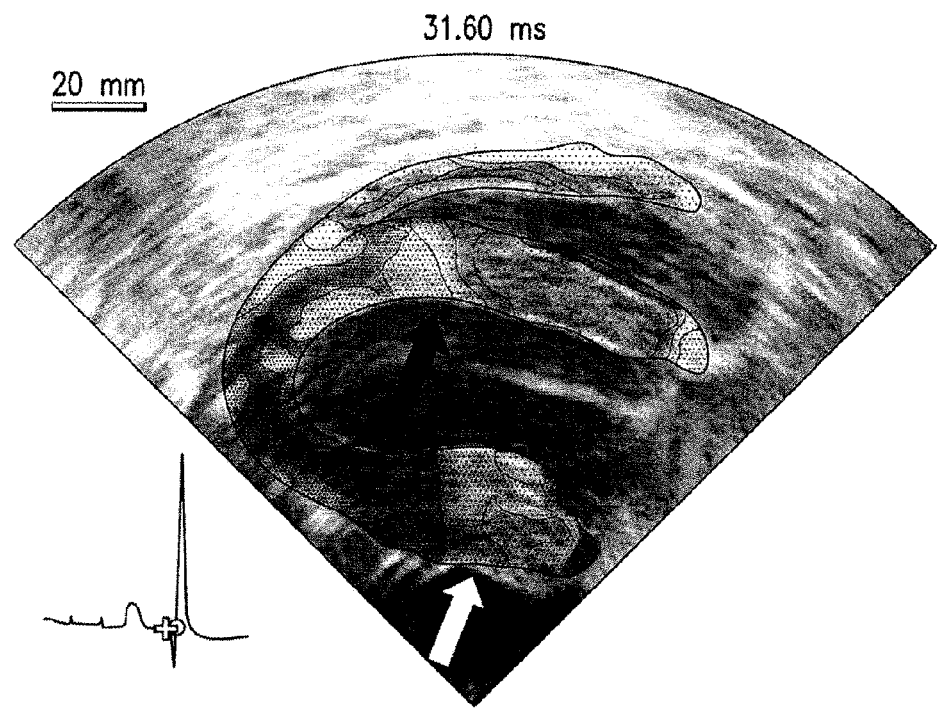
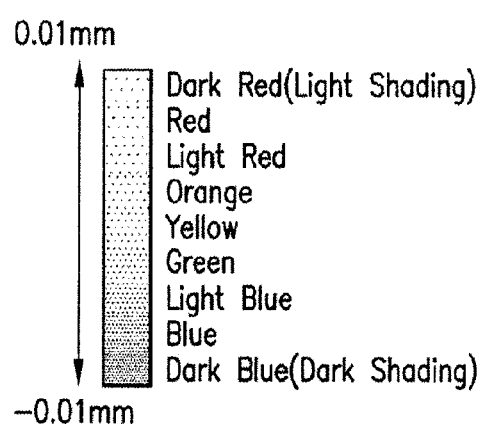
FIG.7(a)3

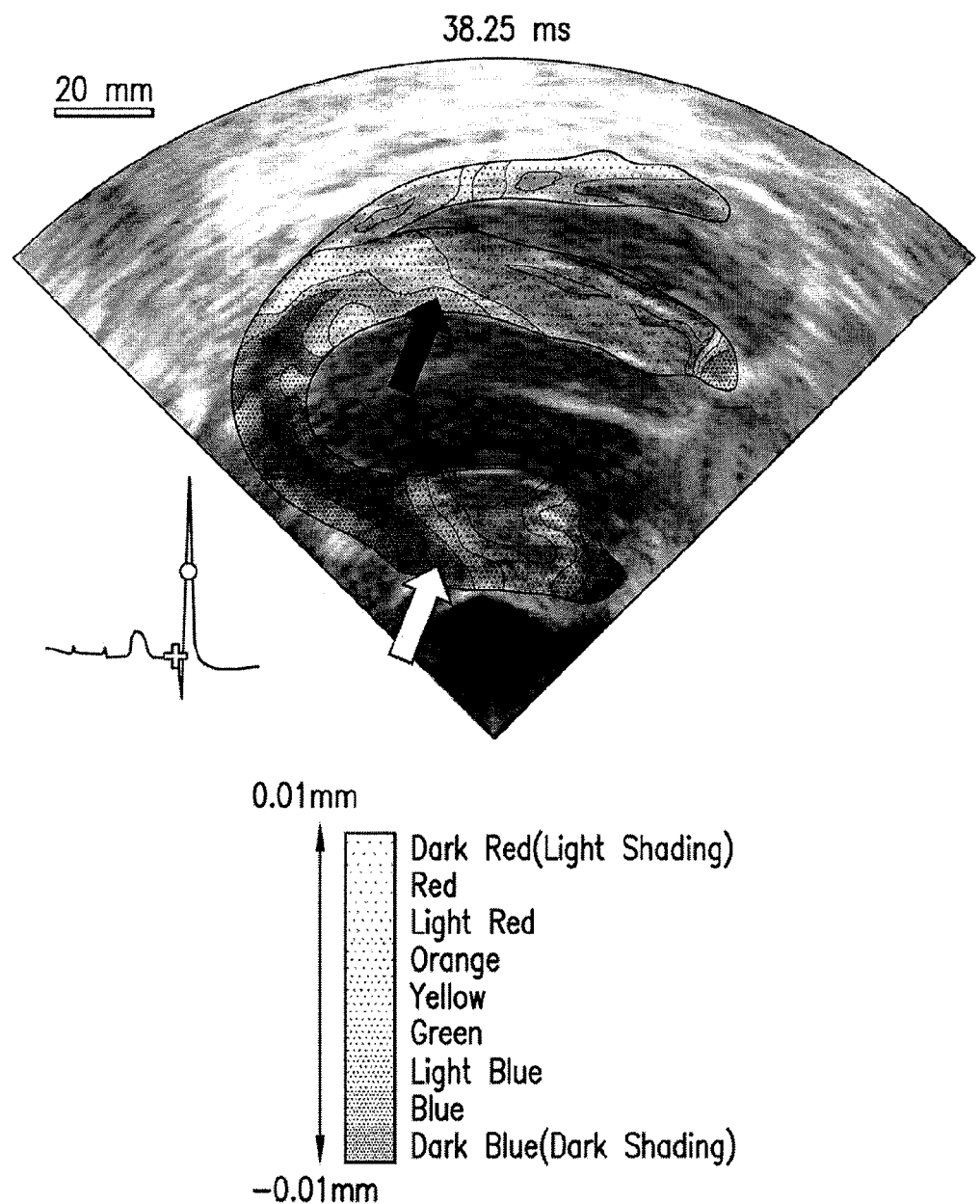
FIG.7(a)4

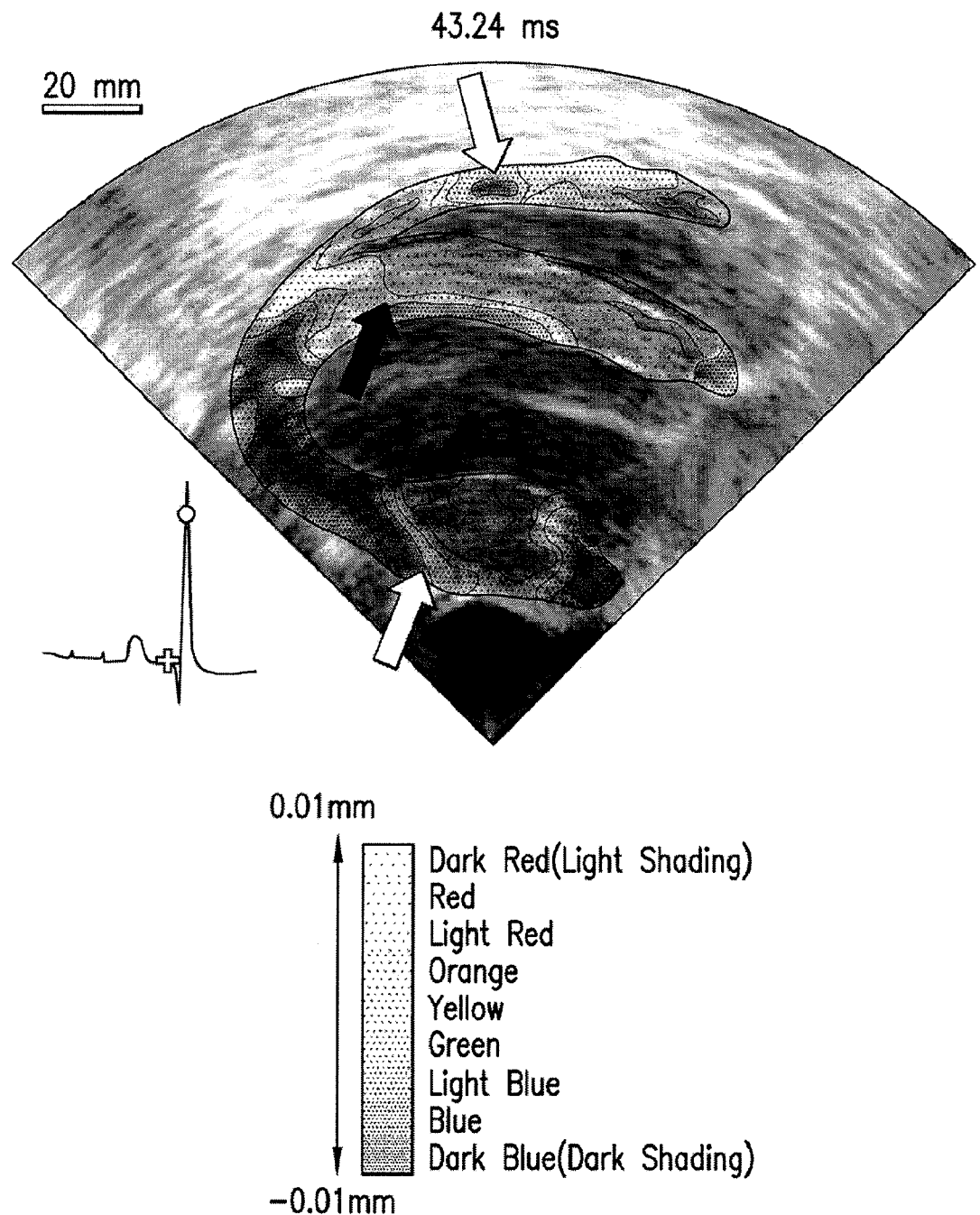
FIG.7(a)5

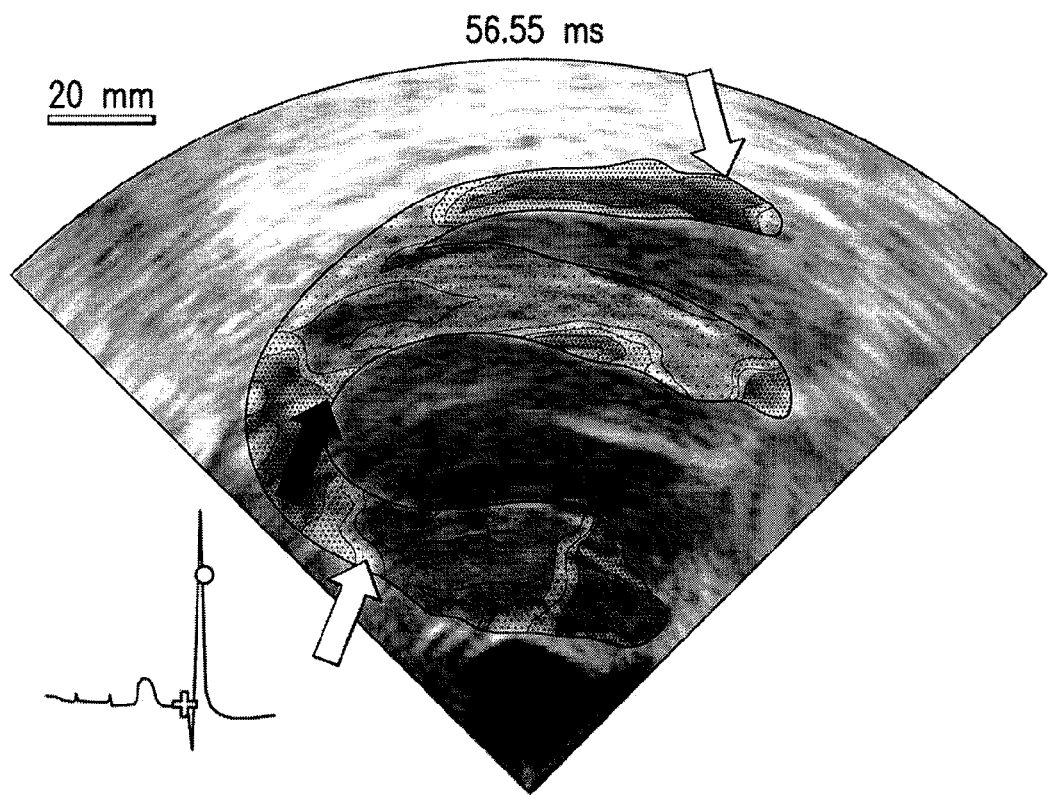
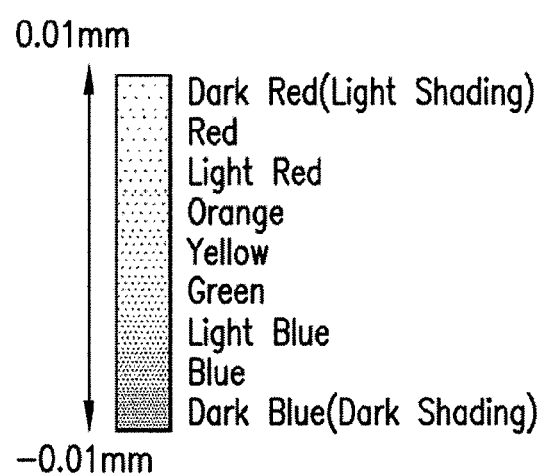
FIG.7(a)6

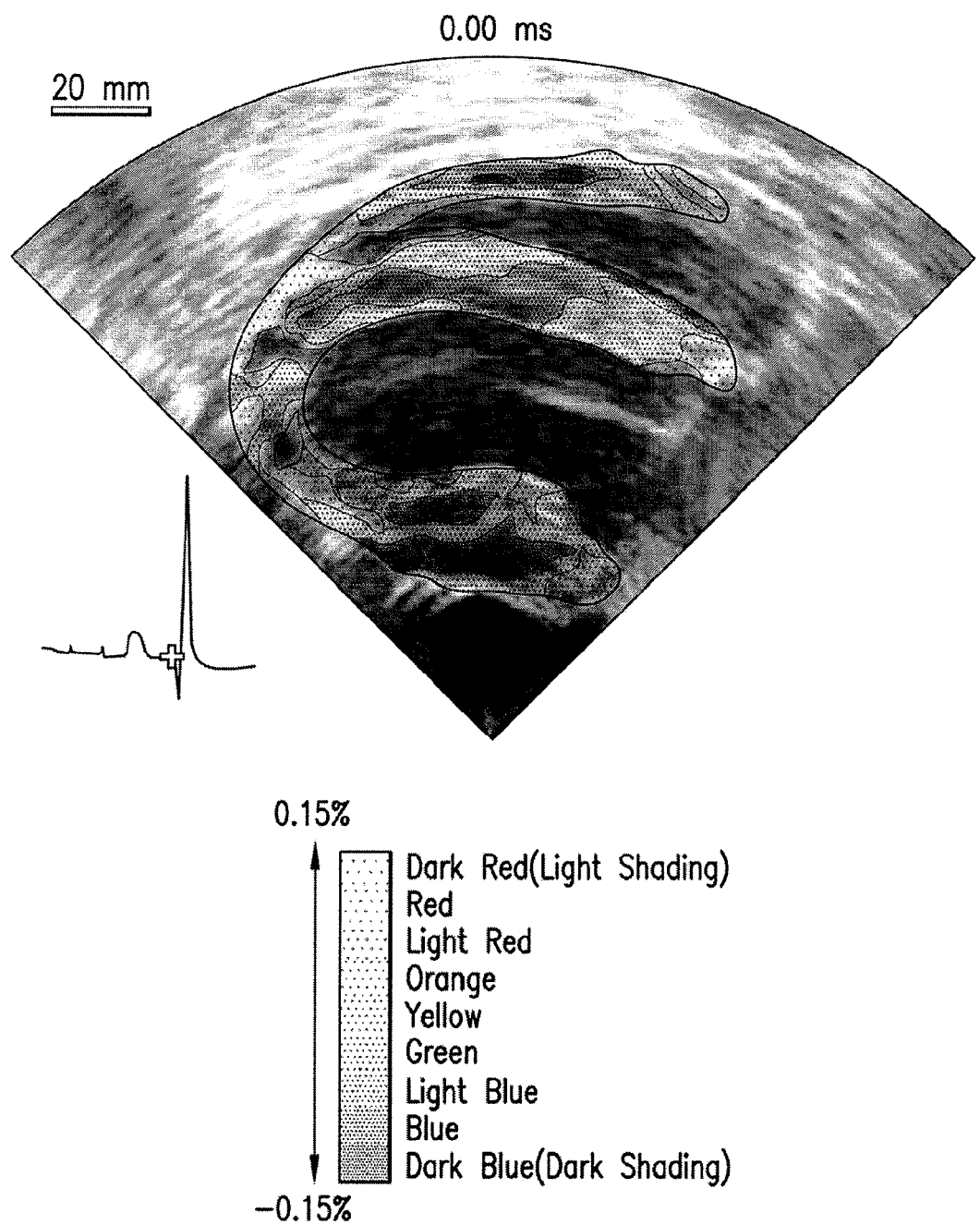
FIG.7(b)1

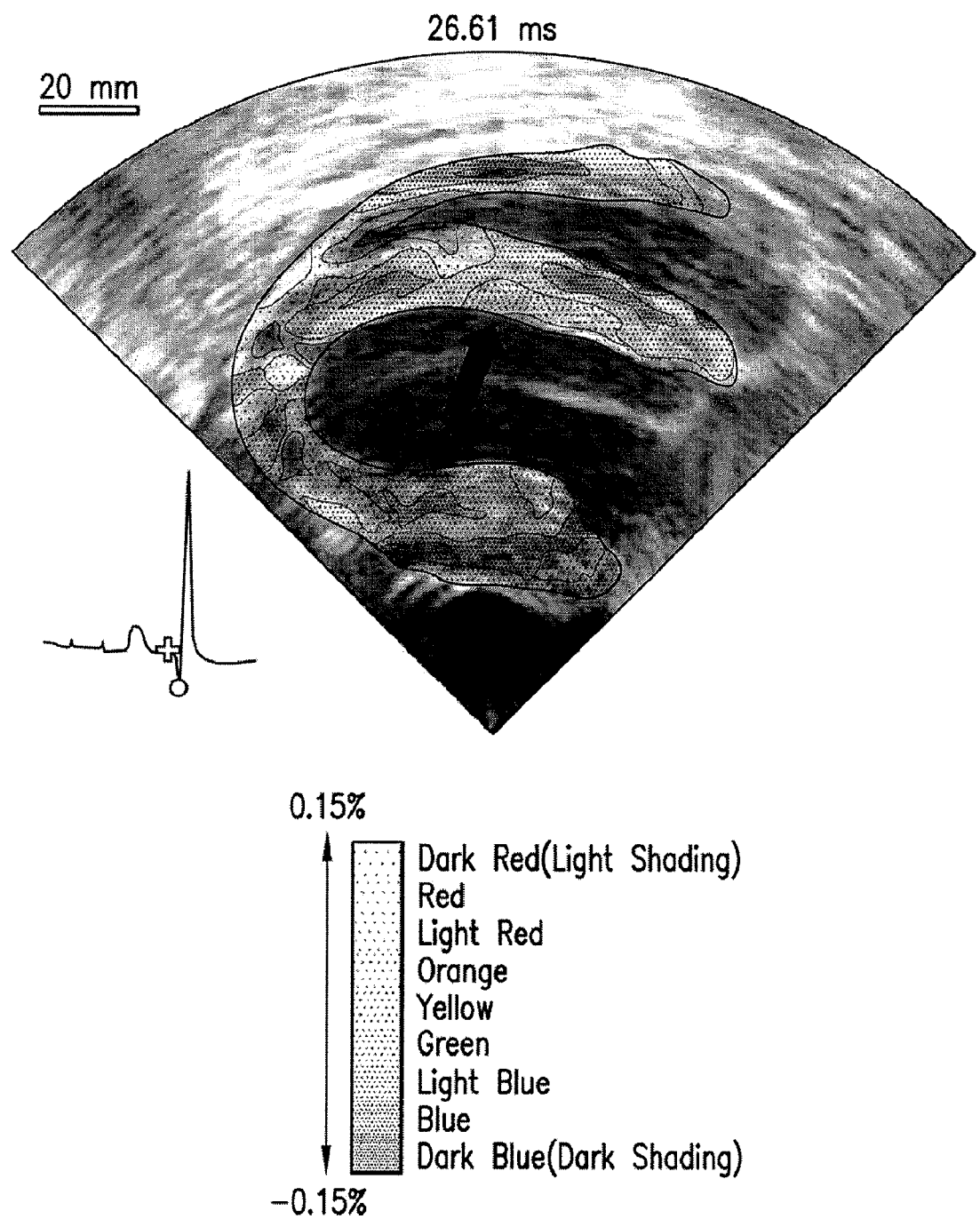
FIG.7(b)2

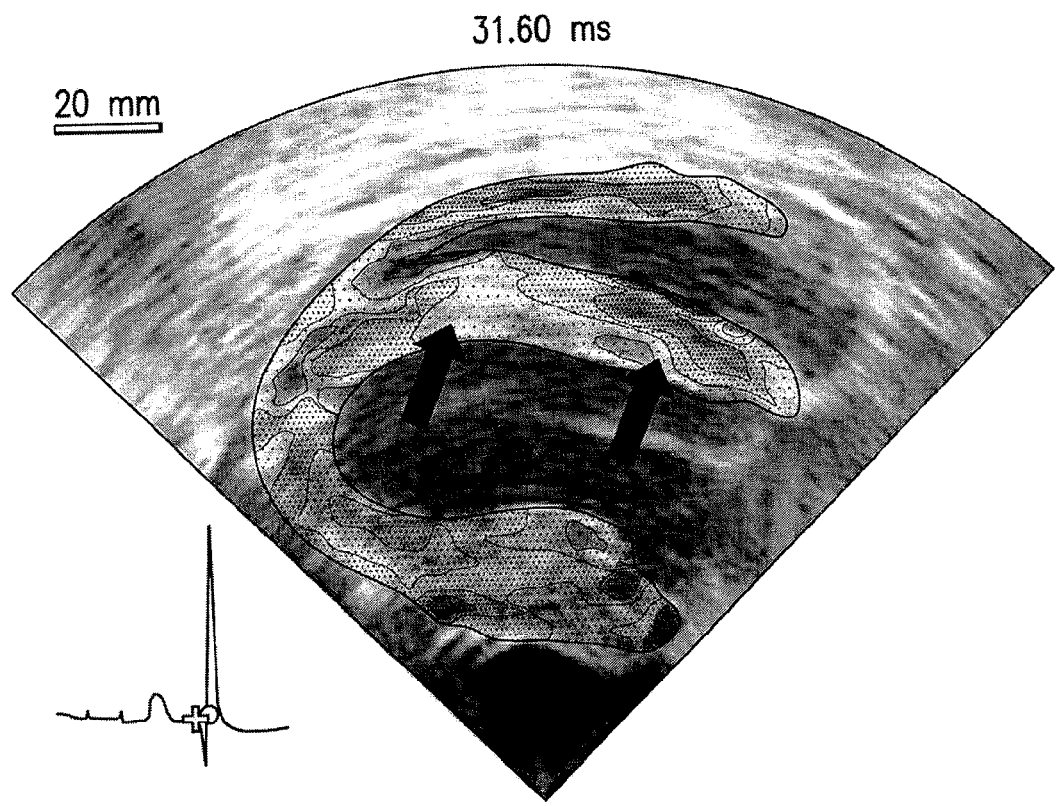
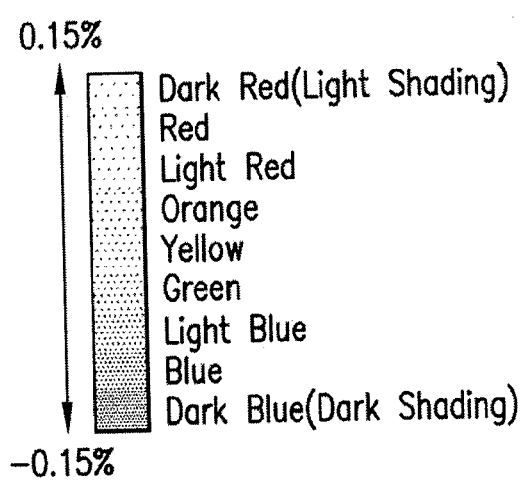
FIG.7(b)3

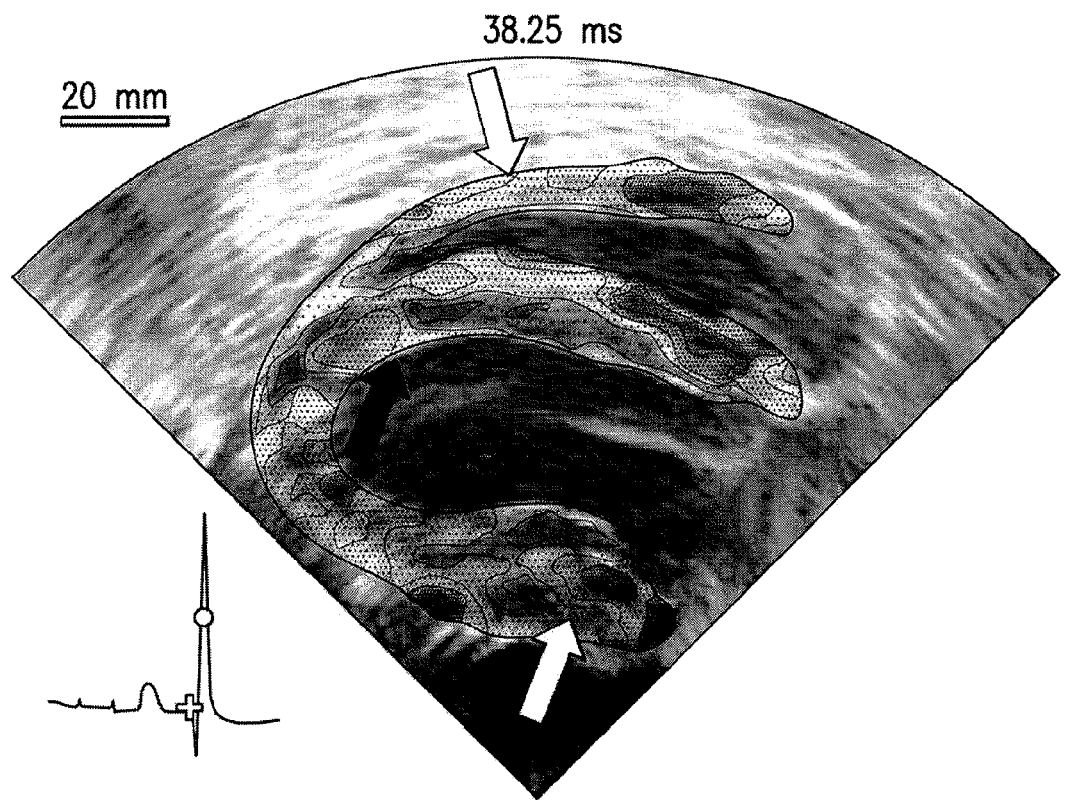
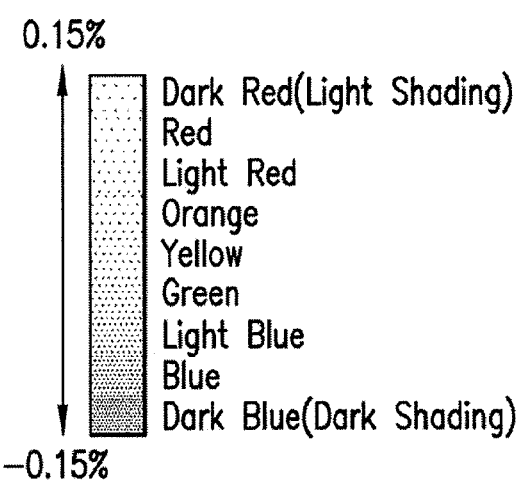
FIG.7(b)4

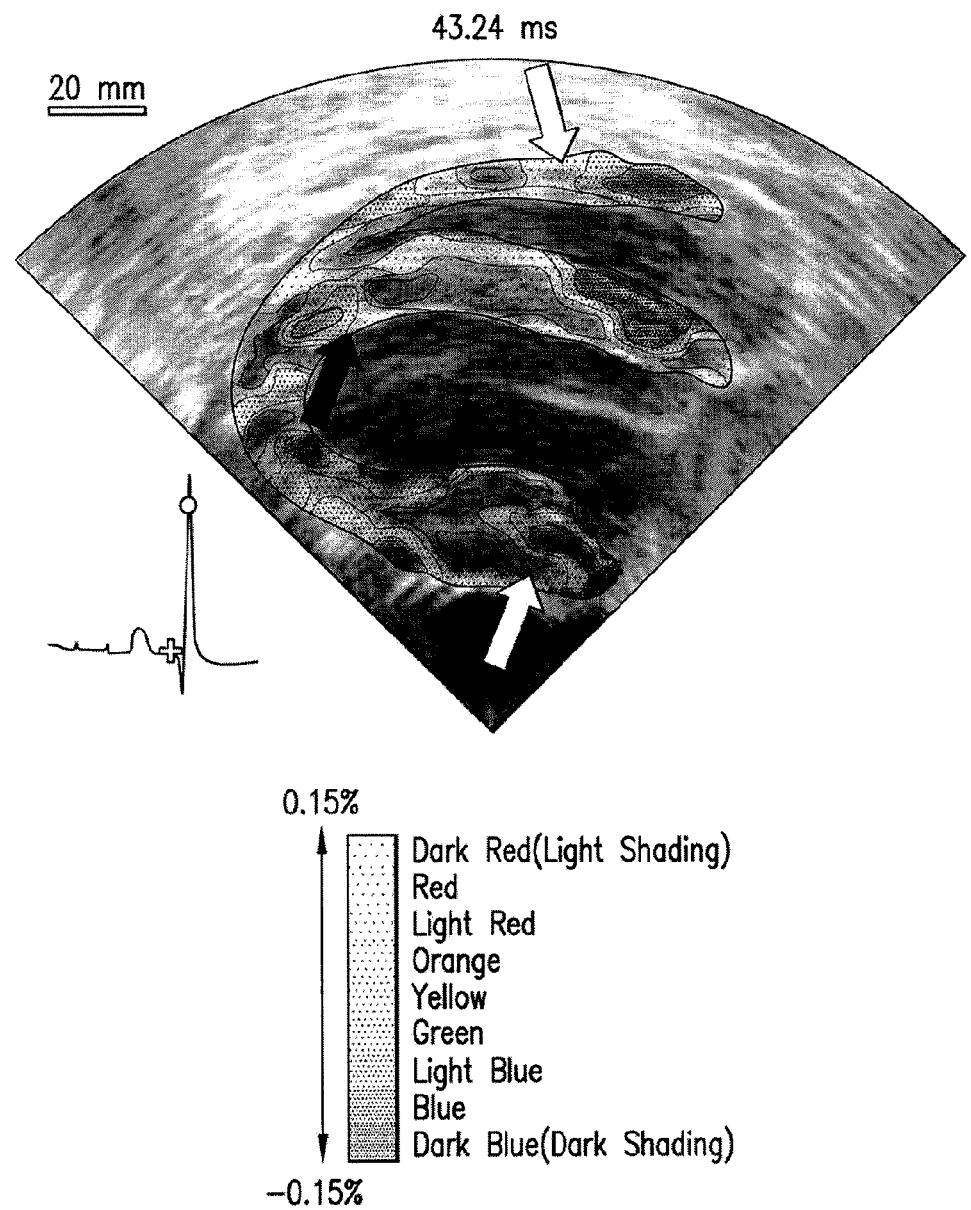
FIG.7(b)5

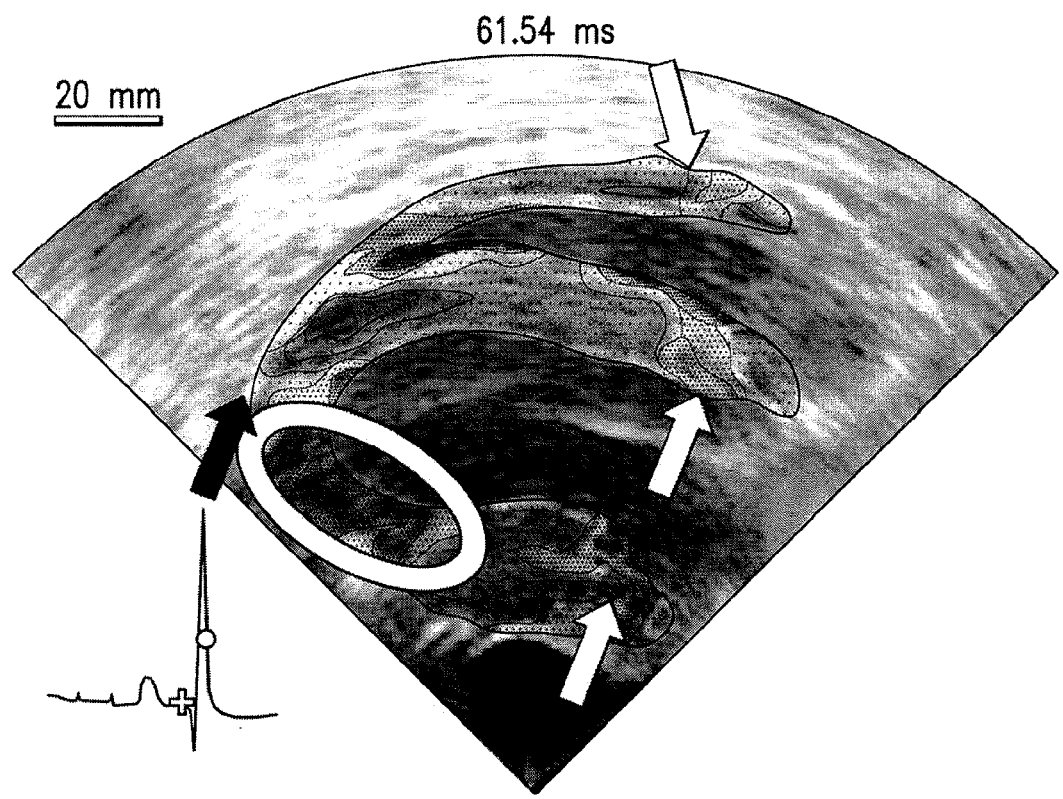
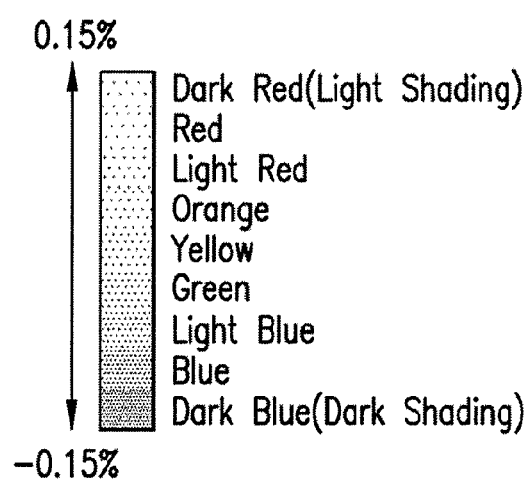
FIG.7(b)6

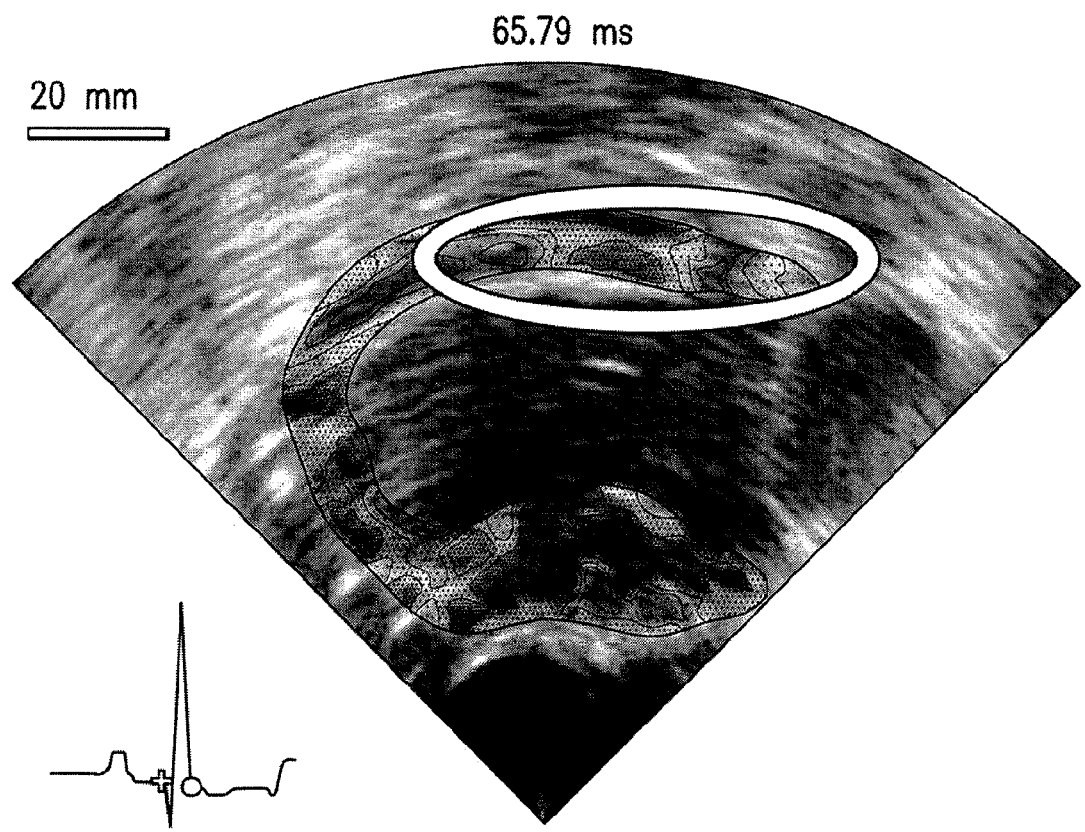
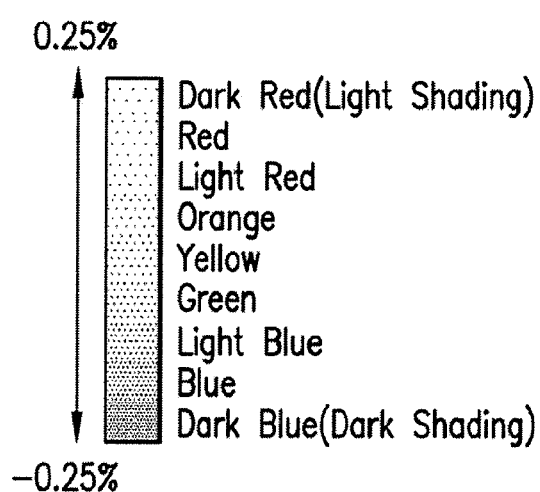
FIG.8-8

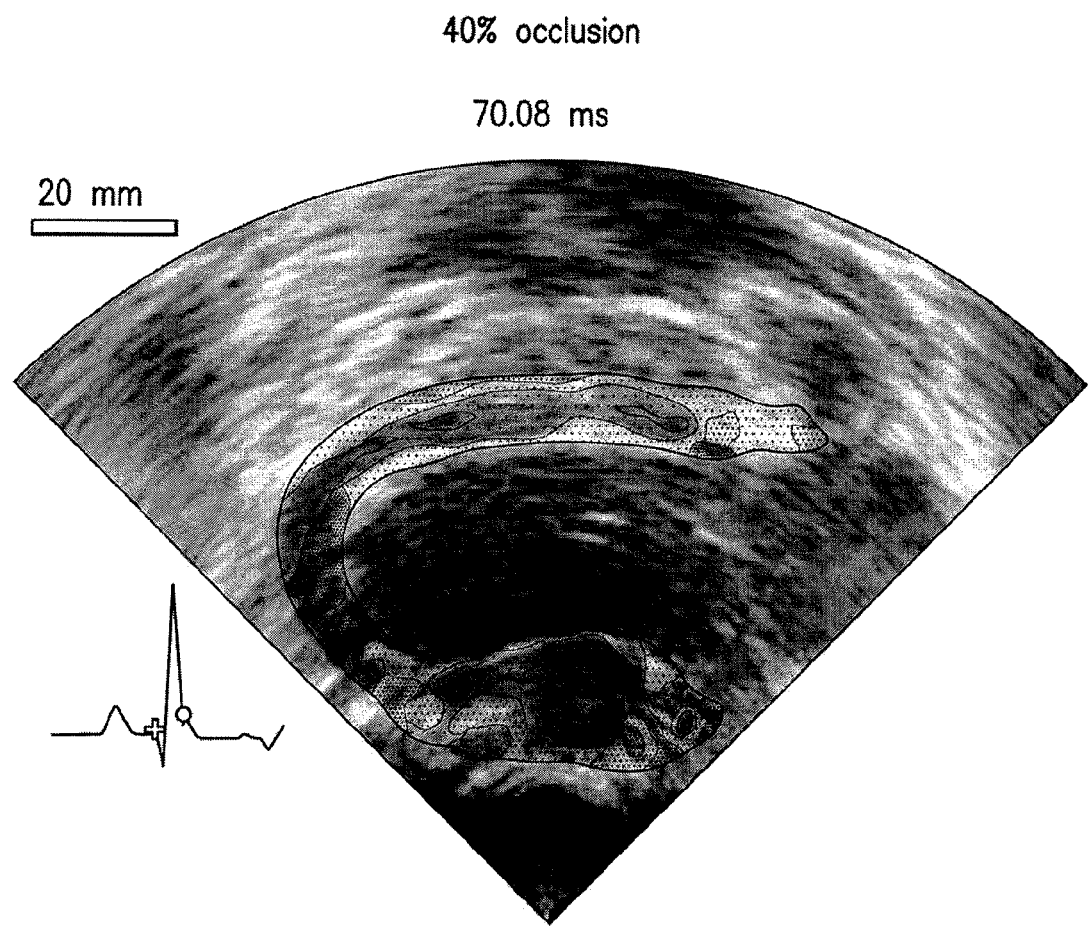
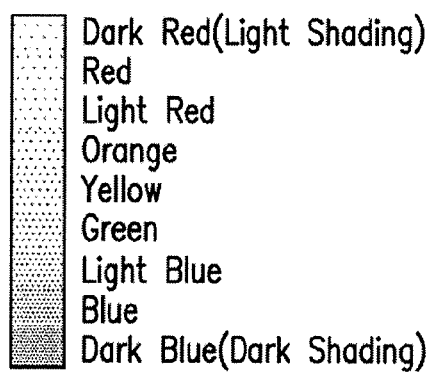
FIG.10(c)

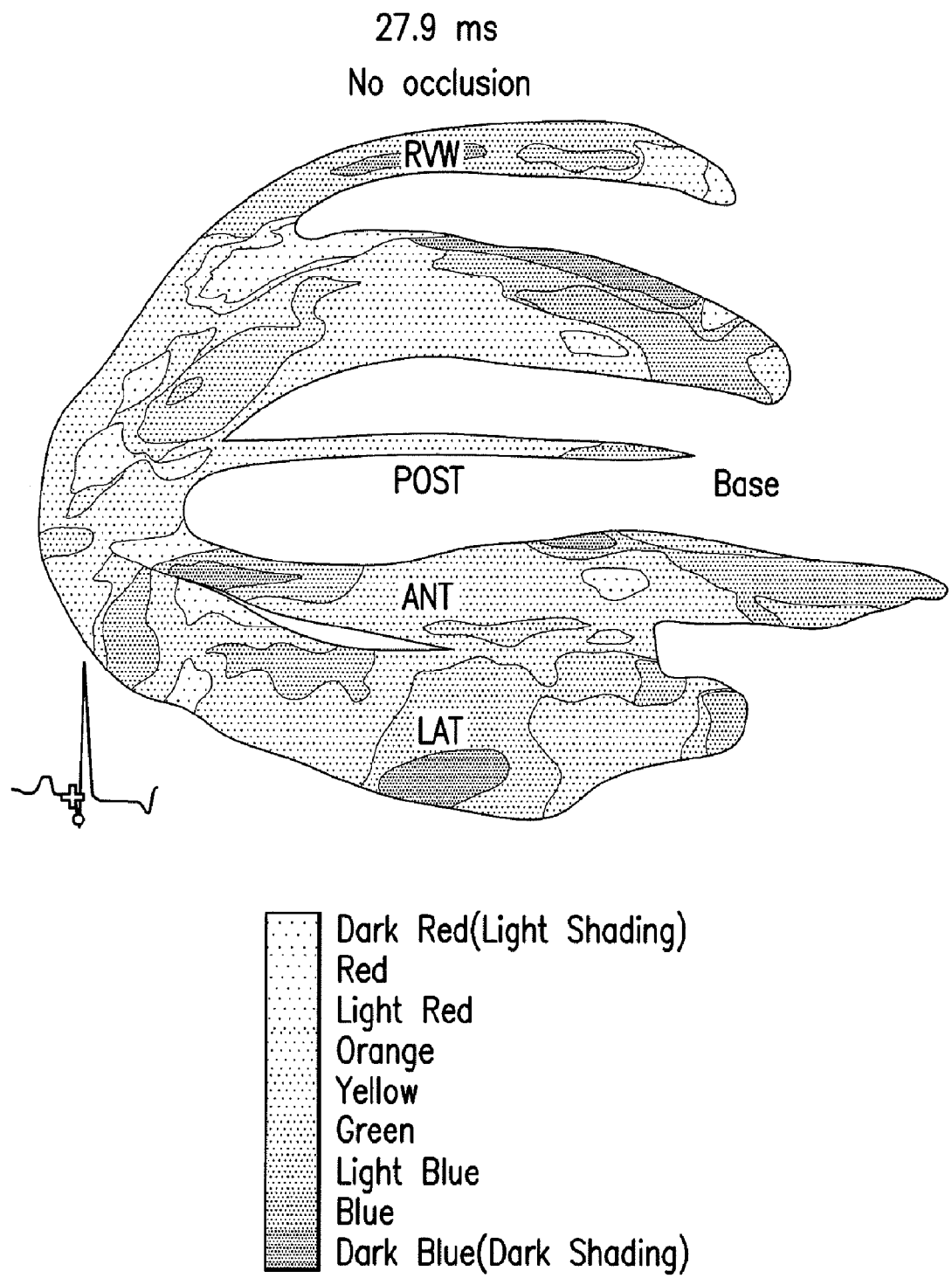
FIG.11(a)1

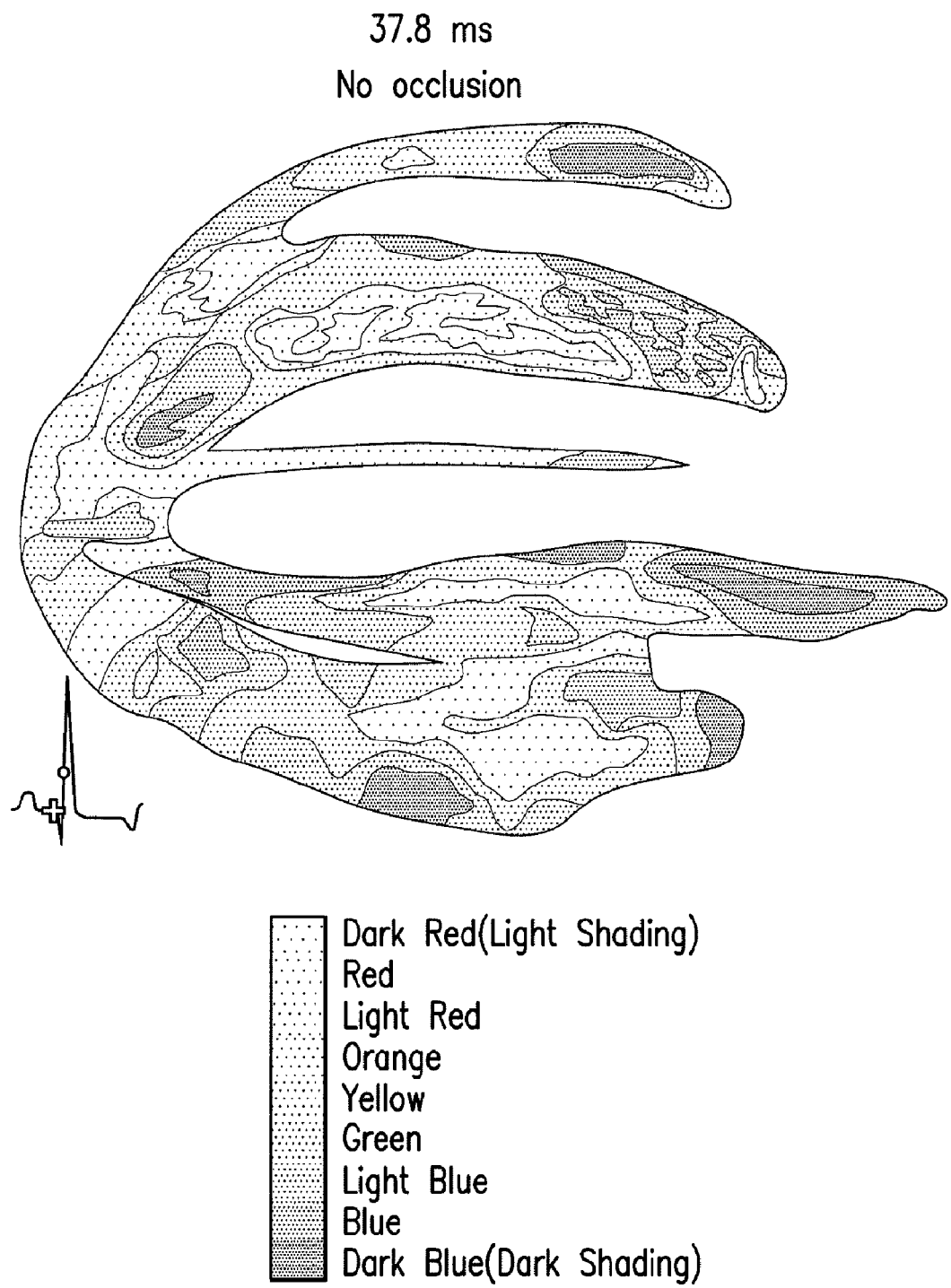
FIG.11(a)2

49.5 ms
No occlusion
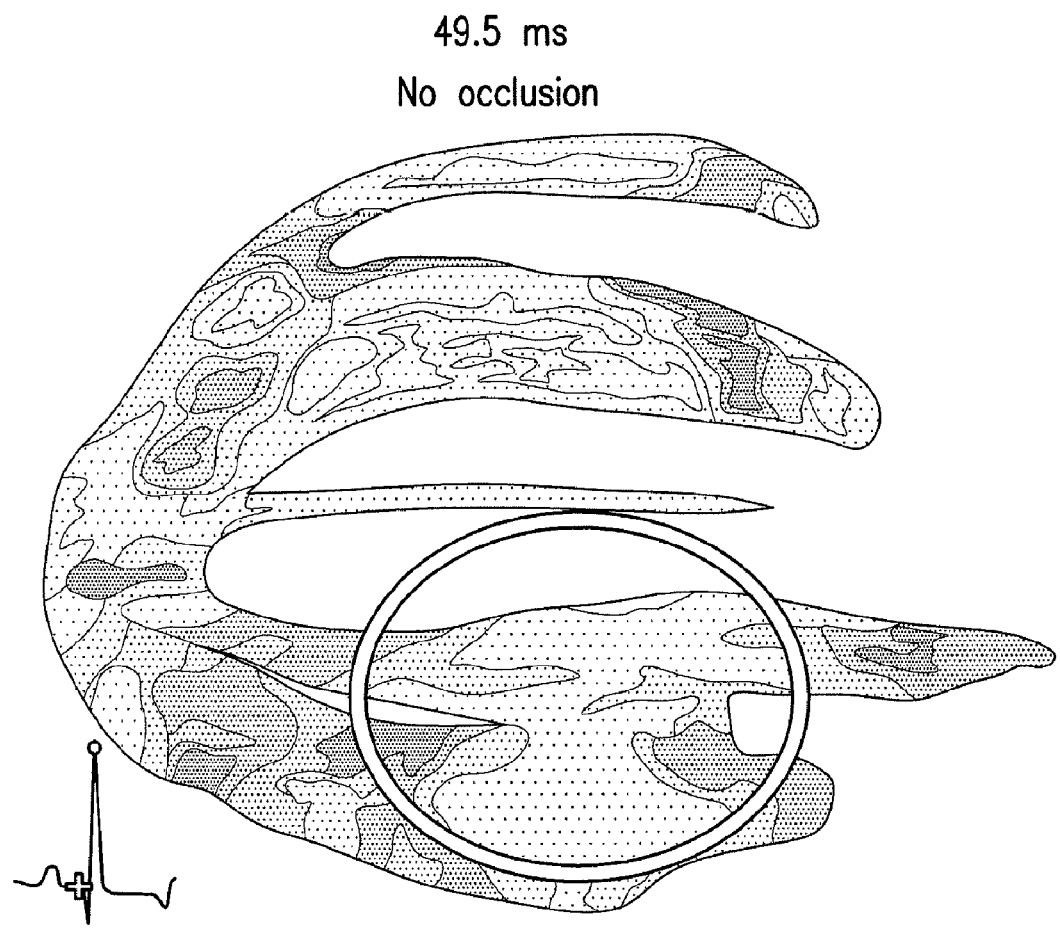
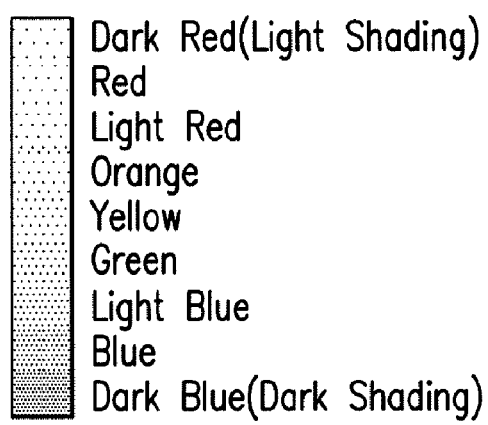
Dark Red (Light Shading)
Red
Light Red
Orange
Yellow
Green
Light Blue
Blue
Dark Blue (Dark Shading)
FIG.11(a)3

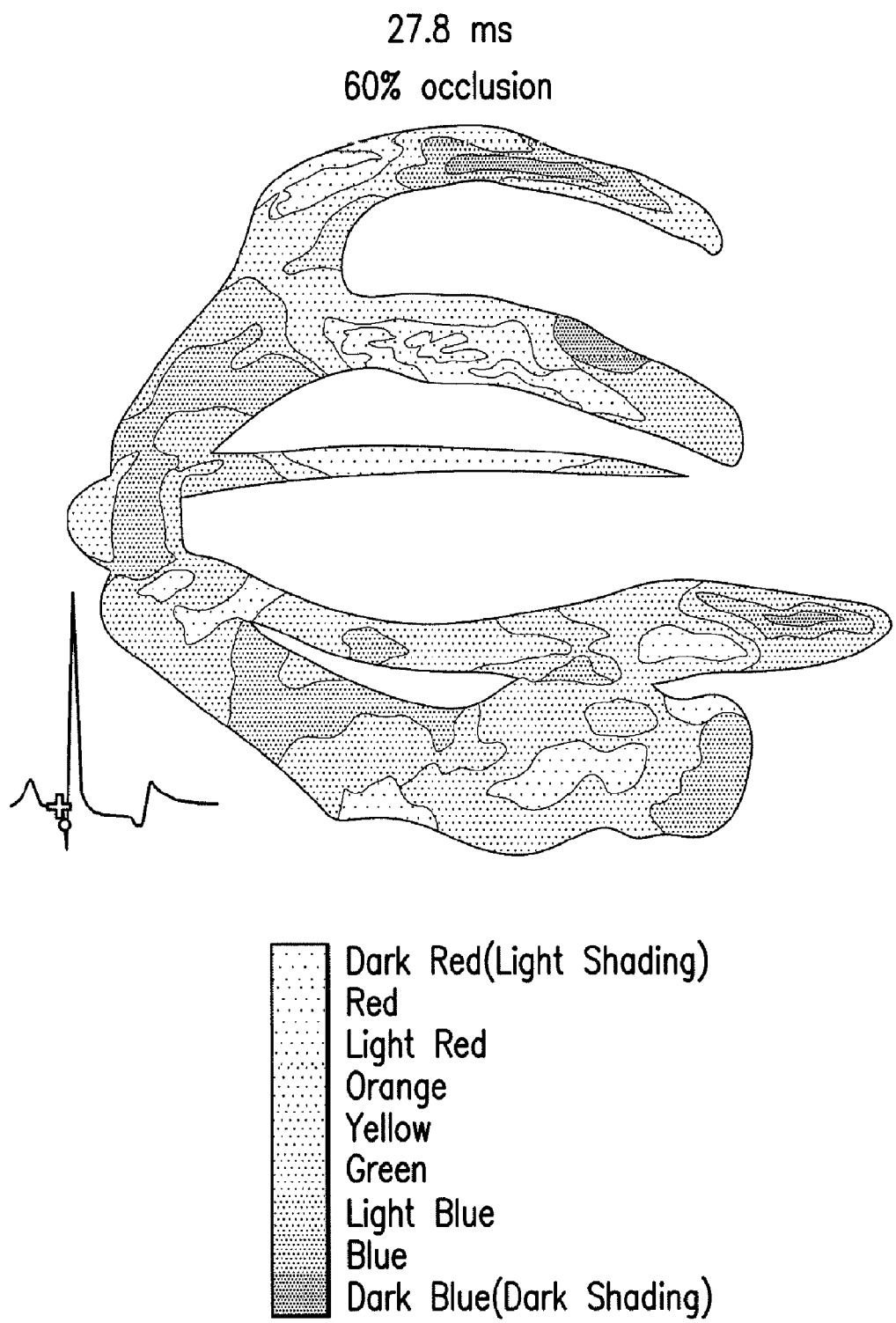
FIG.11(b)1

37.7 ms
60% occlusion
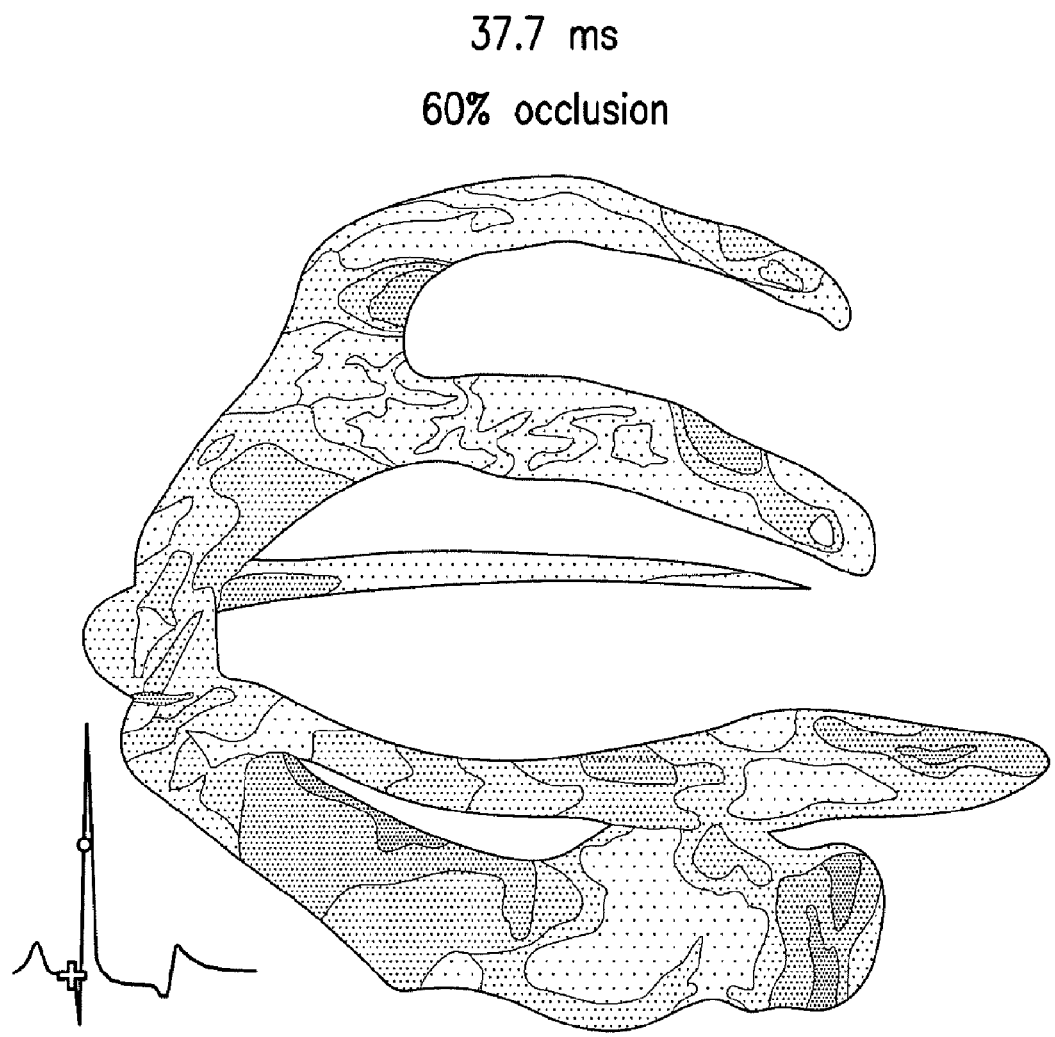
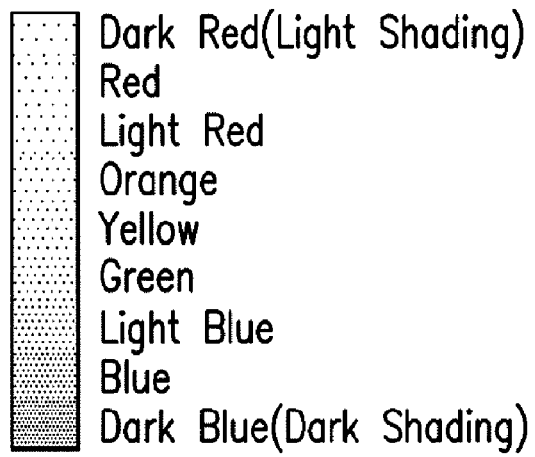
Dark Red (Light Shading)
Red
Light Red
Orange
Yellow
Green
Light Blue
Blue
Dark Blue (Dark Shading)
FIG.11(b)2

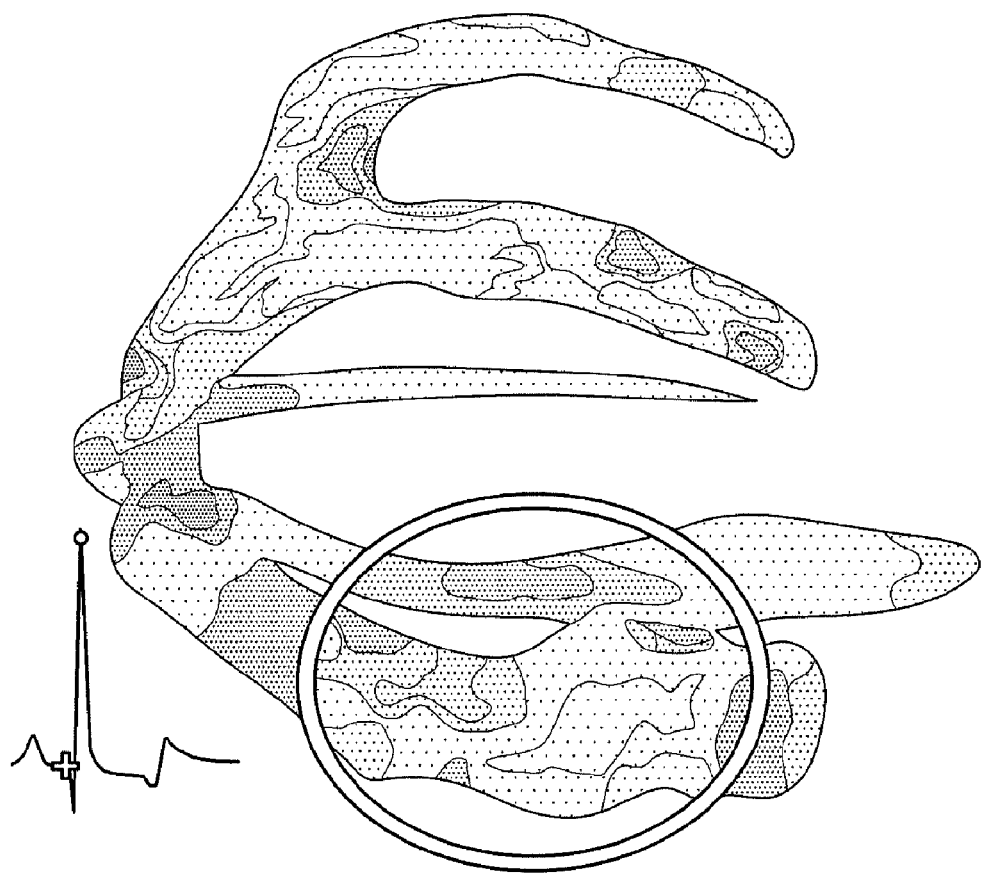
49.6 ms
60% occlusion
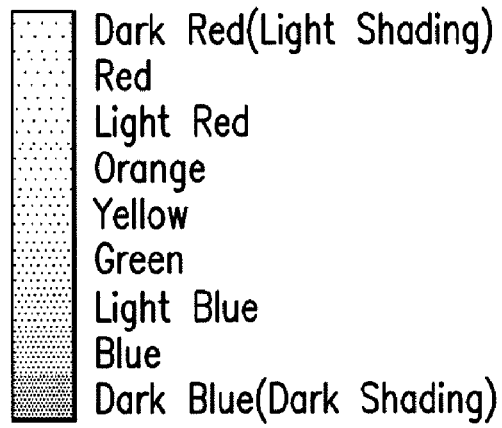
Dark Red (Light Shading)
Red
Light Red
Orange
Yellow
Green
Light Blue
Blue
Dark Blue (Dark Shading)
FIG.11(b)3

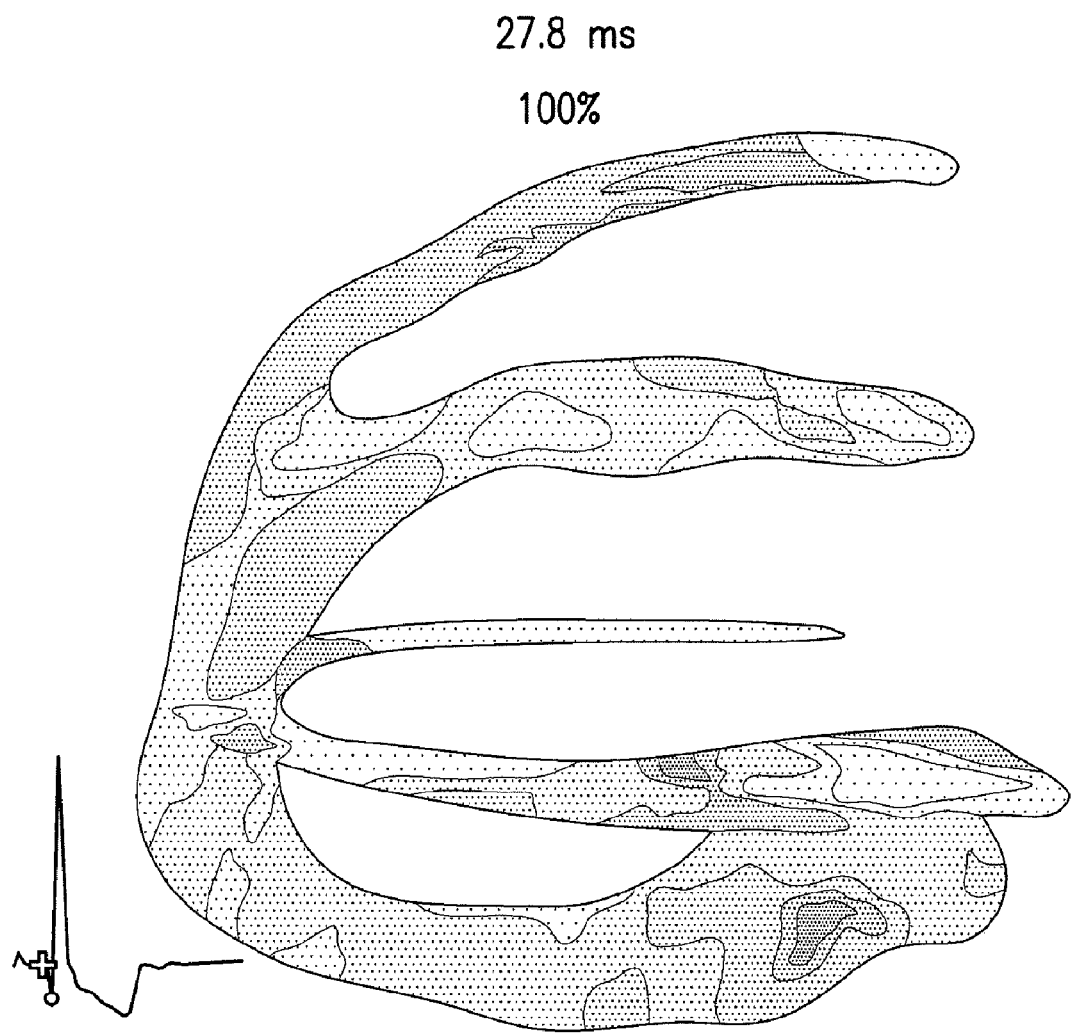
27.8 ms
100%
Dark Red(Light Shading)
Red
Light Red
Orange
Yellow
Green
Light Blue
Blue
Dark Blue(Dark Shading)
FIG.11(c)1

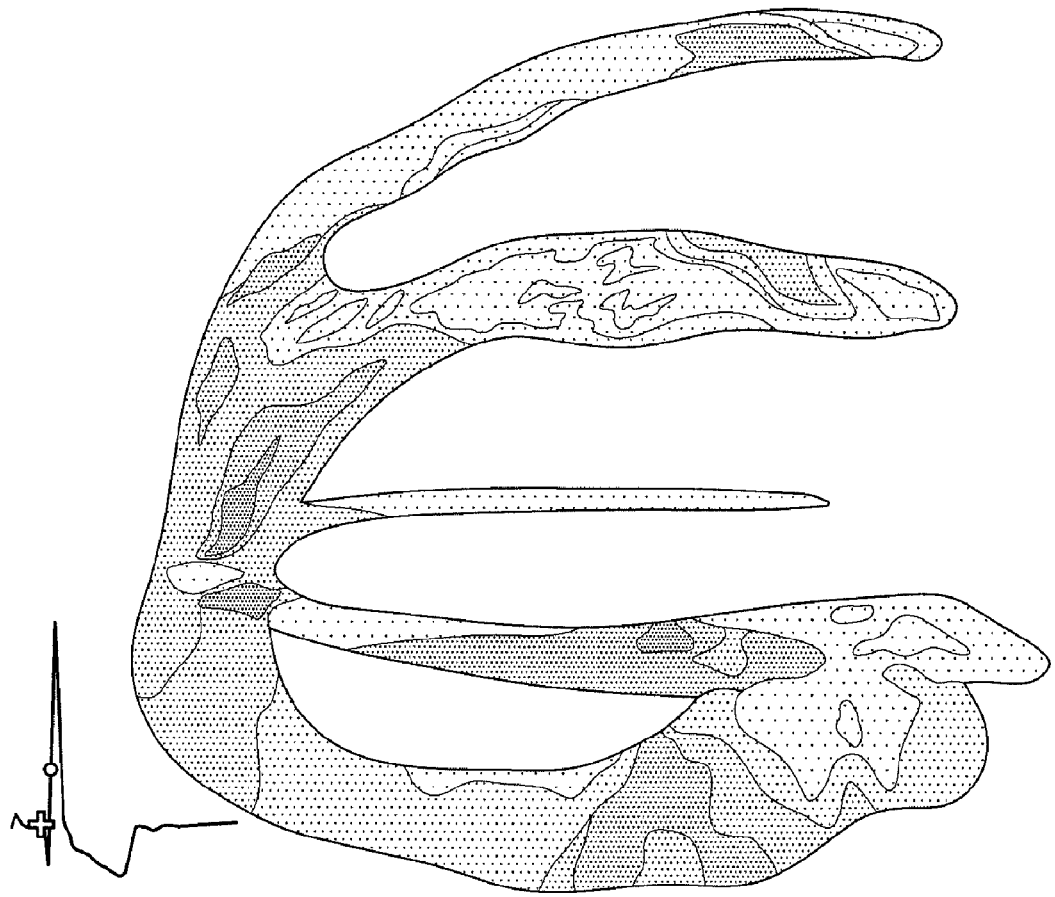
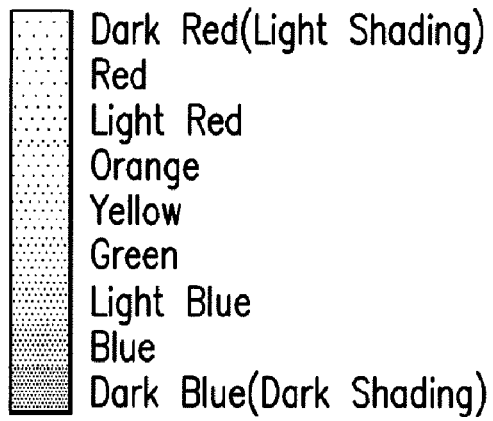
FIG.11(c)2

49.5 ms
100%
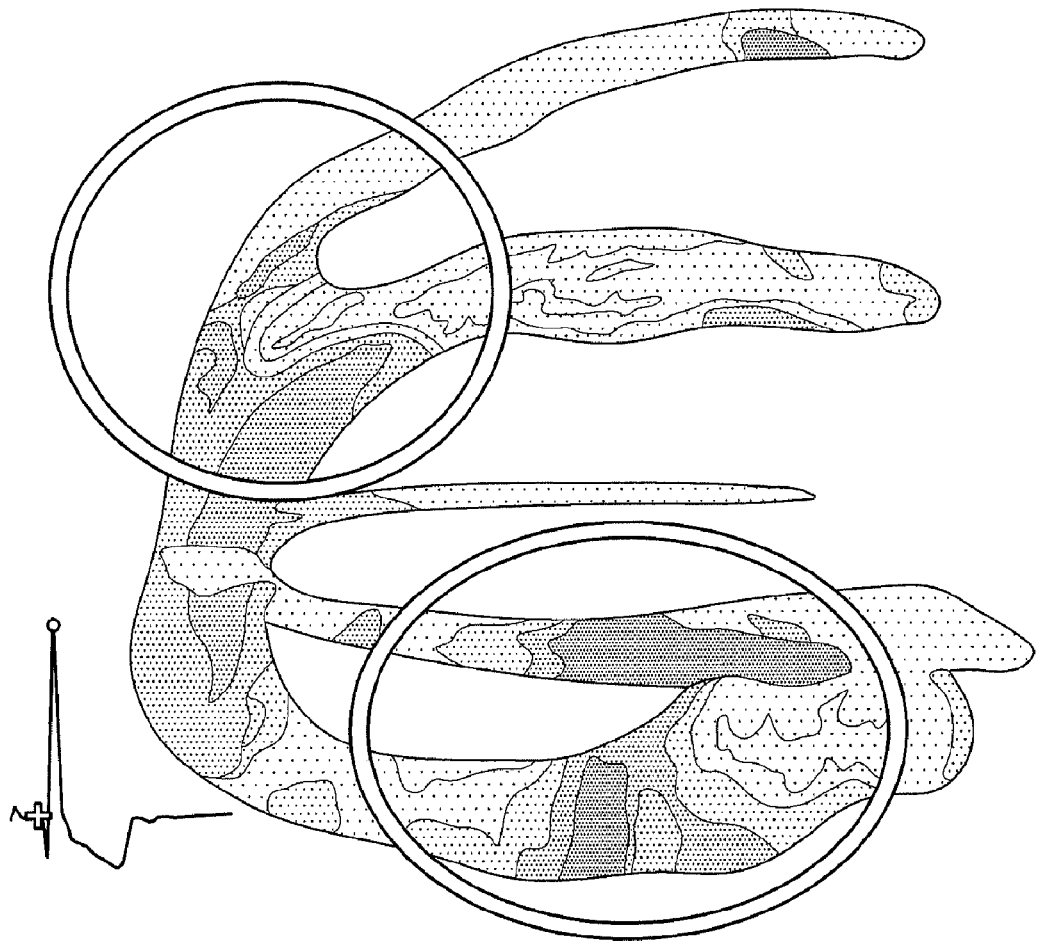
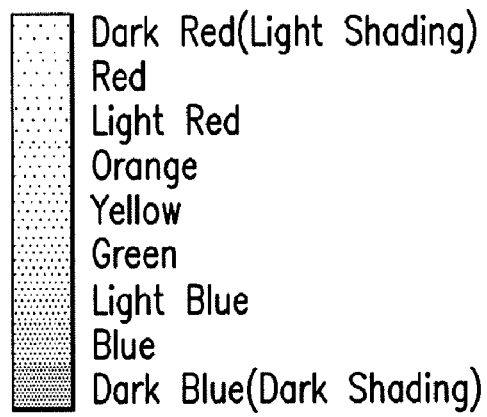
FIG.11(c)3

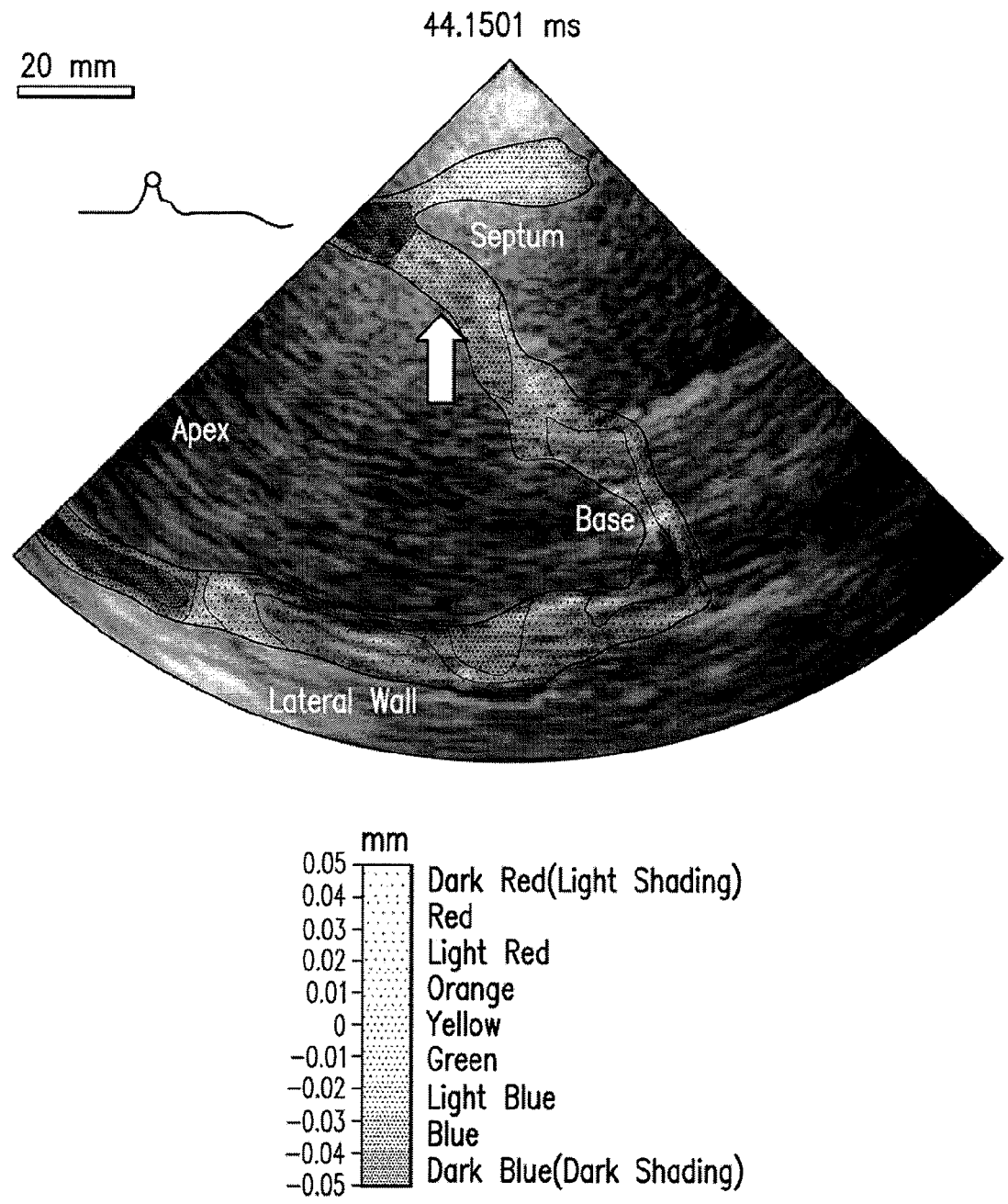
FIG.14(a)1

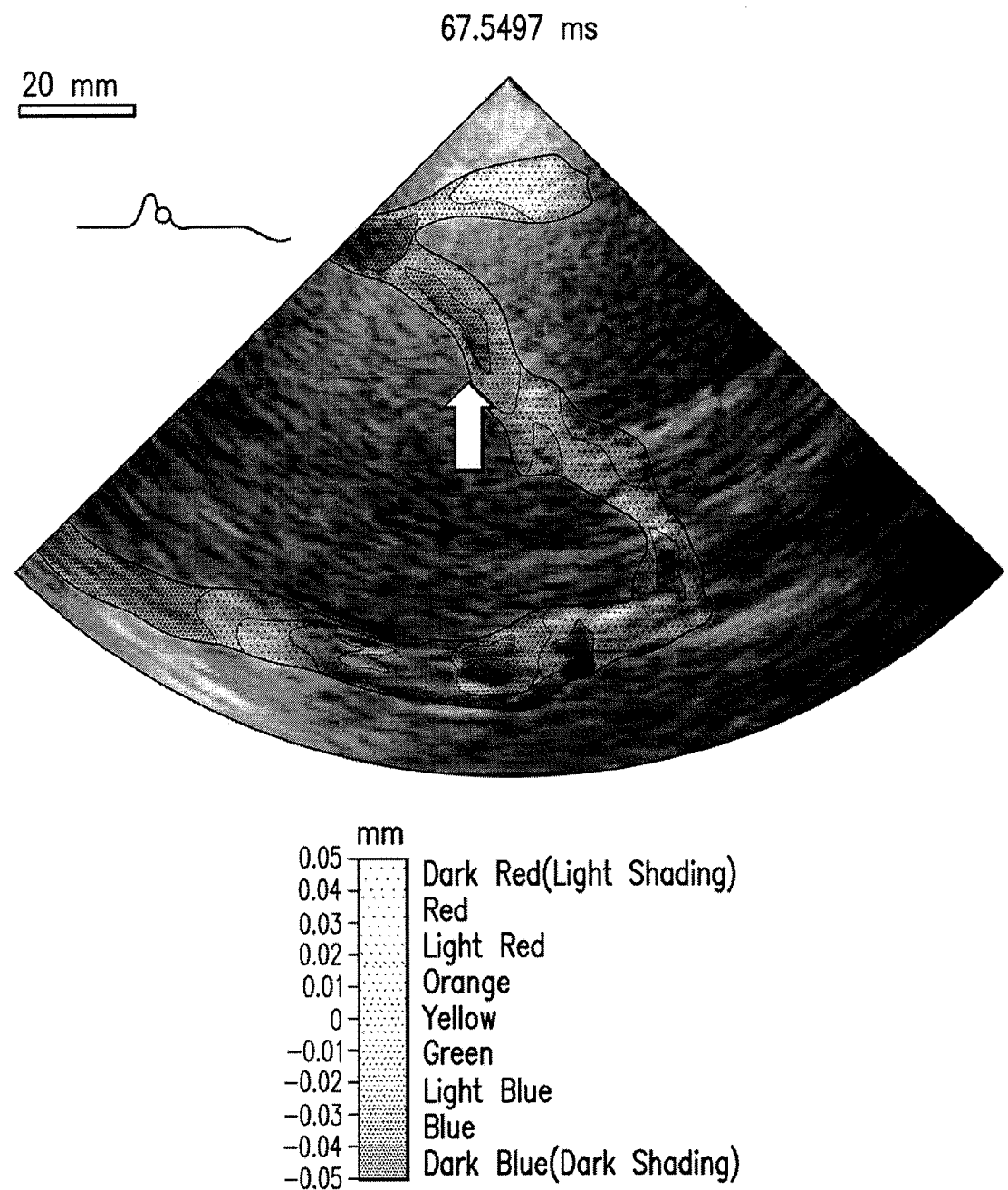
FIG.14(a)2

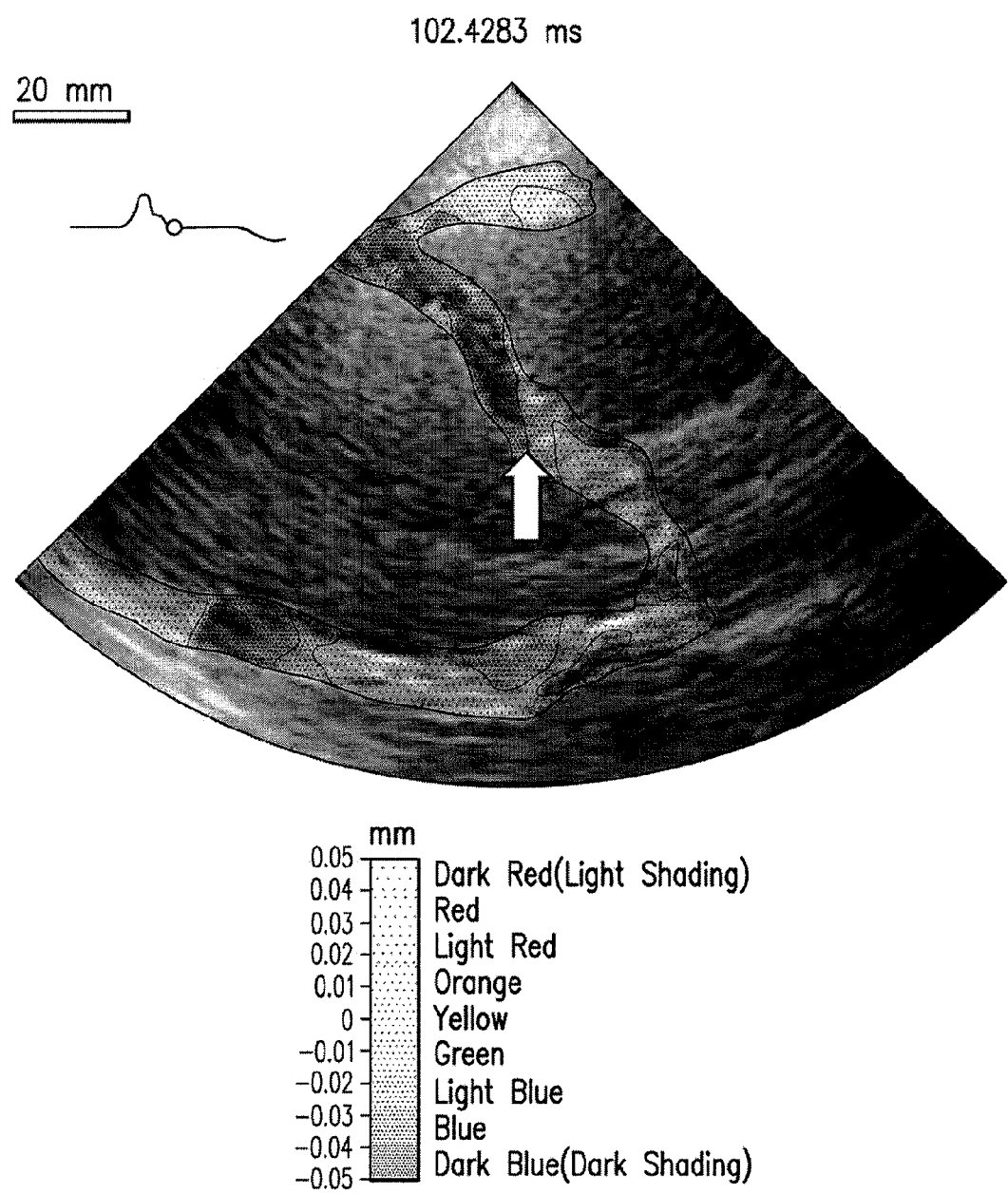
FIG.14(a)3

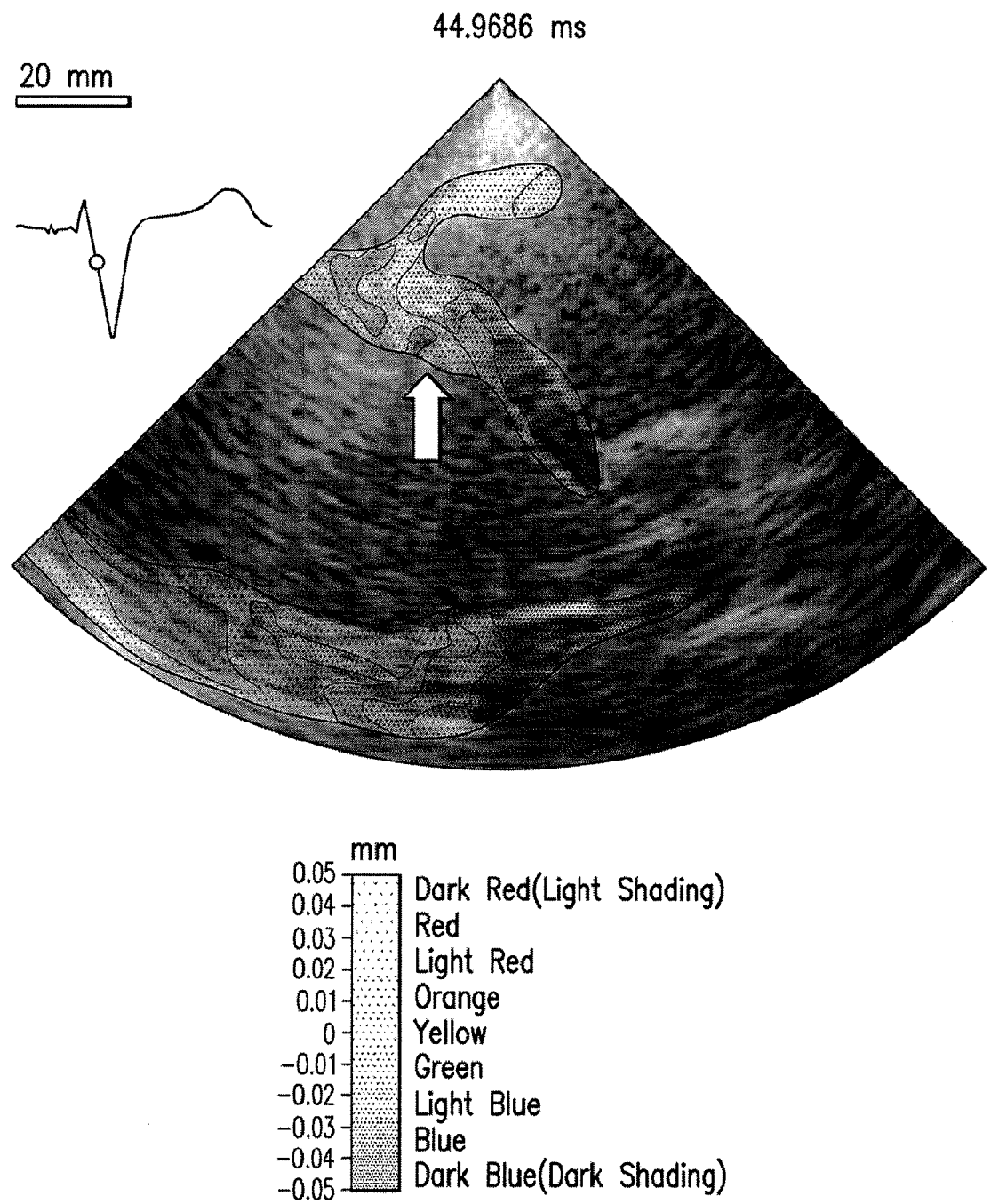
FIG.14(b)1

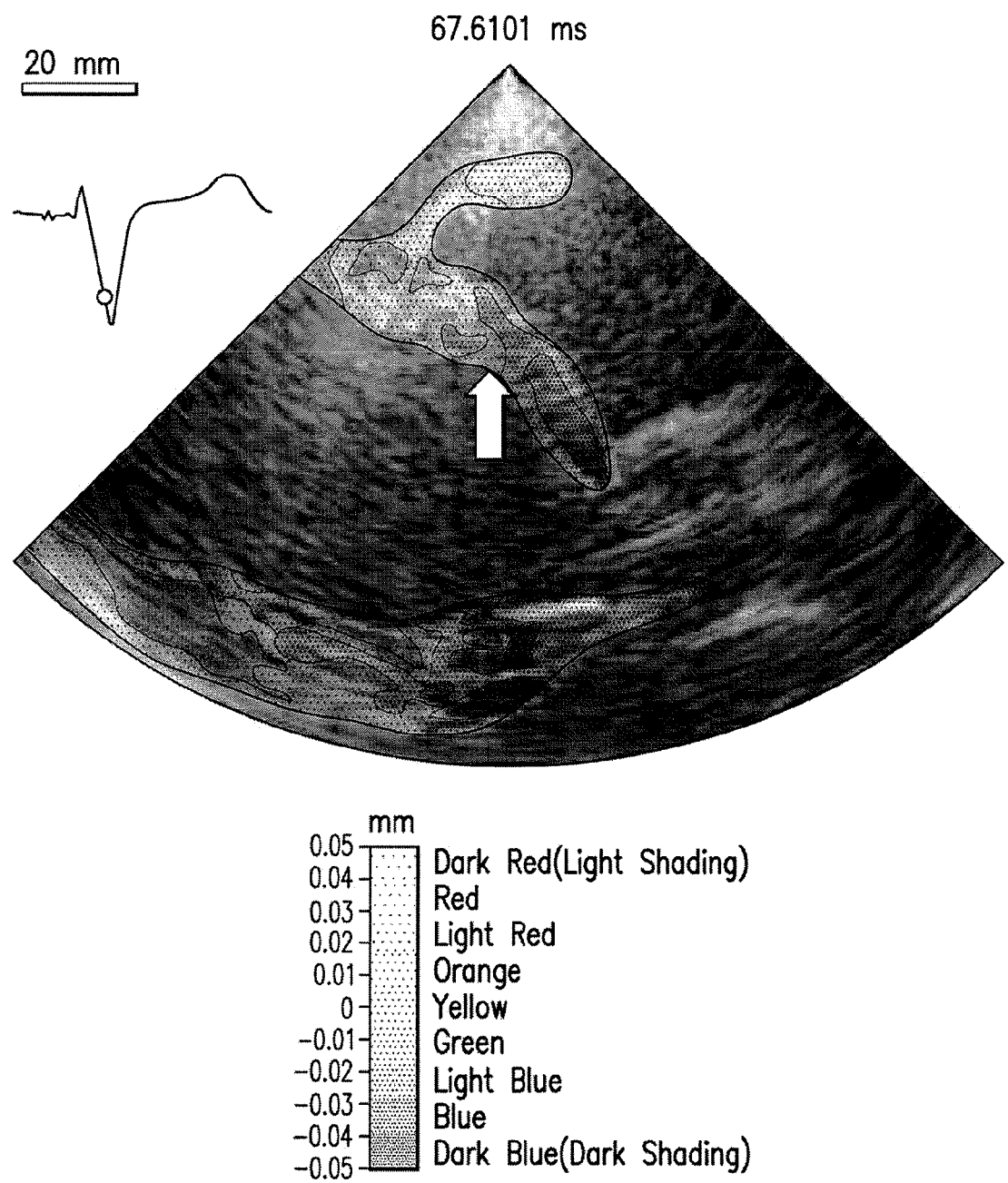
FIG.14(b)2

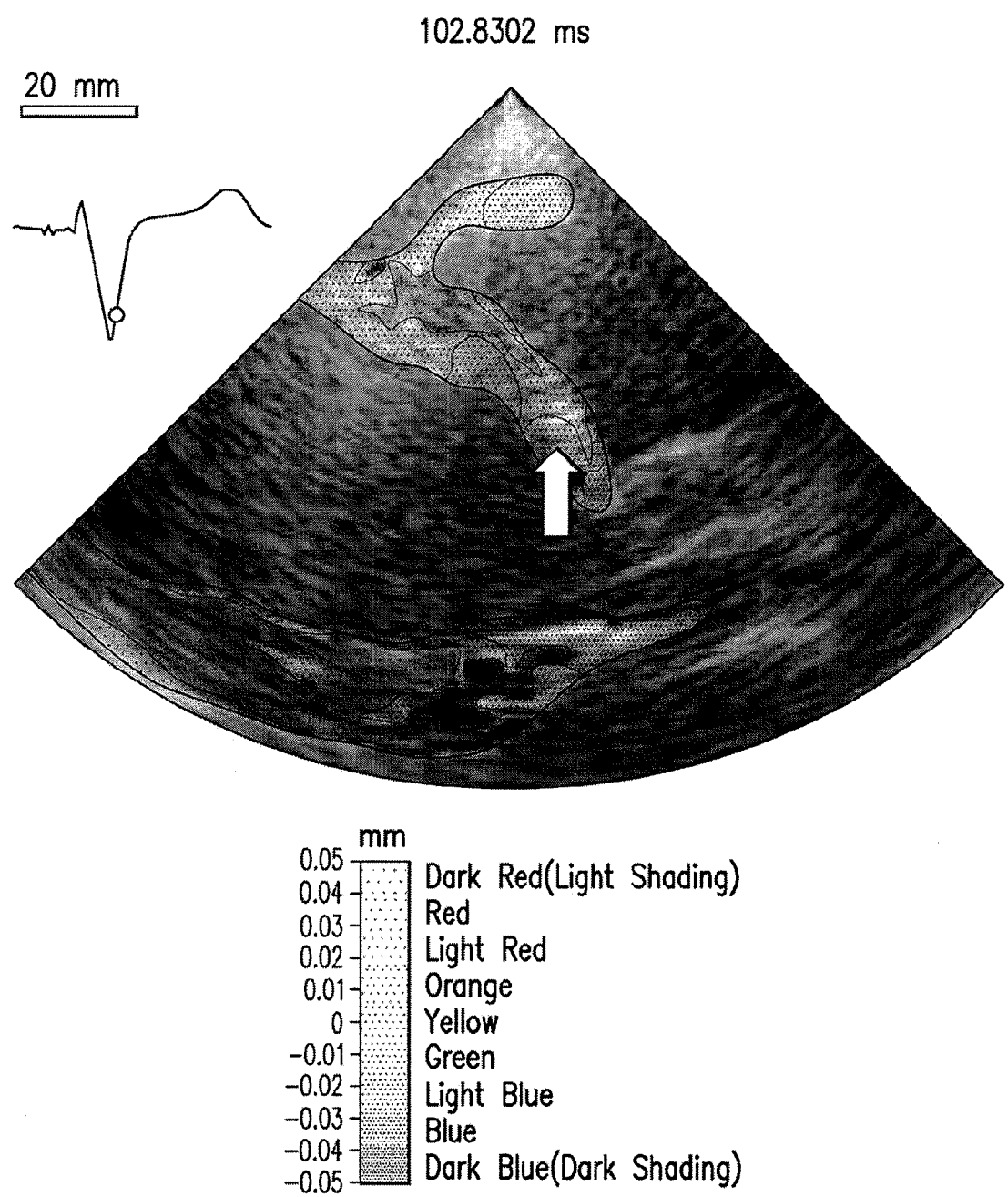
FIG.14(b)3

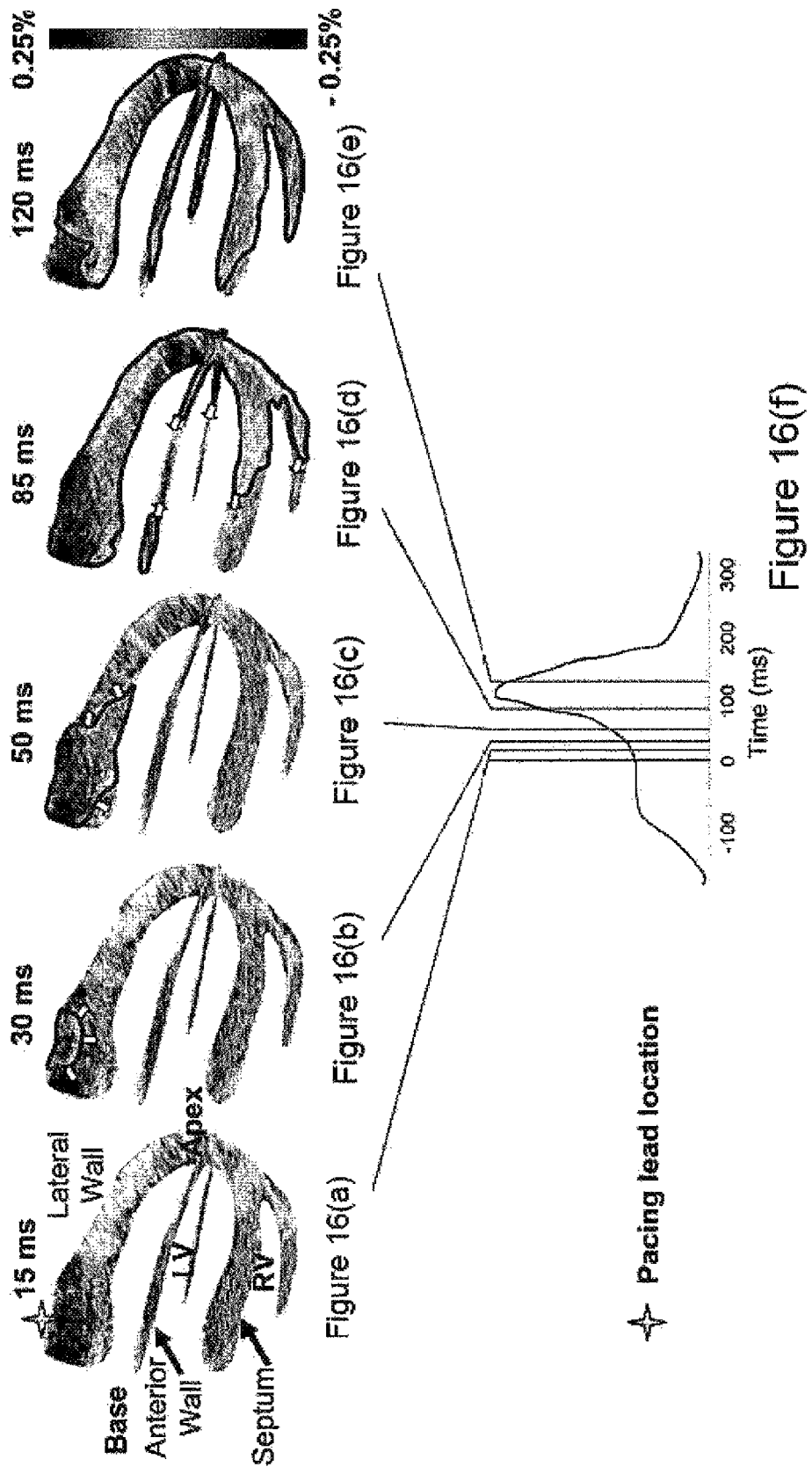

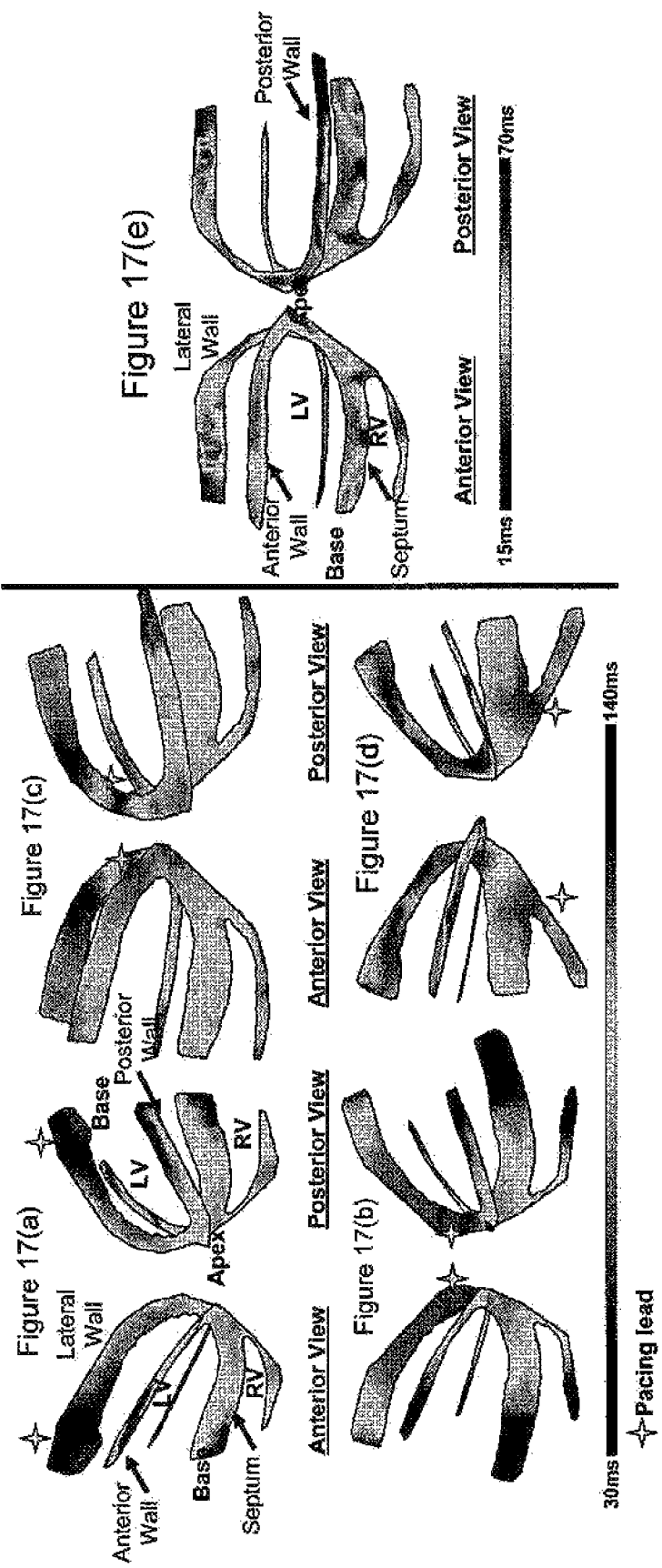

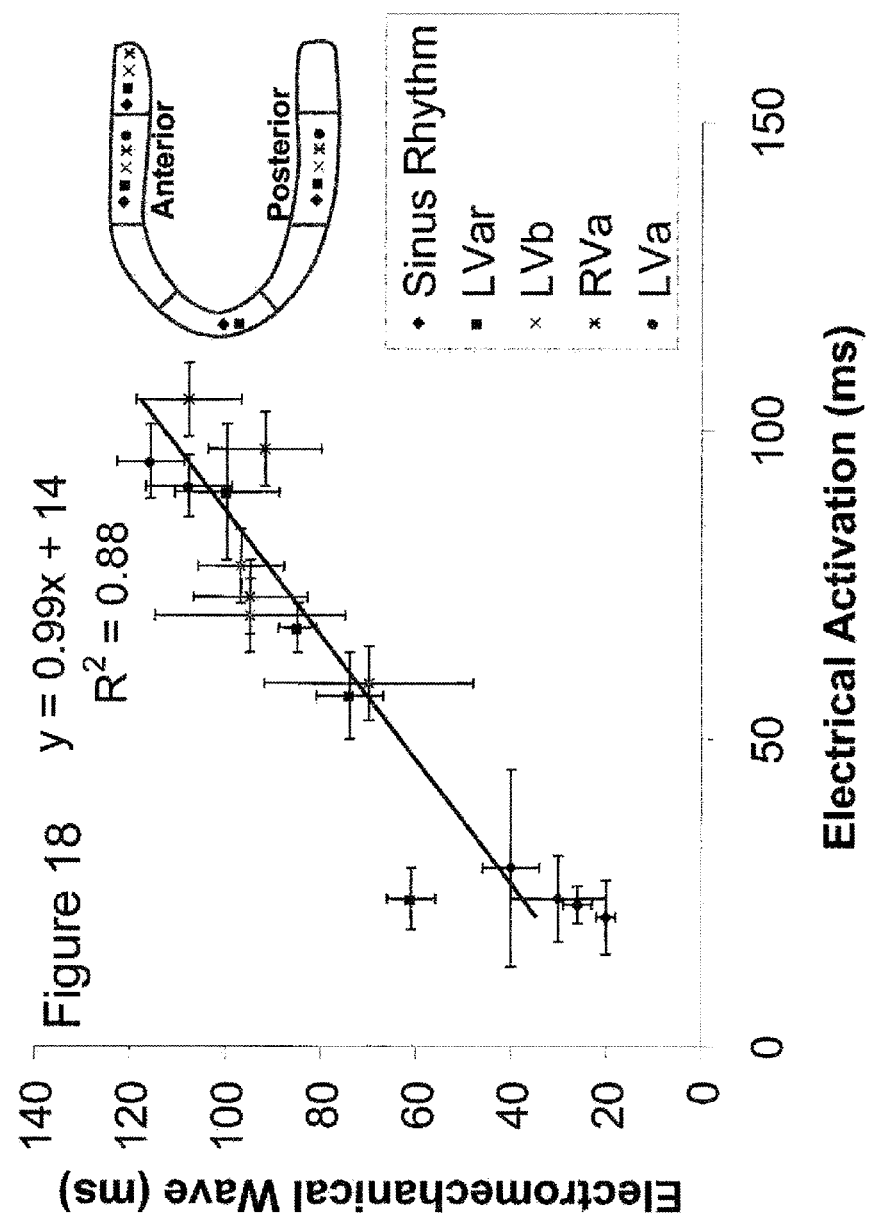

SYSTEMS AND METHODS FOR MATCHING AND IMAGING TISSUE CHARACTERISTICS

CROSS REFERENCE TO RELATED APPLICATIONS

This application is a continuation application of U.S. application Ser. No. 13/019,029, filed on Feb. 1, 2011, which is a continuation-in-part of International Application Serial No. PCT/US09/052563 entitled "Systems and Methods for Matching and Imaging Tissue Characteristics", filed on Aug. 3, 2009, which claims priority to U.S. Provisional Application No. 61/085,709 entitled "Motion Matching for Imaging and Estimation of Tissue Displacement", filed on Aug. 1, 2008, U.S. Provisional Application No. 61/086,112 entitled "Elastocardiography System for Automated Detection of Medical Conditions in a Subject", filed on Aug. 4, 2008, and U.S. Provisional Application No. 61/108,470 entitled "Electromechanical Wave Imaging for Detection of Ischemia", filed on Oct. 24, 2008, each of which are incorporated by reference in their entireties herein and from which priority is claimed.

STATEMENT REGARDING FEDERALLY-SPONSORED RESEARCH

This invention was made with government support under R01. EB006042 and R21 HL096094 awarded by the National Institutes of Health. The government has certain rights in the invention.

BACKGROUND

1. Field

The present application relates to systems and methods for anatomical and functional matching and imaging of tissue characteristics.

2. Background Art

Electrical mapping of the heart has emerged as an important tool for treatment monitoring of arrhythmias such as ventricular tachycardia. The map of local timings of electrical activation in the ventricle can identify abnormally conducting regions and guide radio frequency (RF) ablation treatments. Currently available clinical mapping systems are, however, invasive, since they require catheterization for introduction into the heart chamber. Therefore, electrical mapping cannot be performed for early detection of diseases or follow-up of chronic diseases such as heart failure.

Electromechanical Wave Imaging (EWI) has recently been introduced as a non-invasive, inexpensive, ultrasound-based modality, which can potentially map the electrical activation of the heart transmurally along various echocardiographic planes. This imaging modality is based on the measurement of small, transient deformations occurring in the myocardium a few milliseconds after, but following similar patterns as, the electrical activation. More specifically, after the action potentials reach the myocytes, the latter undergo depolarization followed by an uptake of calcium, which triggers contraction a few milliseconds later. Therefore, by measuring the onset of this contraction, the activation pattern across the entire myocardium can be mapped.

Over the past two decades, several methods have been developed for measuring deformations using ultrasound-based methods. Two-dimensional speckle-tracking-based motion estimation techniques have been implemented on clinical systems. Different approaches based on B-Mode or radio-frequency (RF) speckle tracking, or phase-tracking techniques have also been proposed in the literature for myocardial contractility assessment. Recently, open architecture ultrasound systems enabled motion estimation at very high effective RF-frame rates of standard echocardiographic views. The full view of the heart is divided into five to seven sectors acquired at very high frame rates and a full view ciné-loop is then reconstructed via electrocardiogram (ECG)-gating. Such high frame rates and the RF phase information increase the estimation quality and thus the reliability of two-dimensional displacement and strain mapping.

The increase in the frame rate did not only allow a better precision in the RF-based motion estimation, but also achieved a temporal resolution on the same time scale as that of the electrical propagation. More specifically, it allowed the detection of transient phenomena that occur during both isovolumic phases. For example, it was possible to identify the mechanical waves in the myocardial wall occurring when the valves open and close. Incremental displacements waves generated by the early contraction of myocytes, i.e., the Electromechanical Wave (EMW), have been depicted on EWI ciné-loop and images, and their correlation with the electrical activation velocity and pacing scheme have been verified. More recently, the EMW was reproduced in simulations and shown to be correlated with simulated and experimental electrical activation patterns.

Alternative methods for assessment of local electrical properties in vivo involve the use of electrode arrays, either by mounting an electrode sock around the heart through open-heart surgery to map the epicardial activation or by using electrode catheters. Newly developed non-invasive techniques based on heart models provided fully three-dimensional activation sequences. A method based on magnetic resonance (MR) tagging has also been proposed, where the subepicardial contraction sequence was mapped and compared to the electrical activation maps obtained with an epicardial electrode sock.

ECG-gating methods are common in biomedical imaging technologies to achieve frame-rate that are sufficient to obtain an accurate depiction of the cardiac motion either in two or three dimensions. It is useful, for instance, when imaging the heart or the cardiovascular system using computed tomography, magnetic resonance imaging, or nuclear imaging.

Though previous efforts have obtained high frame rates using ECG gating, for the analysis of diseases such as ventricular tachycardia, the ECG may not be regular. For example, when atrio-ventricular dissociation occurs, the atria and ventricles follow different rhythms, which may compromise the use of the ECG for co-registration of adjacent sectors. Accordingly, there is a need in the art for a non-invasive imaging technique that is not reliant on independent measurements of the electrical activity of the subject tissue.

SUMMARY

Systems and methods for matching a characteristic of multiple sectors of a moving tissue to verify an overlap thereof are disclosed herein. In an exemplary method, tissue data for at least a first sector and a second sector of a moving tissue is acquired. A characteristic of at least a portion of the first and second sectors is estimated from the acquired tissue data, and the estimated characteristics are matched to verify whether a portion of the first sector overlaps with a portion of the second sector. Estimating can include estimating a displacement such as an axial displacement and/or lateral displacements. Estimating can further include estimating a strain, a velocity, a strain rate and/or a stiffness or similar measures.

The method can further include determining a time delay between the matched characteristics, which can be utilized to form an image of the matched characteristic in at least the overlapping portion of the sectors.

In some embodiments, an image can be formed from a one-, two-, three-, or four-dimensional image of the target tissue. Further, in some embodiments, estimating the displacements of the target tissue can be performed using a speckle-tracking technique. A method in accordance with the disclosed subject matter can also include acquiring electrical activity data from the target tissue, and determining a correspondence between the electrical activity and the estimated characteristic of the sectors.

An exemplary system for matching a characteristic of multiple sectors of a moving tissue to verify an overlap thereof in accordance with the disclosed subject matter includes a computer readable medium storing program instructions, and a processor adapted to receive tissue data for at least a first sector and a second sector of a moving tissue. The processor is operatively connected to the computer readable medium and configured to execute the stored program instructions, and is further configured such that upon execution of the stored program instructions, the processor estimates a characteristic of at least a portion of the first and second sectors from the acquired data, and matches the estimated characteristics. The processor can further determine a time delay between the matched characteristics, and form an image of the matched characteristics in at least the overlapping portion of the sectors utilizing the determined time delay.

A system in accordance with the disclosed subject matter can further include a data acquisition device for acquiring data from two or more sectors of the tissue. The data acquisition device can be an ultrasound device and can be capable of acquiring frames of data a rate of at least 50 to 10000 frames per second. The data acquisition device can also be another imaging modality, such as an MRI or CT device. The system can further include an electrical detection device configured to detect an electrical signal propagating through the tissue, which can be an electrocardiographic device.

BRIEF DESCRIPTION OF THE DRAWINGS

The accompanying drawings, which are incorporated and constitute part of this disclosure, illustrate some embodiments of the disclosed subject matter.

FIG. 7(a)1-FIG. 7(a)6 illustrates the propagation of incremental displacement in the four-chamber view over six image frames generated in accordance with an exemplary embodiment of the disclosed subject matter.

FIG. 7(b)1-FIG. 7(b)6 illustrates 2D strain images corresponding to the incremental displacement images of FIG. 7(a) generated in accordance with an exemplary embodiment of the disclosed subject matter.

FIG. 8-1-FIG. 8-9 illustrates 2D strain images of electromechanical wave propagation in a normal heart under sinus rhythm in the parasternal two-chamber view in accordance with an exemplary embodiment of the disclosed subject matter.

FIG. 9-1-FIG. 9-4 illustrates isochrones of the two different dogs in the two- and four-chamber view showing the time of arrival of the electromechanical wave in accordance with an exemplary embodiment of the disclosed subject matter.

FIG. 10(a)-(f) show the evolution of the electromechanical wave with different levels of ischemia in accordance with an exemplary embodiment of the disclosed subject matter.

FIG. 11(a)1-FIG. 11(c)3 illustrate a bi-plane view of a heart under different left anterior descending coronary artery occlusion levels in accordance with an exemplary embodiment of the disclosed subject matter.

FIG. 14(a)1-FIG. 14(b)3 illustrate electromechanical wave imaging of a patient undergoing cardiac resynchronization therapy in accordance with an exemplary embodiment of the disclosed subject matter.

FIGS. 16(*a*)-(*e*) illustrate the propagation of the electromechanical wave from a pacing lead location in the basal region of the lateral wall in accordance with an exemplary embodiment of the disclosed subject matter.

FIG. 16(*f*) illustrates the activation of the electrocardiogram as the electromechanical wave propagates in accordance with an exemplary embodiment of the disclosed subject matter.

FIGS. 17(*a*)-(*d*) illustrate isochronal maps of four different pacing schemes in both anterior and posterior views in accordance with an exemplary embodiment of the disclosed subject matter.

FIG. 17(*e*) illustrates an isochronal map in both anterior and posterior views during sinus rhythm in accordance with an exemplary embodiment of the disclosed subject matter.

FIG. 18 illustrates the electromechanical wave onset time versus the time of electrical activation for five different pacing schemes in accordance with an exemplary embodiment of the disclosed subject matter.

FIG. 19(*b*) illustrates the corresponding isochronal representation of the electromechnical wave in FIG. 19(*a*) in accordance with an exemplary embodiment of the disclosed subject matter.

DETAILED DESCRIPTION

The systems and methods described herein are useful for matching a characteristic of a moving tissue in two or more sectors of the tissue and imaging the same. Although the description is focused on the example of myocardial tissue analysis, the systems and methods herein are useful for motion-matching in other tissues, such as the aorta or the liver.

The techniques described herein makes use of data acquisition equipment, e.g., ultrasound, MRI, CT, or other imaging devices, to acquire motion data in multiple sectors of a tissue undergoing periodic motion, e.g., motion data of a heart during the cardiac cycle. That data is then reconstructed into one-, two-, three or four-dimensional images by matching up the data in overlapping areas of the sectors and further by accounting for the time delay between the data acquired in different sectors. By utilizing such a technique the systems and methods described herein can be used to produce a composite image of the tissue.

Figure 1:
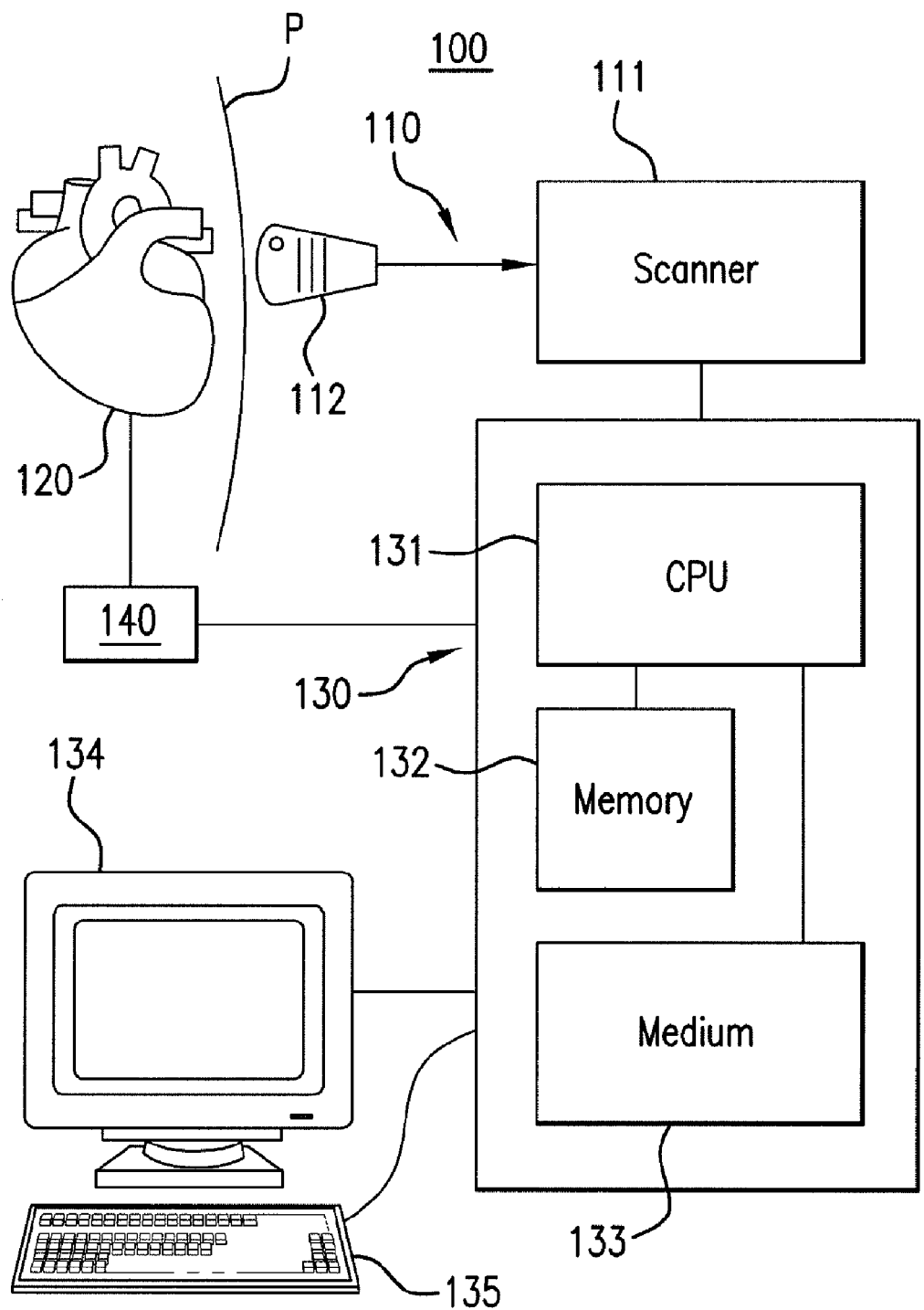
FIG. 1 illustrates a system for imaging the displacement of tissue in accordance with an exemplary embodiment of the disclosed subject matter.

FIG. 1 illustrates a system 100 for matching a characteristic of two or more sectors of a moving tissue to verify whether any portions thereof overlap in accordance with an exemplary embodiment of the disclosed subject matter. The system 100 can comprise a data acquisition device 110, e.g., an ultrasound, MRI, CT or other device, for acquiring tissue data for at least a first sector and a second sector of said moving tissue 120, e.g., a heart, liver, blood, or other tissue. The tissue 120 can be separated into two or more sectors 1, 2 such that each sector shares an overlapping portion 3 with another sector (illustrated in FIG. 3(*a*)). The overlapping portion 3 does not need to be contiguous with other portions of sectors 1, 2. In one embodiment, tissue 120 can be divided into five to seven sectors. FIG. 1 illustrates an exemplary embodiment wherein the characteristic matching is conducted on a patient P non-invasively. Specific examples discussed below were performed on open-chested dogs and on humans in vivo.

The data acquisition device 110 can be composed of a scanner 111 and a probe 112, as is understood in the art and discussed in U.S. patent application Ser. No. 11/433,510, the entire contents of which is incorporated by reference herein. Further, in exemplary embodiments involving myocardial tissue the data acquisition device 110 can be capable of acquiring data at a sufficiently high rate such that it can capture an electromechanical wave propagation through the myocardial tissue. In one exemplary embodiment, the data acquisition device 110 can acquire data at a rate of at least 50 frames per second (fps). Preferably the data acquisition device 110 can acquire data at a rate of 1,000-10,000 fps. In one specific embodiment, the data acquisition device 110 is an Ultrasonix RP system with a 3.3 MHz phased array capable of acquiring image data at a rate from 390 to 520 fps. The data acquisition device 110 can also be configured to acquire data using an automatic composite technique, as discussed in Wang et al., "A composite high-frame-rate system for clinical cardiovascular imaging," Ultrasonics, Ferroelectrics and Frequency Control, IEEE Transaction on, vol. 55, 2008, pp. 2221-2233, which is incorporated by reference herein in its entirety. It is understood that a larger number (and hence smaller size) of sectors 1, 2 will directly contribute to an increase in the acquisition rate achievable by the data acquisition device 110 for a given tissue 120.

The image acquisition device 110 is operatively connected to a computer system 130 which is comprised of a processor 131 and a memory 132 operatively connected to the processor 131. The processor 131 is adapted to receive tissue data for at least the first and second sectors 1, 2 of the moving tissue 120. The computer system 130 also includes a computer readable medium 133, e.g., a hard disk drive, CD, etc., which is operatively coupled to the processor 131 and the memory 132. The computer readable medium 133 stores program instructions to be executed by the processor 131, utilizing the memory 132, to estimate a characteristic of at least a portion of the first sector 1 and a characteristic of at least a portion of the second sector 2. The processor 131 further executes the stored program instructions to match the estimated characteristic of the portion of the first sector 1 with the estimated characteristic of the portion of the second sector 2.

It will be understood by those skilled in the art that sectors 1, 2 can be chosen such that they share overlapping portion 3 prior to the execution of the program instructions by processor 131. The presently disclosed subject matter also envisions that sectors 1, 2 can be chosen without foreknowledge of the existence, location or particular dimensions of overlapping portion 3. In either scenario matching the portion of the sectors 1, 2 will verify whether those portions form overlapping portion 3.

The processor 131 can be further configured to determine a time delay between the matched characteristic of the portion of the first sector 1 and the matched characteristic of the portion of the second sector 2. The processor 131 can utilize the time delay determination to form an image of the matched characteristic of the portion of the first sector 1 and the matched characteristic of the portion of the second sector 2.

The same or a different computer readable medium 133 can be used to store the image of the matched characteristic of tissue 120 and further can be used to store the acquired data. The computer system 130 can further be comprised of a visual display unit 134, e.g., a computer monitor, for displaying the composite image, and the series of images if desired. The computer system 130 can also be connected to input device 114, e.g., a keyboard.

The computer system 130 can be any standard desktop computer or other suitable computing system. In one embodiment, for example in connection with the below described experiment, the computer system 130 is a 120-node Linux cluster, each node composed of two AMD Operon Model 2222 CPUs (two cores per CPU), 8 GB RAM, and a 160 GB SATA hard disk drive operating at 7200 RPM.

The system 100 can further be comprised of an electrical detection device 140, e.g., an electrocardiographic device (ECG). As illustrated in FIG. 1, the electrical detection device 140 can be connected to the tissue 120 to measure the electrical activity therein. The electrical detection device 140 can be further operatively connected to computer system 130, but could also be connected to a different computer system (not shown), if desired.

Figure 2:
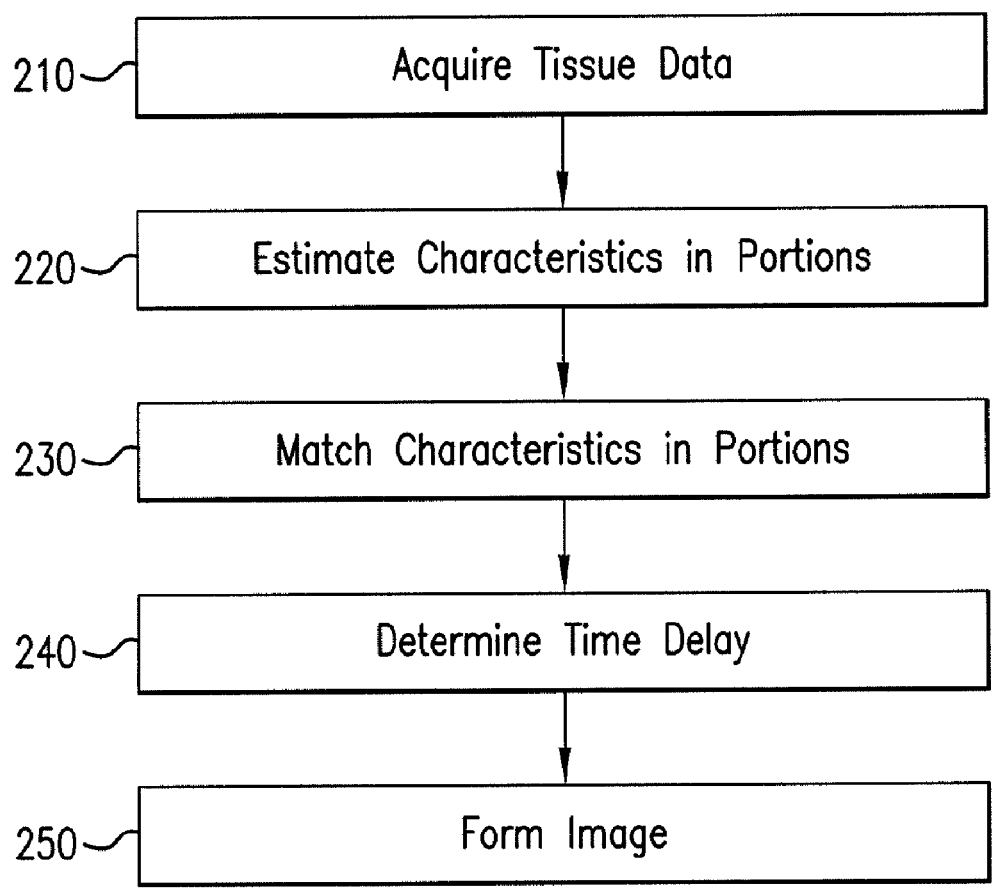
FIG. 2 illustrates a method for imaging the displacement of tissue in accordance with an exemplary embodiment of the disclosed subject matter.

FIG. 2 illustrates a method 200 for matching a characteristic of multiple sectors 1, 2 of a moving tissue 120 in accordance with an exemplary embodiment of the disclosed subject matter. The method 200 comprises acquiring 210 tissue data for at least a first sector 1 and a second sector 2 of the moving tissue 120, e.g., a heart, aorta, liver, blood or other tissue. The acquired data 210 can be acquired by a data acquisition device 110, e.g., an ultrasound, MRI, CT or other device capable of acquiring tissue data. As discussed above, the tissue data can be acquired 210 at a rate of 50-10,000 fps.

The method 200 further comprises estimating 220 a characteristic of at least a portion of the first sector 1 and a characteristic of at least a portion of the second sector 2 from the acquired tissue data. The estimated characteristic of the portion of the first sector 1 and the portion of the second sector 2 are matched 230. As discussed above, the matching 230 verifies whether the portion of the first sector 1 and the portion of the second sector 2 comprise overlapping portion 3.

Also as noted above, skilled persons will understand the techniques described herein are useful whether sectors 1, 2 are chosen such that they share overlapping portion 3 or whether sectors 1, 2 are chosen without such foreknowledge. Further, the overlapping portion 3 does not have to be contiguous with other portions either of sectors 1, 2. In one exemplary embodiment, the target tissue 120 can be divided into five to seven sectors each sharing at least one overlapping portion 3 with another sector. In the same or another exemplary embodiment, the target tissue 120 was chosen to have five sectors, each comprised of 16 radio frequency (RF) lines (or "RF beams"), and the acquisition 210 was performed at 389 fps using an automatic composite imaging technique. For each sector, approximately three heart cycles were recorded and three RF beams comprised the overlapping portions 3 shared by adjacent sectors. Thus, for this exemplary embodiment, the full-view image of target tissue 120 comprised of 65 RF lines.

In one embodiment, the estimation 220 comprises estimating a displacement. The estimation 220 can also comprise estimating a strain, a velocity, a strain rate, and/or a stiffness. Indeed, it is understood the disclosed subject matter can comprises estimating 220 other characteristics of tissue indicative of tissue motion. Further the estimation 220 can be performed for each sector 1, 2 using techniques well known in the art, e.g., a speckle-tracking technique. Where the characteristic estimated 220 is displacement, it can comprise axial and/or lateral displacement. In one embodiment, the estimation 220 can be a one-dimensional (1D) axial incremental displacement estimation using an RF-based cross-correlation method, as is known in the art and described in U.S. patent application Ser. No. 11/697,573, the entirety of which is incorporated by reference herein. In one embodiment, the estimation 220 is performed with a window size of 4.6 mm and an 80% overlap.

In the same or another embodiment, estimation 220 can comprise estimating the two-dimensional (2D) displacement. In one exemplary embodiment, to determine the 2D displacement, first a 16:1 linear interpolation scheme between two adjacent original RF signal segments can be employed to improve the lateral resolution. Second, the cross-correlation between reference RF signal segment and the candidate RF signal segments can be performed. Third, the RF signal segment in the comparison frame that yielded the highest 2D correlation coefficient can be considered the best match with the RF signal segment in the reference frame. One-dimensional cosine interpolation along each direction can then be applied around the initial maximal value of the cross-correlation function in order to increase the precision of the peak detection. Thus, the lateral displacement, i.e., $\Delta l$, denotes the estimated motion occurring between the reference RF signal segment and its best comparison frame match. The axial displacement, $\Delta a$, will be the estimated axial time-shift, or displacement, along the matched RE signal segment. Hence, a kernel in a 2D search yields the two orthogonal, in-plane components of the displacement simultaneously, i.e., ($\Delta l$, $\Delta a$). The lateral decorrelation due to axial motion reduces the accuracy of the lateral displacement estimation. Therefore, the correction in axial displacement estimation, or recorrelation, has to be performed to reduce this decorrelation noise. In myocardial elastography, a recorrelation method can be implemented by shifting RF signal segments according to the estimated axial displacement in the comparison frame, prior to the second lateral displacement estimation. The recorrelation strategy can also be utilized to correct the lateral displacement prior to the second axial displacement estimation. Once both lateral and axial displacement have been estimated it is possible to obtain radial and circumferential displacements. Since the myocardium can be segmented, the radial and circumferential directions can be defined as the directions normal and parallel to the tangent of the myocardial surfaces. When the epicardial and endocardial surfaces are not parallel, their tangential directions can be averaged.

The method 200 can further comprise determining 240 the time delay between the matched characteristic of the portion of the first sector 1 and the matched characteristic of the portion of the second sector 2. An image of the matched characteristic of the portion of the first sector 1 and the matched characteristic of the portion of the second sector 2 can be formed 250 utilizing the determination 240 of the time delay. The image can be formed 250 as either a one-, two-, three- or four-dimensional image. The image formed 250 can also be over the entirety of sectors 1, 2, thus creating a composite image of some or all of the sectors for which data was acquired 210. Multiple images formed 250 at different times may be sequenced over time to create a video of the moving tissue across the desired sectors 1, 2. For example, where the matched characteristic is the one-dimensional displacement, that displacement can be estimated 220 and matched 230 over time to form 250 a two-dimensional image, e.g., a video. In another example, an axial displacement can be estimated 220 and matched 230 in three-dimensions over time to form 250 a four-dimensional image, e.g., a video.

Figure 3B:
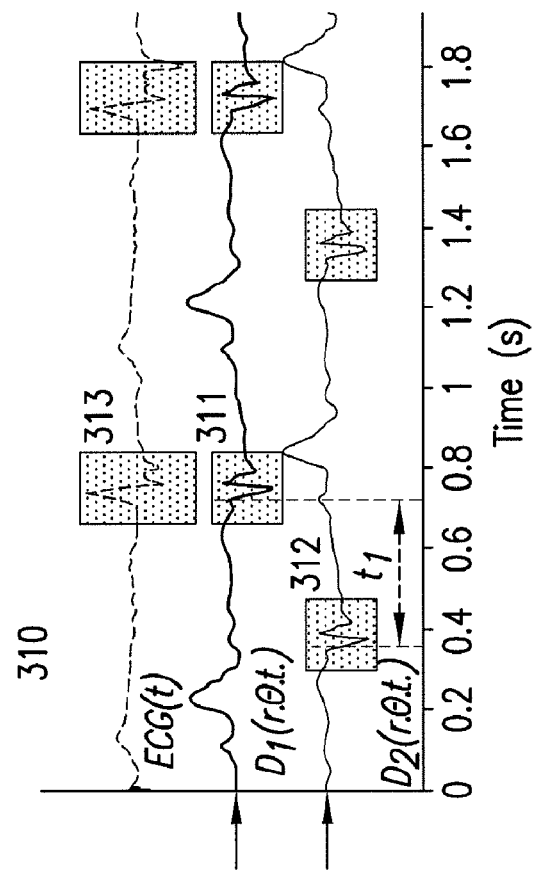
FIG. 3(b) illustrates a graph depicting the displacements of the two sectors illustrated in FIG. 3(a) over time, in accordance with an exemplary embodiment of the disclosed subject matter.
Figure 3A:
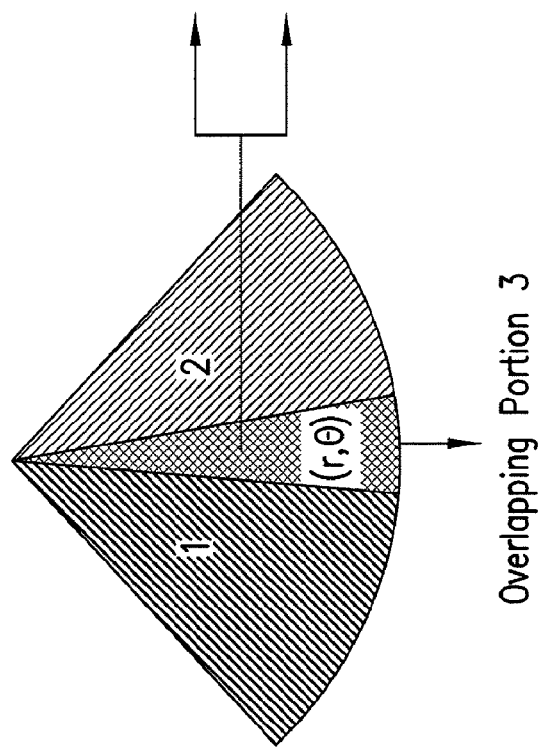
FIG. 3(a) illustrates an example of a method utilizing a two sectors acquired in accordance with an exemplary embodiment of the disclosed subject matter.

FIG. 3(a) illustrates an example of method 200 utilizing two sectors 1, 2 acquired 210 in accordance with an exemplary embodiment of the disclosed subject matter. As illustrated in FIG. 3, sector 1 and sector 2 share an overlapping portion 3. A characteristic, here displacement, is estimated 220 for each of sector 1 and sector 2. As FIG. 3(b) illustrates, the displacement of each sector k can be expressed as function $D_k(r, \theta, t)$, where displacement $D_k$ is a function of the depth r, angle θ, and time t. Thus, the displacement estimate for sector 1 ($D_1$) and sector 2 ($D_2$) can be computed at each point (r, θ).

FIG. 3(b) illustrates a graph 310 depicting the displacement functions $D_1$ and $D_2$ over time at point (r, θ) located in overlapping region 3. The displacements functions $D_1$ and $D_2$ should be identical for overlapping region 3, thus the matching 230 is accomplished by matching corresponding displacements found in both $D_1$ and $D_2$. The acquiring 210 of sectors happens sequentially, so it follows that the corresponding displacements found in $D_1$ and $D_2$ will be offset by some time period t. Graph 310 illustrates that characteristic (in this example displacement) 311 of $D_1$ and characteristic (in this example displacement) 312 of $D_2$ are corresponding characteristics that have been acquired at two different times, once in sector 1 and once in sector 2.

Once displacement 311 and displacement 312 have been matched 230, the time delay between data acquisitions 210 is determined by calculating the difference in the time of occurrence of 311 and 312. In FIG. 3(b), the displacements $D_1$ and $D_2$ are offset by time period $t_1$.

FIG. 3(b) further illustrates the electrocardiogram (ECG) for sector 1, graphed over time. As can be seen, the ECG for sector 1 shows a spike in electrical activity 313 corresponding to displacement 311 of $D_1$, thus confirming the accuracy of motion data as a representation of the electrical activity of the target tissue 120, in this example a heart. FIGS. 3(a)-(b) illustrate that the matching 230 and the time delay determination 240 can be performed visually, e.g., by graphing the characteristics over time. However, the matching 230 and time delay determination 240 can also be performed using the numerical approach discussed below.

In the example of a heart it can be assumed that the heart has a periodic motion, thus the same information is acquired twice in the overlapping regions at different times. Accordingly, in an exemplary embodiment where the target tissue 120 is heart tissue, the periodicity of that heart implies that the following equation holds for all sectors k, depths r, angles θ, and times t:

$$D_k(r,\theta,t) = D_k(r,\theta,t+nT), \quad (1)$$

where, as above, $D_k$ denotes the displacement estimate in sector k, T denotes one heart cycle duration and n is an integer. Each sector k+1 is delayed with respect to the preceding sector k and the following equation holds for overlapping sectors, denoted by θ':

$$D_{k+1}(r,\theta',t) = D_k(r,\theta',t+nT+t_k) = D_k(r,\theta',t+t_k). \quad (2)$$

Forming 250 the full-view image of all sectors k is equivalent to estimating $t_k$ for all k. This is achieved by finding the time associated with the peak of the cross-correlation function, also known as a motion-matching algorithm:

$$t_k = \underset{r,t'}{\mathrm{argmax}} \int_{-\infty}^{+\infty} D_{k+1}(r, \theta', t) D_k(r, \theta', t+t') dt. \quad (3)$$

Equation (3) can be implemented numerically and the true peak approximated using cosine interpolation. One of the main advantages of the characteristic-(or motion-) matching technique discussed herein is that the cross-correlation method also provides a correlation coefficient that indicates the quality of the sector matching. In one embodiment, data can be acquired 210 for two to three heart cycles per sector, it is then possible to select the best combination out of multiple heart cycles. For example, if two heartbeats were acquired 210 per sector over seven sectors, it would be possible to choose among 128 combinations of heart cycles.

It is understood that the above recited techniques, including the equations, would be useful in implementing the disclosed subject matter for tissues other than the heart, such as the liver, blood, or any tissue undergoing periodic motion.

Figure 4A:
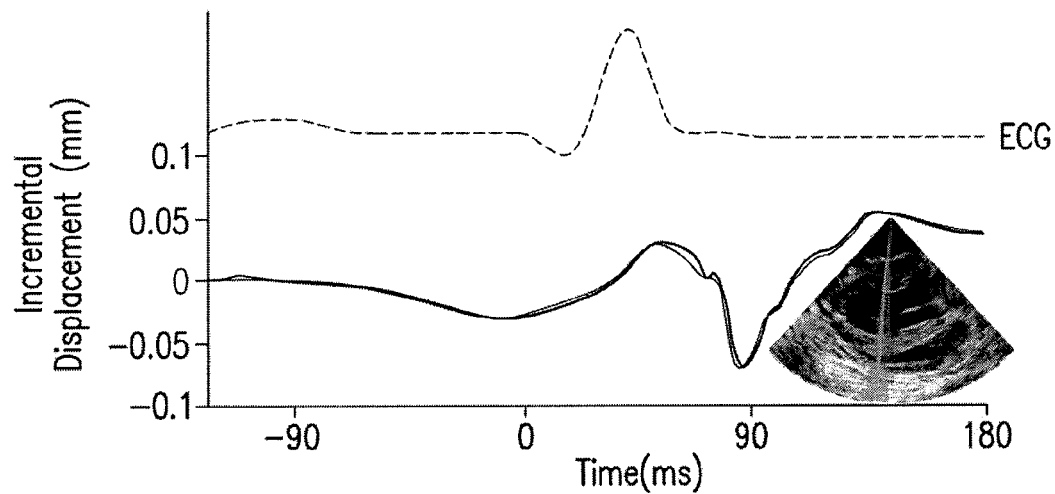
FIG. 4(a) is a graph illustrating the incremental displacements estimated in two sectors at the overlapping portion during two different cardiac cycles in a normal, open-chest, canine heart.

FIG. 4(a) is a graph illustrating the incremental displacements estimated 220 in sectors 1 and 2 at overlapping portion 3 based on data acquired in sectors 1 and 2 during two different cardiac cycles in a normal, open-chest, canine heart. FIG. 4(a) shows good matching between the temporal evolution of incremental displacements obtained in overlapping RF beams during the two different heartbeats. The top line in FIG. 4(a) represents the ECG.

Figure 4B:
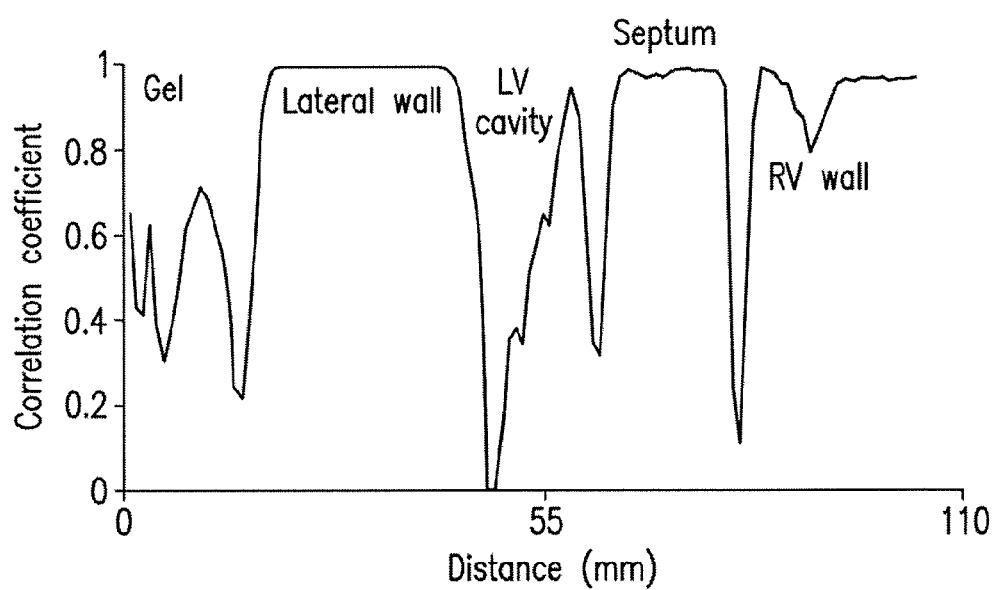
FIG. 4(b) illustrates the correlation coefficient in based on data taken from a normal, open-chest, canine heart.

FIG. 4(b) displays the temporal correlation coefficient along the same RF beam. As with FIG. 4(a), FIG. 4(b) illustrates the correlation coefficient in based on data taken from a normal, open-chest, canine heart, where LV is the left ventricle and RV is the right ventricle. A correlation coefficient close to 1 is obtained at the level of the myocardium, while the correlation was low in the blood cavities (due to the blood flow and low scattering) and in the surrounding ultrasound gel (which does not undergo periodic motion).

Figure 5A:
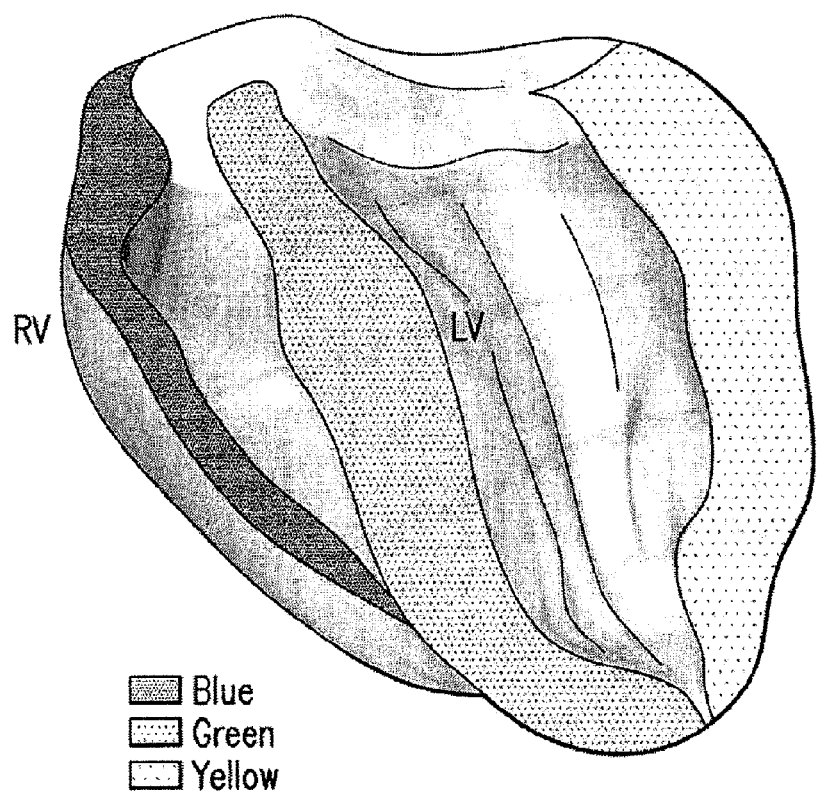
FIG. 5(a) illustrates a 3D rendering of a parasternal four-chamber view of a heart.
Figure 5B:
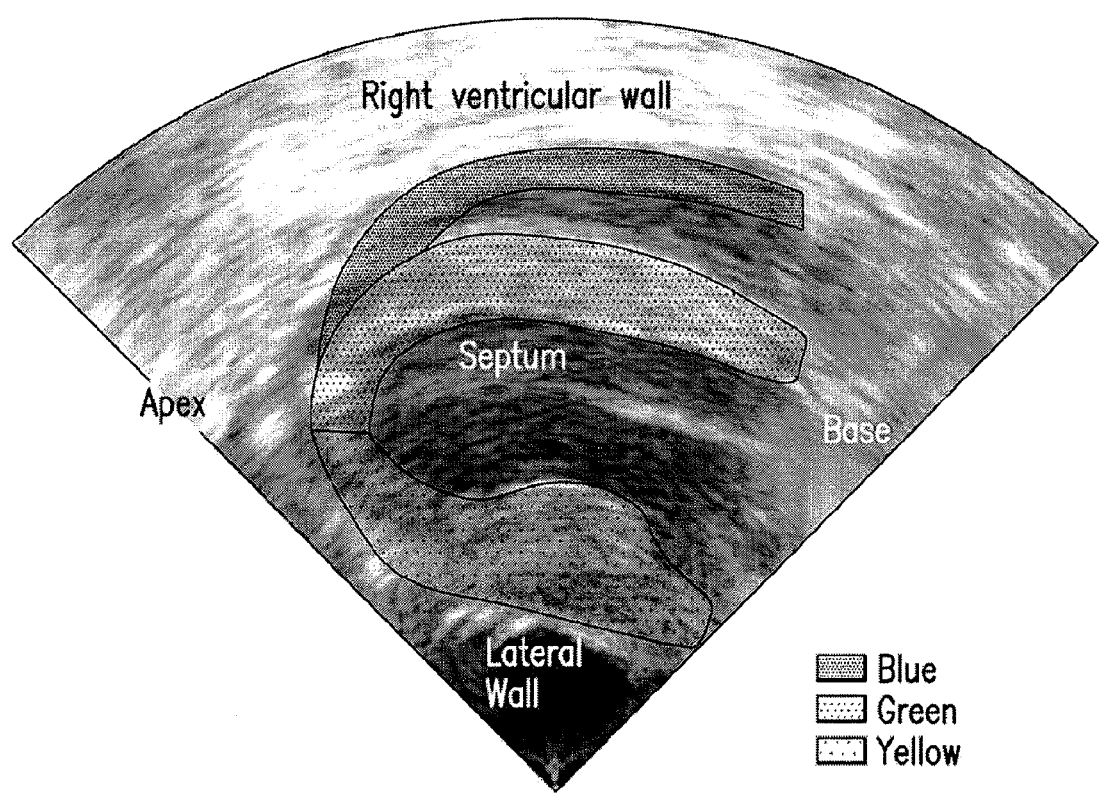
FIG. 5(b) illustrates a 2D parasternal four-chamber view of a heart prepared in accordance with an exemplary embodiment of the disclosed subject matter.

FIG. 5(a) illustrates a 3D rendering of a parasternal four-chamber view of a heart. FIG. 5(b) illustrates the corresponding 2D parasternal four-chamber view of a heart prepared in accordance with the techniques described herein. In FIGS. 5(a)-(b) both the right (RV) and left ventricle (LV) cavities are visible, along with the septum (green), the lateral wall (light shading) and the right ventricular wall (dark shading).

Figure 5C:
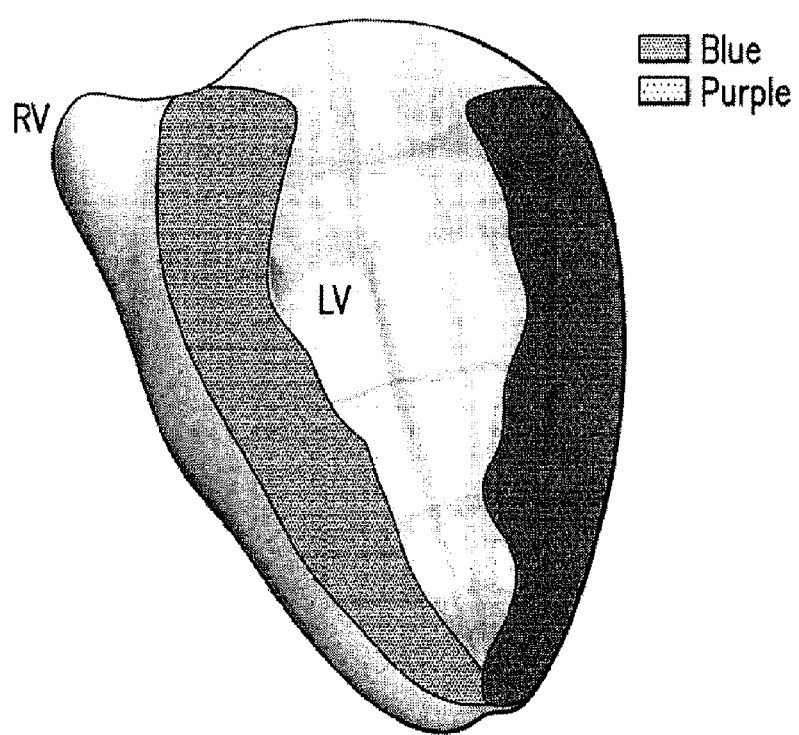
FIG. 5(c) illustrates a 3D rendering of parasternal two-chamber view of a heart.
Figure 5D:
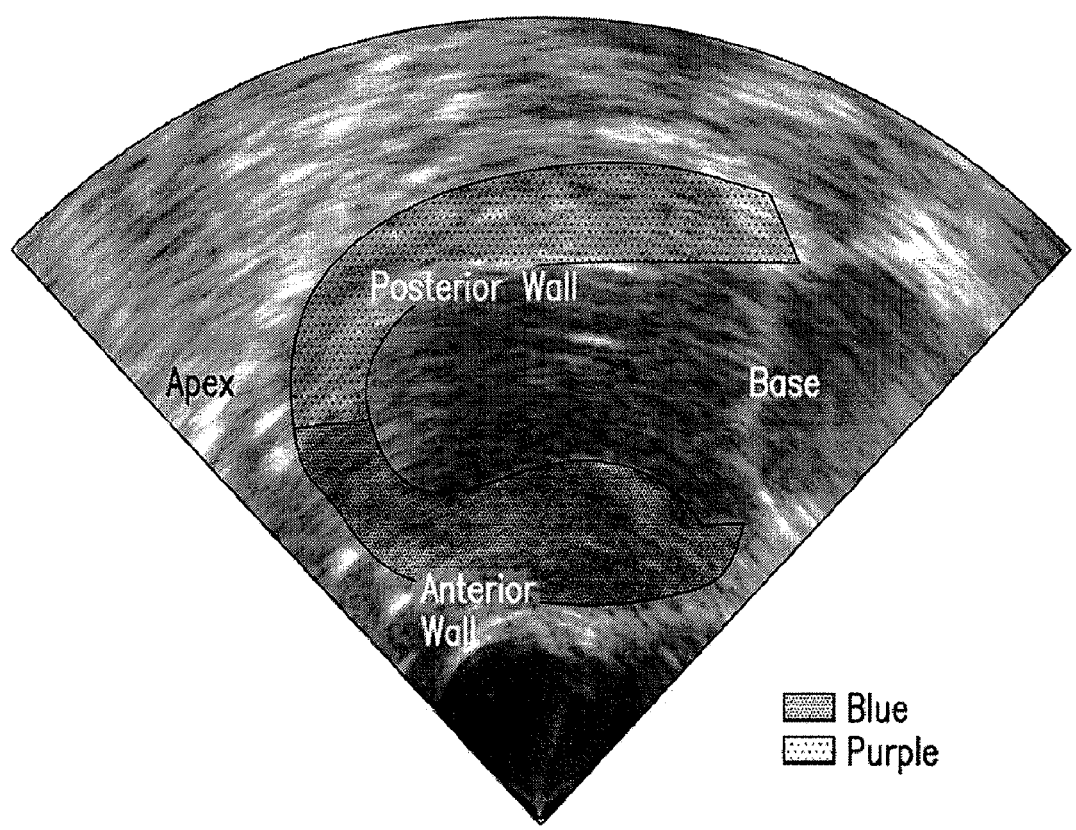
FIG. 5(d) illustrates the corresponding 2D parasternal two-chamber view of a heart prepared in accordance with an exemplary embodiment of the disclosed subject matter.

FIG. 5(c) illustrates a 3D rendering of parasternal two-chamber view. FIG. 5(d) illustrates the corresponding 2D parasternal two-chamber view of a heart prepared in accordance with the techniques described herein. In FIGS. 5(c)-(d), the left ventricle cavity is visible, along with the posterior and anterior walls. In both views (FIGS. 5(b) and 5(d)), the axial direction coincides most of the time with the radial direction.

As noted above, the estimating 220 the characteristic can comprise estimating a strain. The strain can be defined in terms of the gradient of the displacement and two-dimensions, in-plane displacement can be written as $\underline{u} = u_x \underline{e}_x + u_y \underline{e}_y$, where $u_x$ and $u_y$ are lateral and axial displacements, respectively. The $\underline{e}_x$ and $\underline{e}_y$ are unit coordinate base vectors in lateral and axial directions, respectively. The 2D displacement gradient tensor, $\nabla \underline{u}$, can then be defined as $$\nabla u = \begin{bmatrix} \frac{\partial u_x}{\partial x} & \frac{\partial u_x}{\partial y} \\ \frac{\partial u_y}{\partial x} & \frac{\partial u_y}{\partial y} \end{bmatrix}. \quad (4)$$

The 2D Lagrangian finite strain tensor, E, is defined as $$E = \tfrac{1}{2}(\nabla \underline{u} + (\nabla \underline{u})^T + (\nabla \underline{u})^T \nabla \underline{u}), \quad (5)$$

where $(\nabla \underline{u})^T$ is the transpose of $\nabla \underline{u}$. Lateral and axial strains will be diagonal components of E, i.e., $E_{xx}$ and $E_{yy}$, respectively. In order to improve the signal-to-noise ratio (SNR) a least-squares strain estimator (LSQSE) can be used. The LSQSE can reduce the noise from the gradient operation through a piecewise linear curve fit to the displacement. A larger lateral kernel, together with the recorrelation method, improves the quality of the estimated lateral strain and renders it comparable to the estimated axial strain.

As noted above, the method 200 can further comprise forming 250 an image of the characteristic of the tissue 120, which as discussed above can be the displacement, strain, velocity, strain rate, stiffness or other characteristic arising from periodic motion. Thus, a strain, velocity, strain rate, stiffness or other characteristic image can be formed 250 in one- to four-dimensions.

Figure 6:
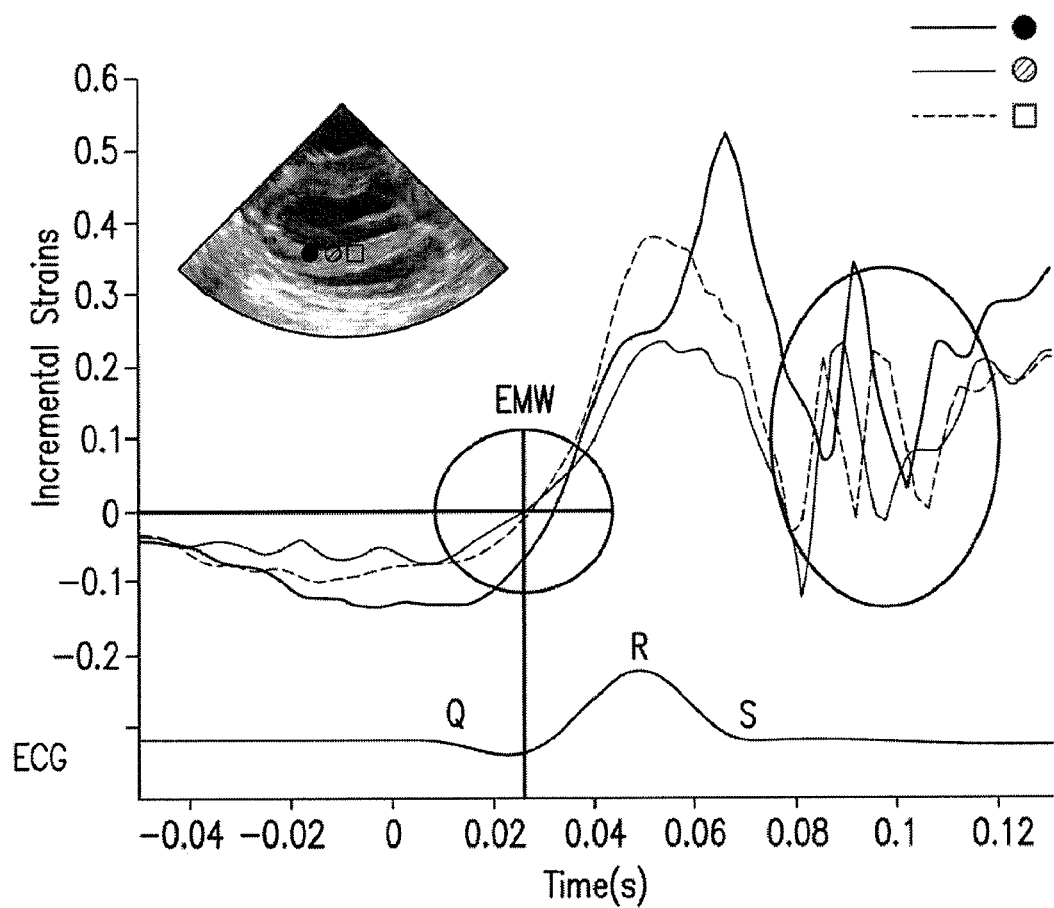
FIG. 6 is a graph of the temporal variation of the incremental strains along three points in the septum in accordance with an exemplary embodiment of the disclosed subject matter.

FIG. 6 is a graph of the temporal variation of the incremental strains along three points in the septum in the vicinity of the QRS complex (composed of the Q-wave, R-wave and S-wave, illustrated on the ECG line in FIG. 6). The location of the three points can be seen in the insert of FIG. 6, showing left, center and right dots representative of the location of strain measurements on a 2D image of the strain generated as detailed above. Two waves can be identified in FIG. 6: 1) the electromechanical wave (EMW) front defined by the point at which the incremental strains change sign and 2) a mechanical wave (the dashed circle) occurring when the mitral valve closes later and that oscillates both in time and space. The second wave travels from base to apex while the EMW is initiated at the endocardial surface of the septum and travels towards the base and the apex.

In accordance with the principles of the disclosed subject matter an experiment was conducted, with the approval of the Institutional Animal Care and Use Committee at Columbia University, on five mongrel dogs of either sex, ranging from 23 to 32 kg in weight. The dogs were anesthetized with an intravenous injection of thiopental (10-17 mg/kg). The dogs were mechanically ventilated with a rate- and volume-regulated ventilator on a mixture of oxygen and titrated isoflurane (0.5-5.0%). Morphine (0.15 mg/kg, epidural) was administered before surgery, and lidocaine (50 micrograms/kg/hr, intravenous) was used during the whole procedure. To maintain blood volume, 0.9% saline solution was administered intravenously at 5 mL/kg/hr. Each animal was positioned supine on a heating pad.

Standard limb leads were placed for surface electrocardiogram (ECG) monitoring. A solid state pressure transducer catheter (in this example one by Millar Instruments, Houston, Tex.) was inserted into the left-ventricular cavity via the left carotid artery, the aortic root and across the aortic valve. Oxygen saturation of the blood, and peripheral blood pressure were monitored throughout the experiment.

The chest was opened by lateral thoracotomy using electrocautery. After removal of the pericardium, a customized constrictor and a flow probe (in this example one provided by Transonic Systems, Inc., USA) were positioned immediately distal to the first diagonal of the left anterior descending (LAD) coronary artery to induce graded occlusion—and thus variable ischemic levels—at 20% increments of the initial coronary blood flow.

A total of twelve piezoelectric crystals (provided by Sonometrics Corp., Canada) were then implanted in the left ventricular wall. For endocardial and mid-wall crystals, an 18 G (18 gauge) needle was used for insertion. All crystals were maintained in position after placement using silk sutures.

Echocardiography was performed at each occlusion level. Forty-five minutes after complete occlusion, the LAD was reperfused. It was then excised and sectioned in 1 cm transverse slices to perform pathology. The sliced heart sections were immersed in a 1% Triphenyltetrazolium chloride (TTC) solution and incubated at 37° C. for 1.5 hours. The sections were then fixed in a 10% formalin solution for 30 minutes. A pale region indicated the site of infarction, while the stark color represented the viable cardiac muscle.

FIG. 7(a)1-FIG. 7(a)6 illustrate the propagation of incremental displacement in the four-chamber view over six image frames formed 250 during the above-described canine experiment. As illustrated in the side bar in FIG. 7(a)1-FIG. 7(a)6 light shading indicates movement (displacement) up and dark shading indicates movement (displacement) down, while RV, IVS, LV, and LAT respectively denote right ventricle cavity, interventricular septum, left ventricle cavity and free wall (lateral wall). Therefore, a contracting heart will be mapped in dark shading at the septum and right ventricular wall and in light shading at the lateral wall. FIG. 7(a)1-FIG. 7(a)6 illustrate the corresponding displacement patterns propagating from base to apex in the septum and lateral wall, and propagation of downward motion in the right ventricular wall. The arrows in FIG. 7(a)1-FIG. 7(a)6 highlight some areas where notable displacement can been seen.

FIG. 7(b)1-FIG. 7(b)6 illustrate 2D strain images generated 250 during the above-described canine experiment. As discussed above, a least-square strain estimator (LSQSE) was then applied on the incremental displacement data, providing the incremental strain information. As illustrated in the side bar in FIG. 7(b), light shading indicates thickening while dark shading indicates thinning. In regions where the axial direction coincides mainly with the radial direction, contraction will be mapped as thickening of the myocardium. More specifically, two activation sites at the mid-basal level are visible approximately 30 ms after the Q-wave in both the left endocardium of the septum and in the endocardium of the lateral wall (indicated by the dark shaded arrows in the 31.60 ms frame). This is a thickening wave that travels towards both the base and the apex. At approximately 40 ms, a thickening wave becomes visible in the right ventricular wall (white arrow), which travels principally towards the base. Noticeably, 60 ms after the onset of the Q-wave, the basal parts of the three walls are still thinning (light arrows in 61.54 ms frame). In the region where the axial direction matches the longitudinal cardiac coordinate, circled in the 61.54 ms frame, shortening, rather than thickening, is observed.

Figure 8:
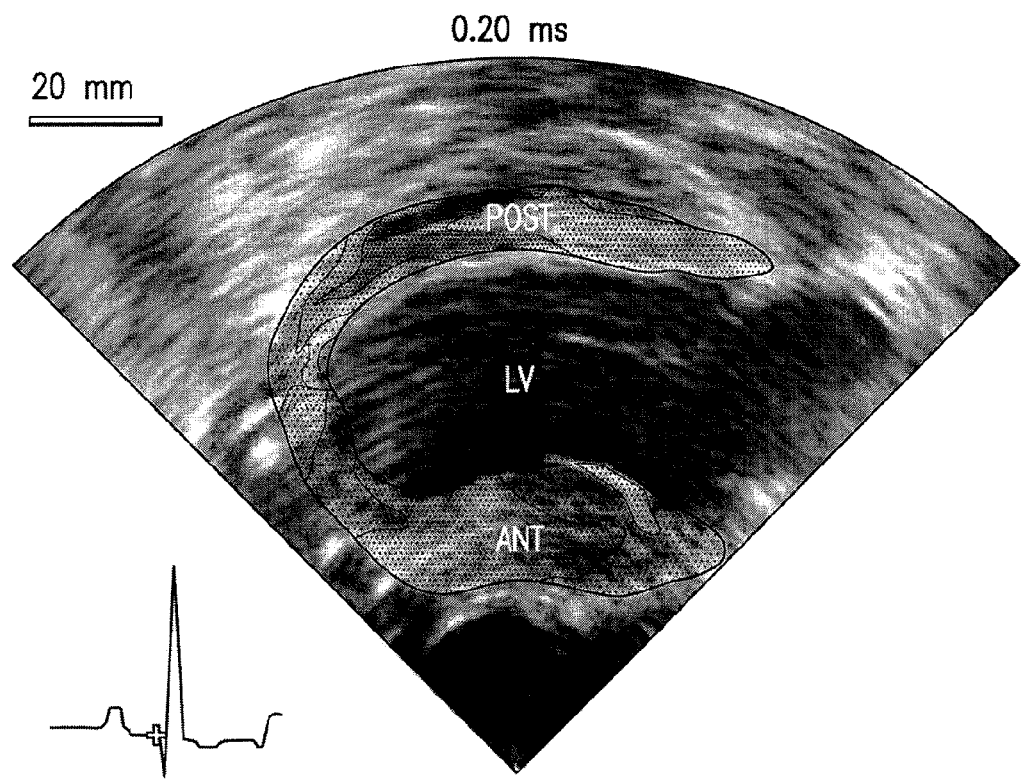
Figure 1:
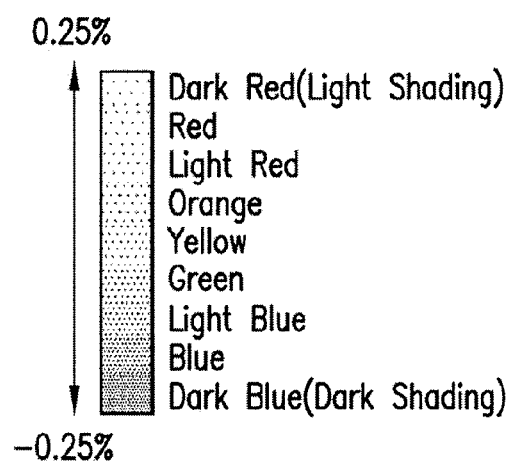
Figure 8:
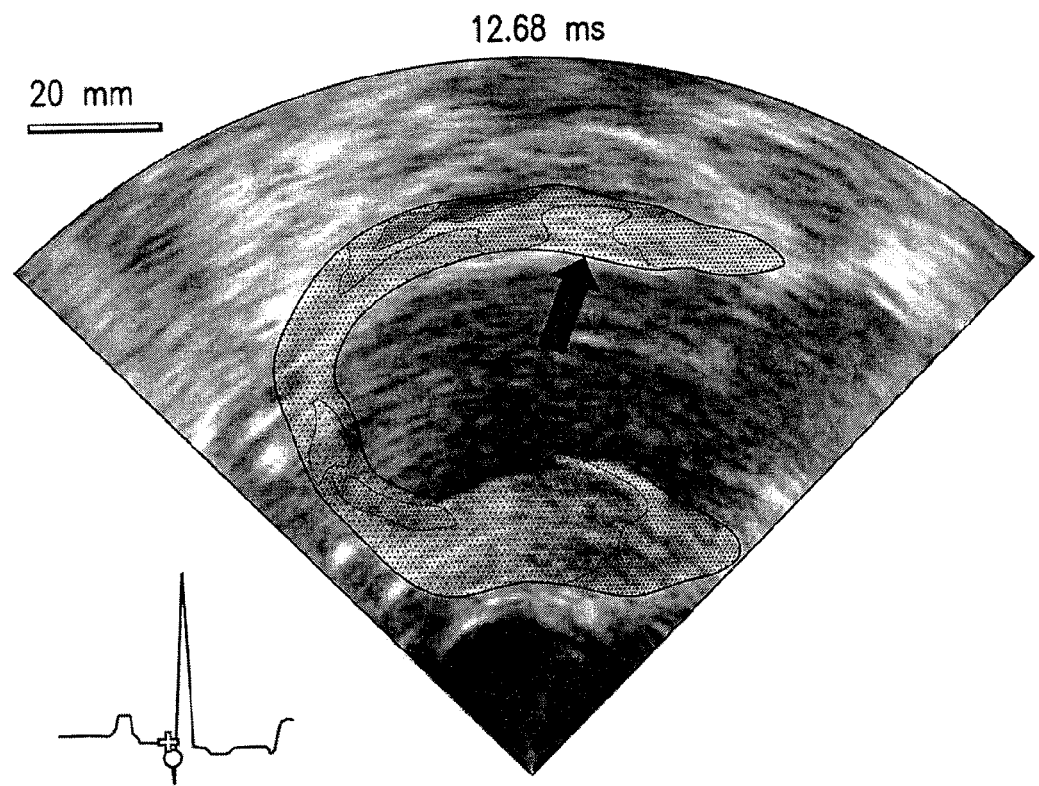
Figure 2:
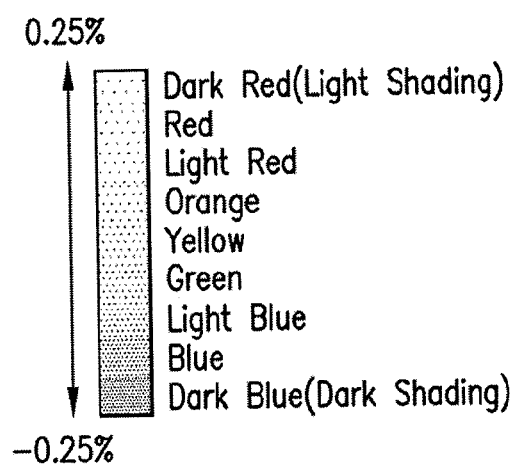
Figures 3, 8:
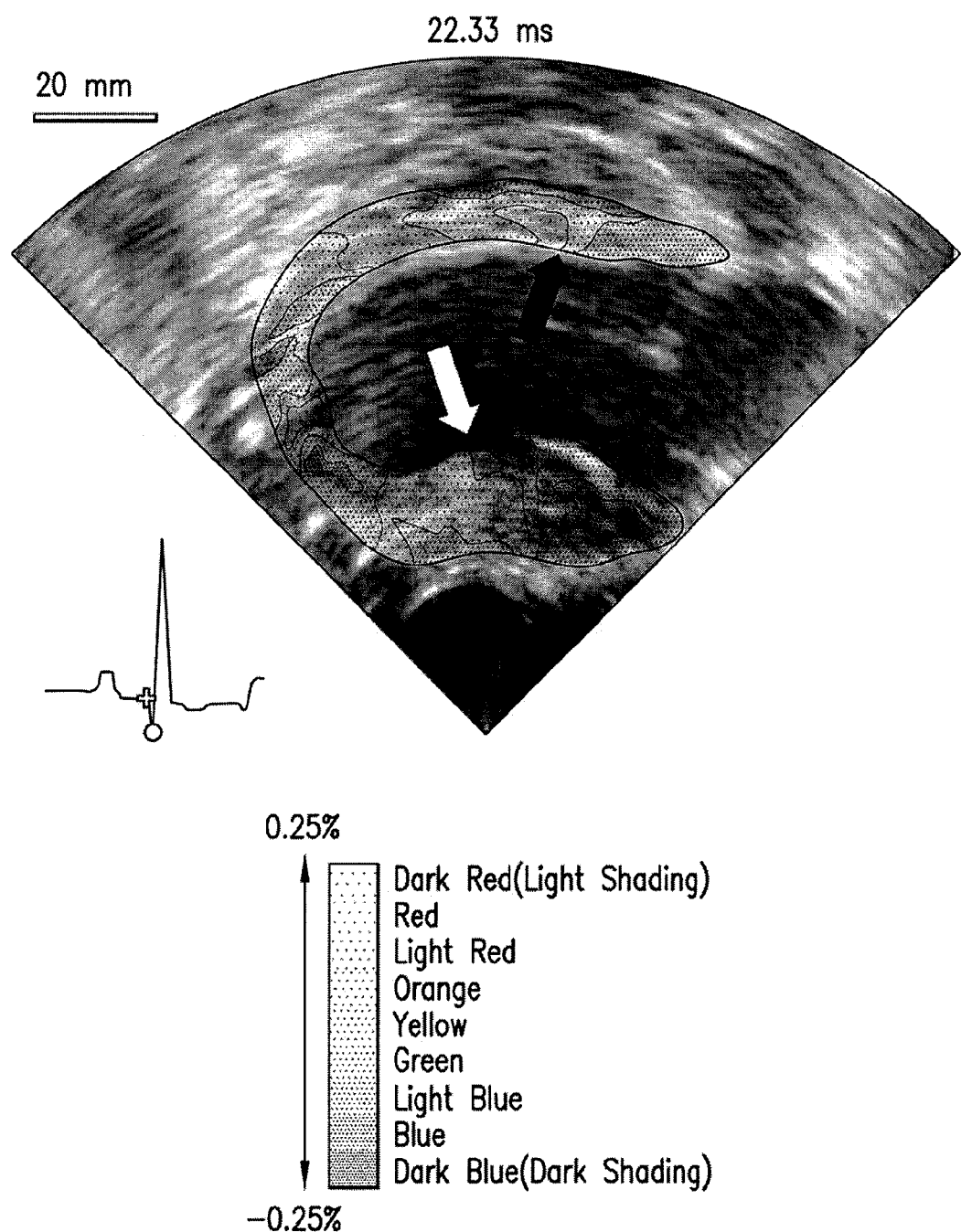
Figure 8:
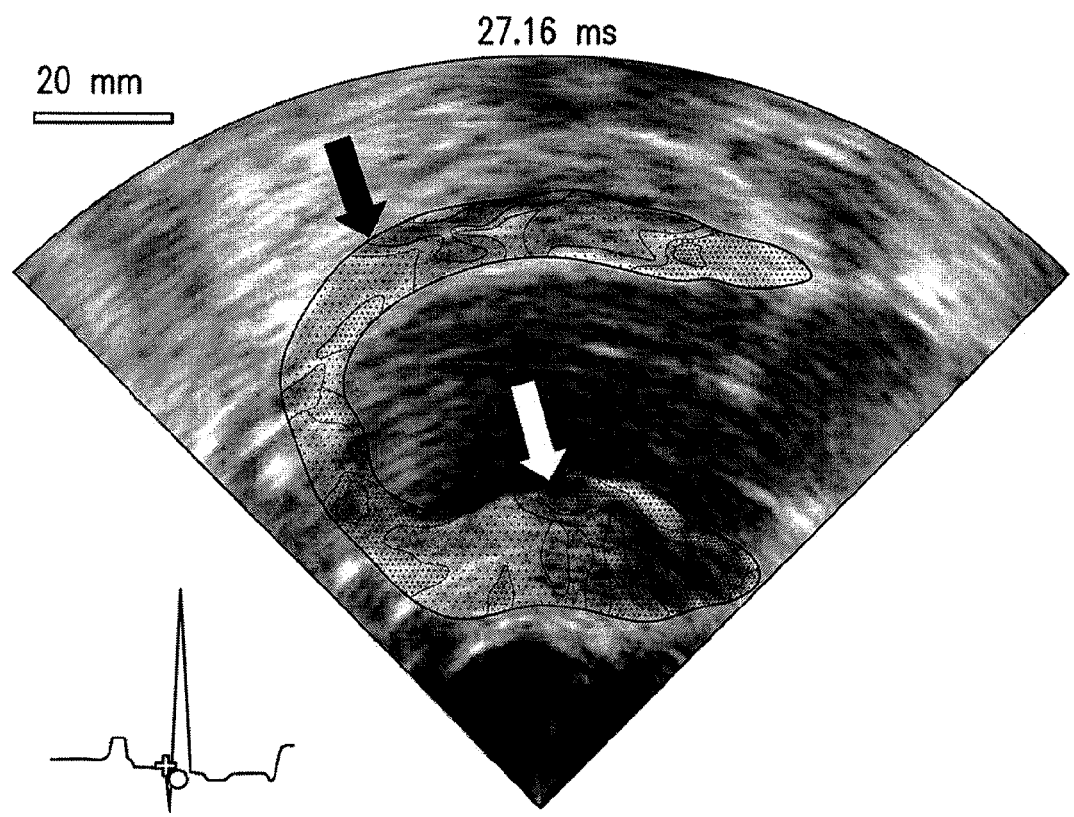
Figure 9:
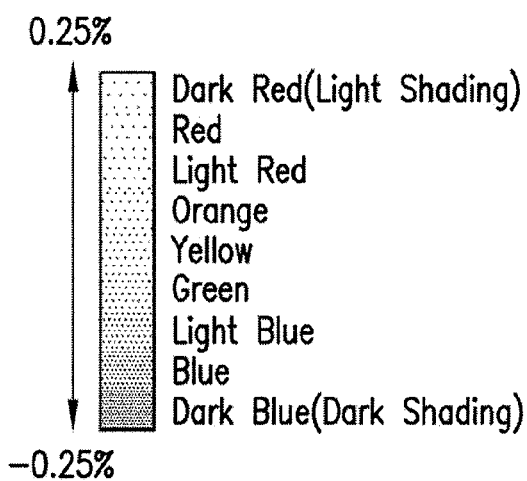
Figure 9:
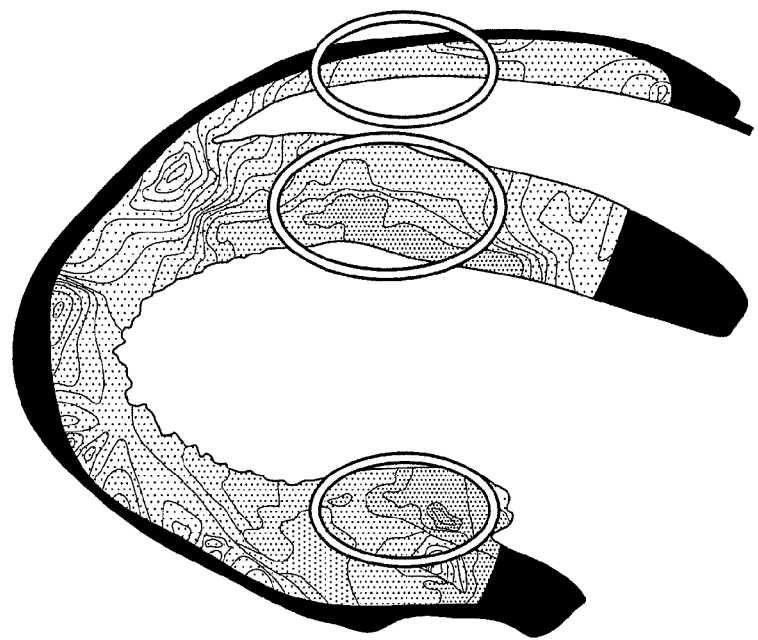
Figure 1:
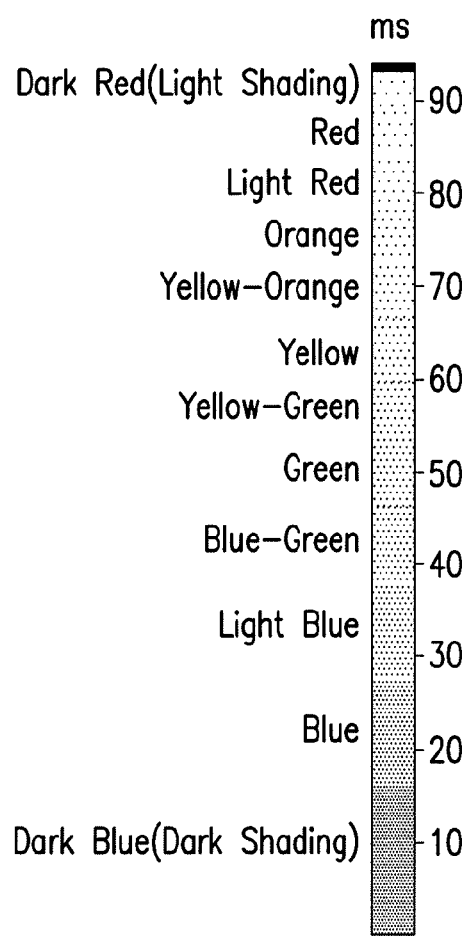
Figure 9:
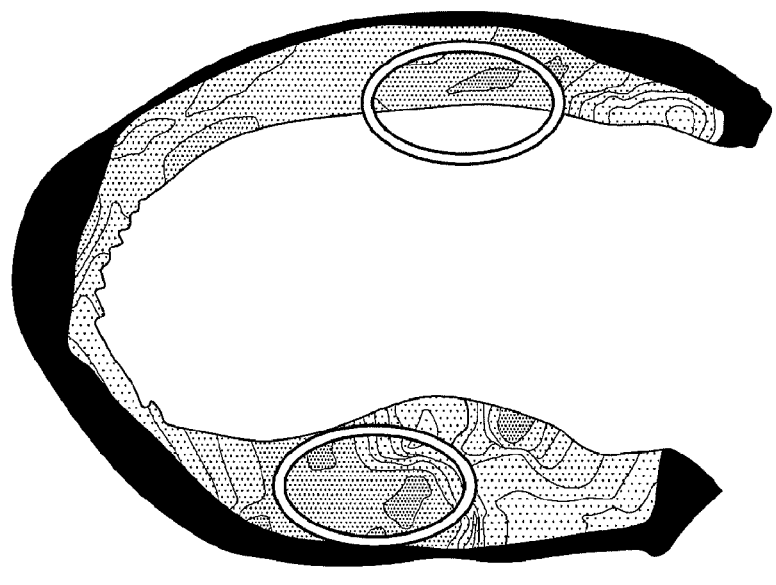
Figure 2:
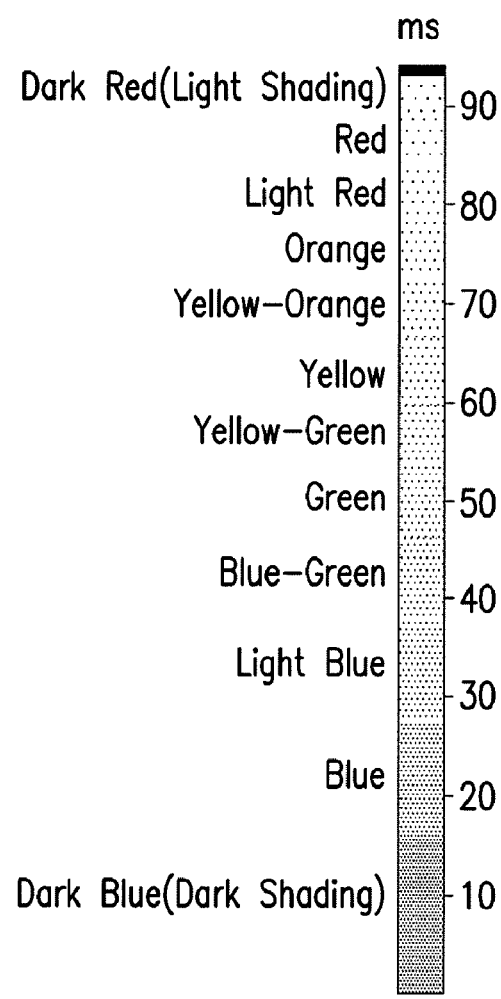
Figure 9:
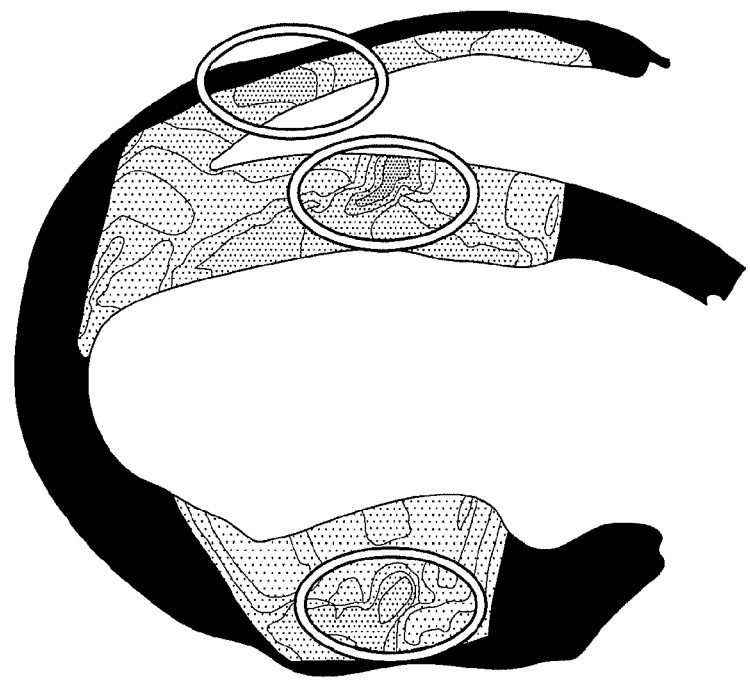
Figure 3:
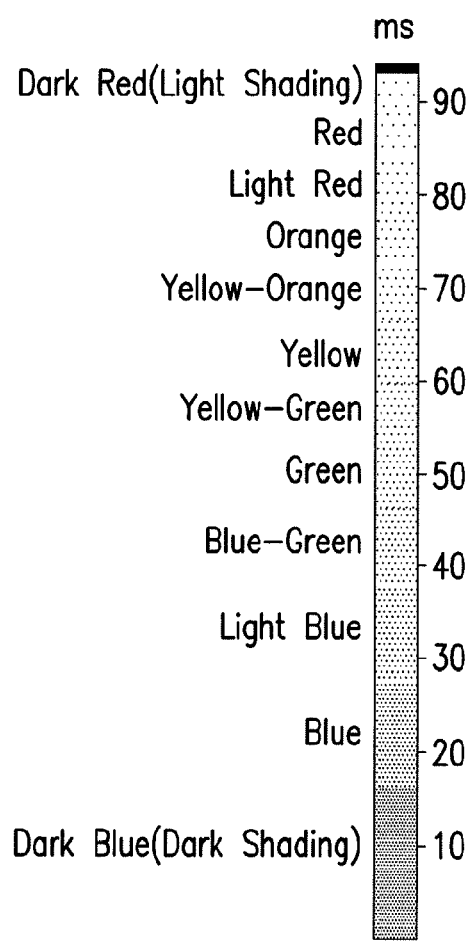
Figure 9:
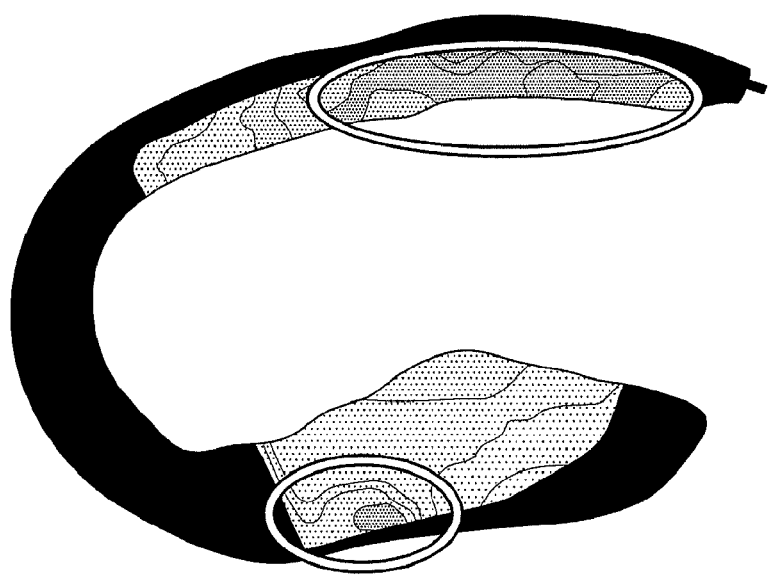
Figure 4:
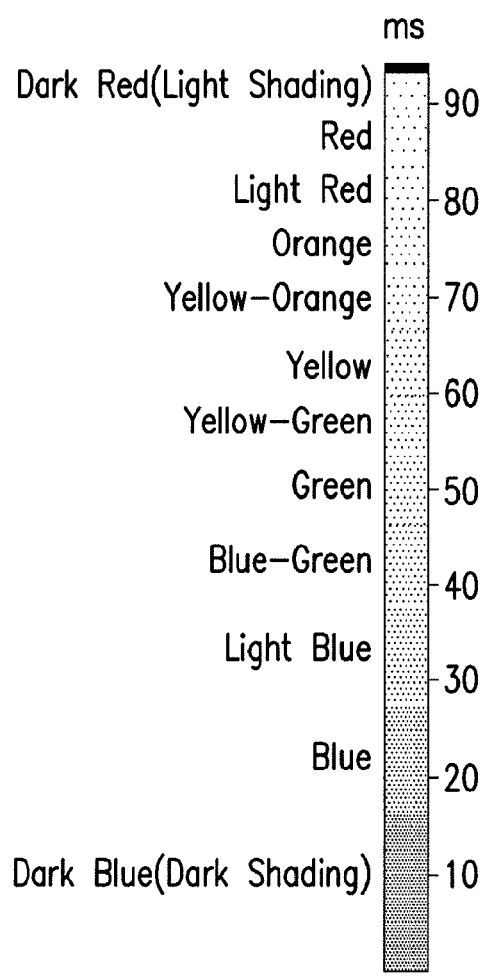

FIG. 8-1-FIG. 8-9 illustrate 2D strain images of electromechanical wave propagation in a normal heart under sinus rhythm in the parasternal two-chamber view, with LV, ANT and POST respectively denoting left ventricle cavity, anterior wall, and posterior wall. As illustrated in FIG. 8, approximately 12 ms after the onset of the QRS, excitation of the posterior wall endocardium begins (green arrow in the 12.68 ms frame). It then propagates both towards the base and the apex. A few milliseconds later, the anterior wall begins to thicken (white arrow in the 22.33 ms frame). The myocardium is almost completely mechanically activated 45 ms after the onset of the QRS; thinning of portions of the base are still visible. The bottom row of FIG. 8 illustrates that the mitral valve closing generates an oscillating wave (light circle), different in nature from the EMW, that emanates from the base and travels towards the apex in the posterior wall.

Figure 4:
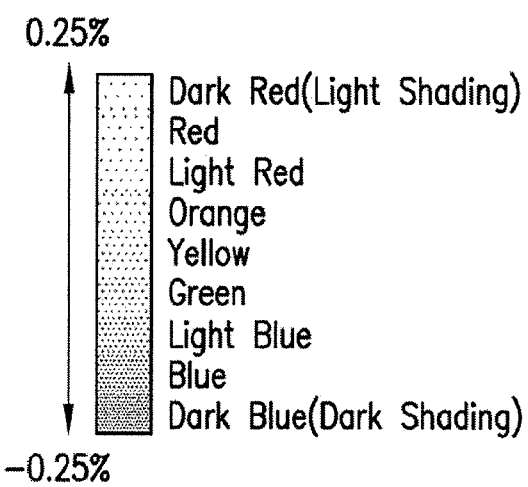
Figure 8:
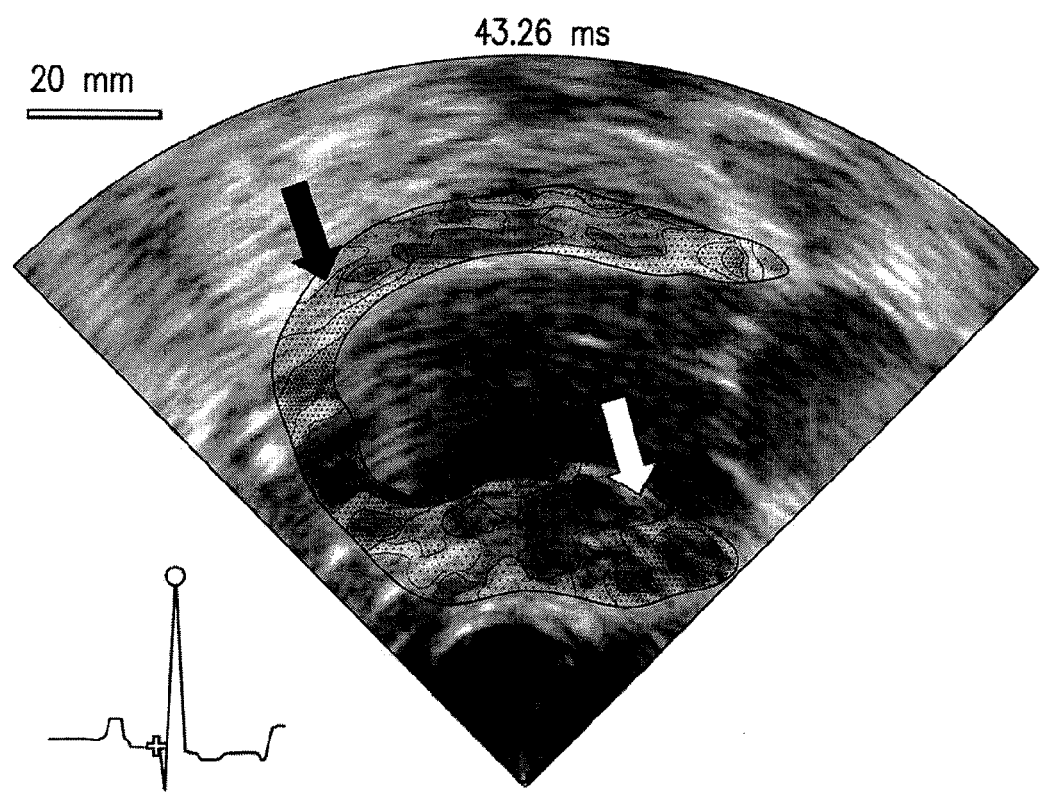
Figure 5:
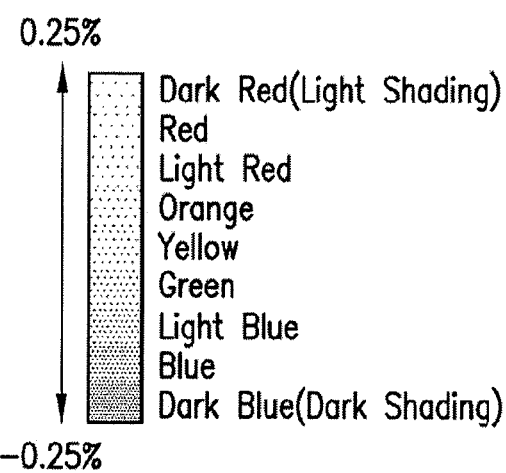
Figures 6, 8:
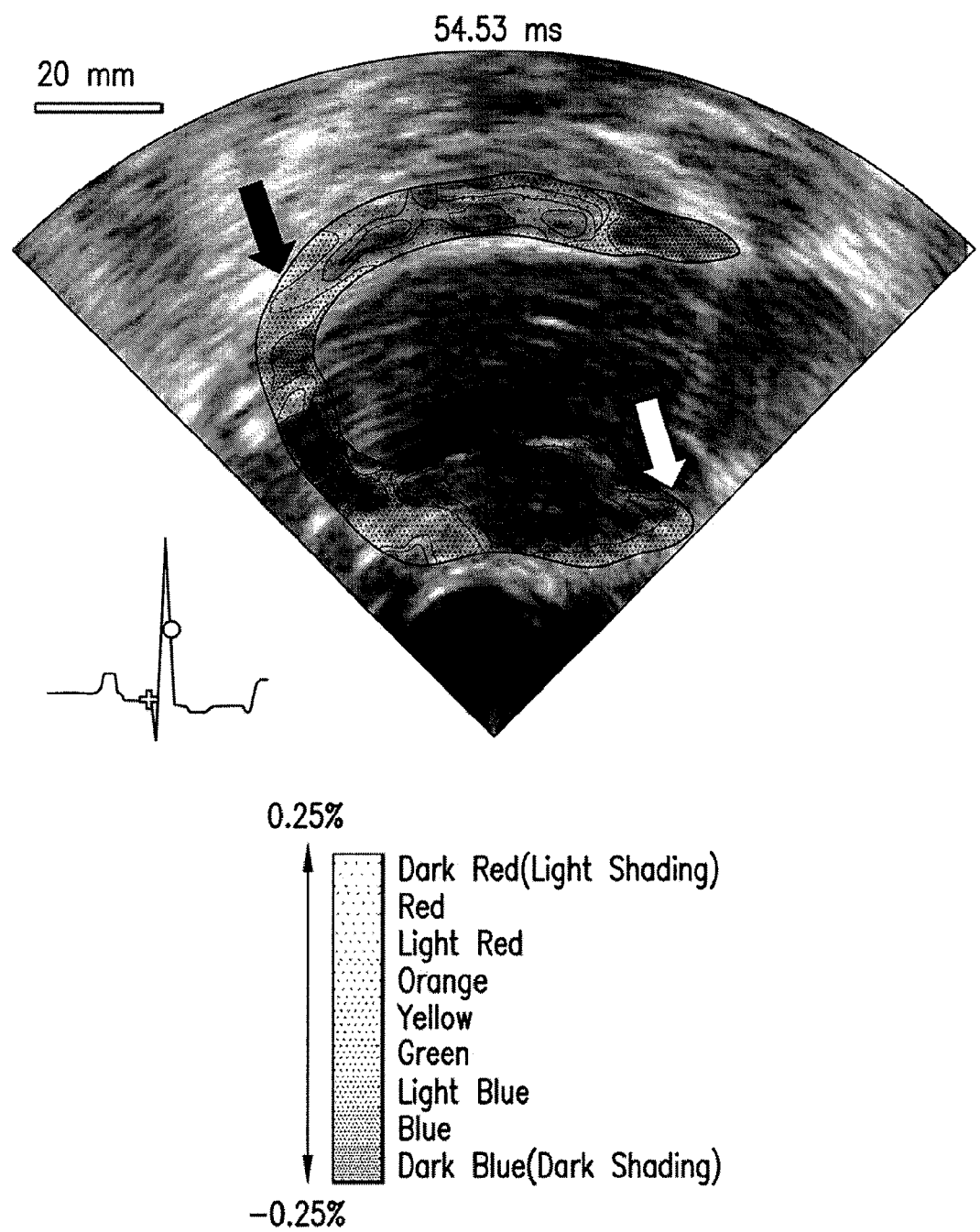
Figures 7, 8:
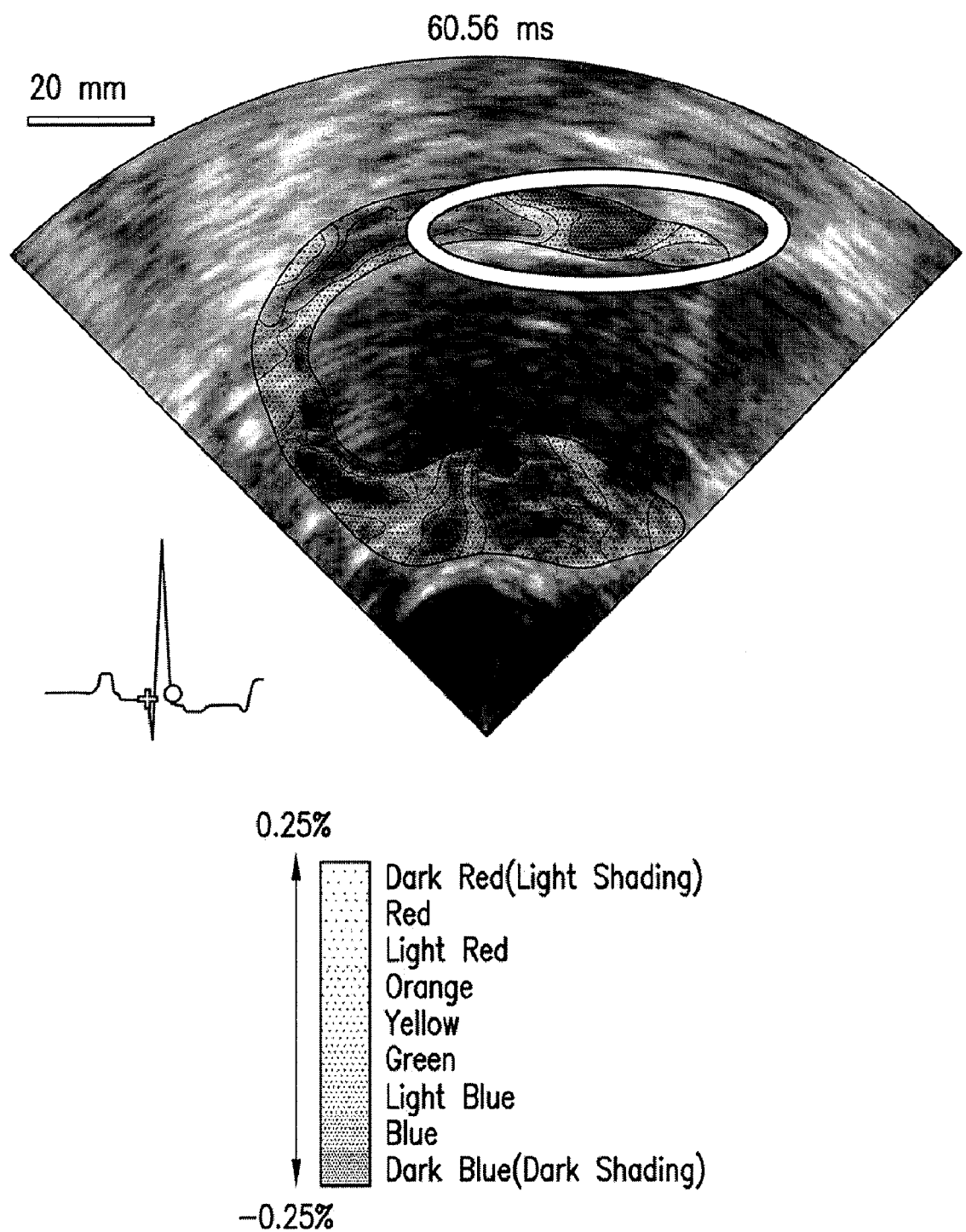
Figure 8:
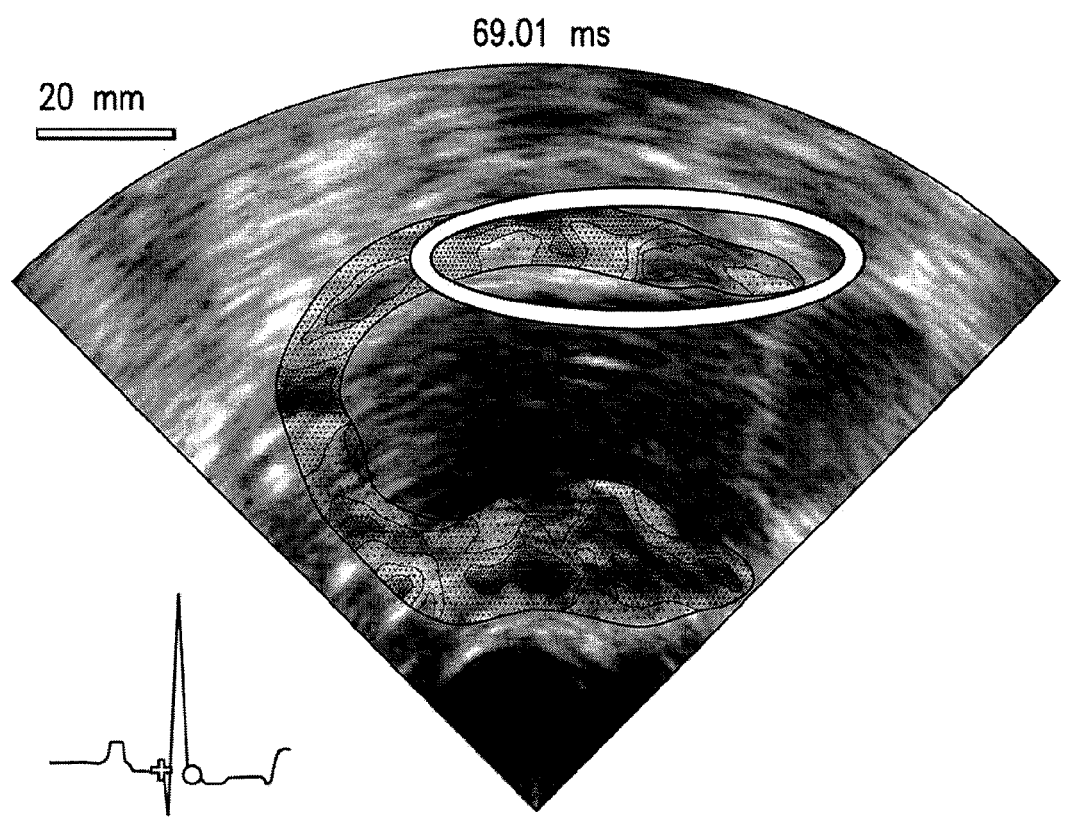

FIG. 9-1-FIG. 9-4 illustrate isochrones of the two different dogs in the two- and four-chamber view showing the time of arrival of the EMW. As illustrated in FIG. 9 the propagation patterns in the two dogs are not identical, but show similar regions of early depolarization and a propagation emanating from those regions to apex and base. The dark circles indicate the regions where the activation times correspond to shortening rather than thickening. This aforementioned EMW propagation is disrupted when, as illustrated in FIG. 8 and discussed above, the mitral valve closes a few milliseconds after the R-wave, approximately at 45 ms.

As discussed above, the techniques described herein are particularly advantageous to imaging cardiac tissue suffering from one or more irregularities, such as ischemia. As a part of the above-described experiment the left anterior descending (LAD) coronary artery was subsequently partially occluded, the coronary flow steadily reaching 80, 60, 40, and 20% of its initial value. Each occlusion increment was sustained for approximately one hour. The LAD was finally completely occluded. Twenty minutes after each occlusion, and over a twenty minute period, the heart was imaged in both the two- and four-chamber views.

Figure 10A:
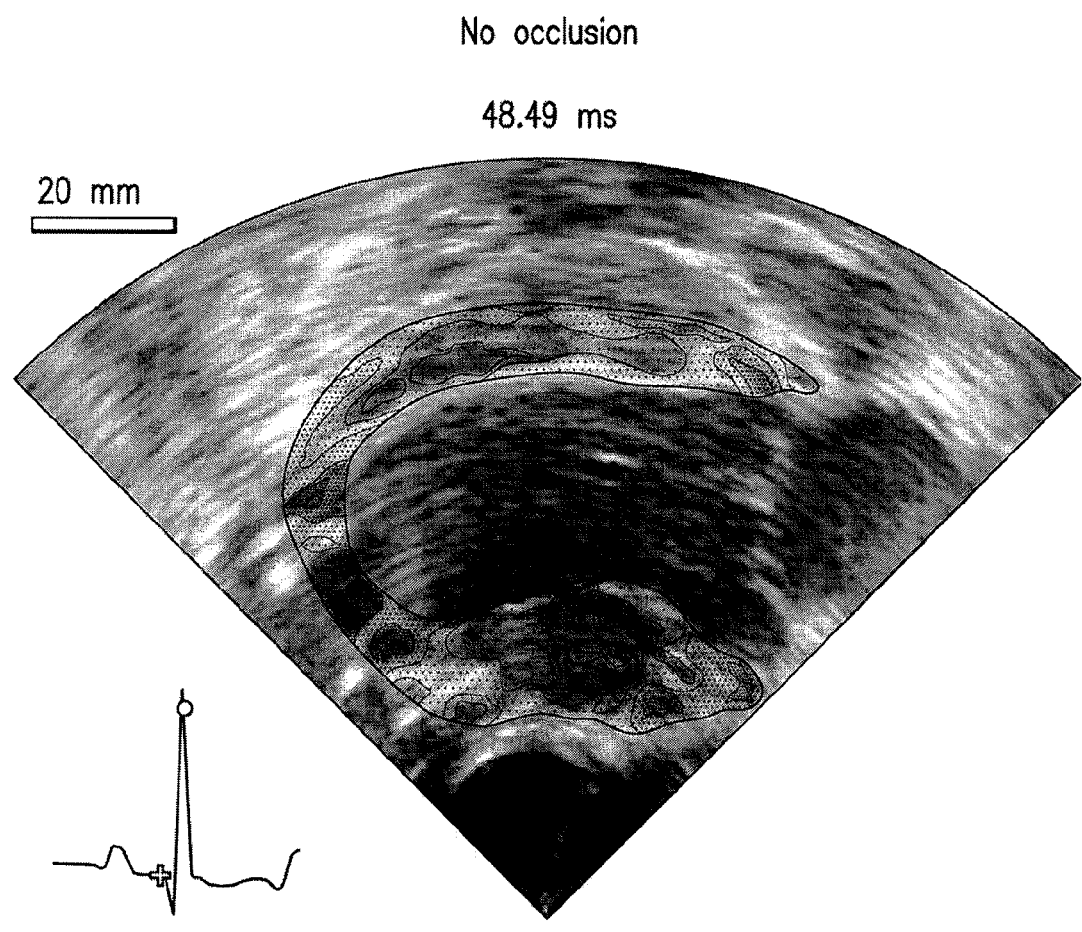
Figure 10B:
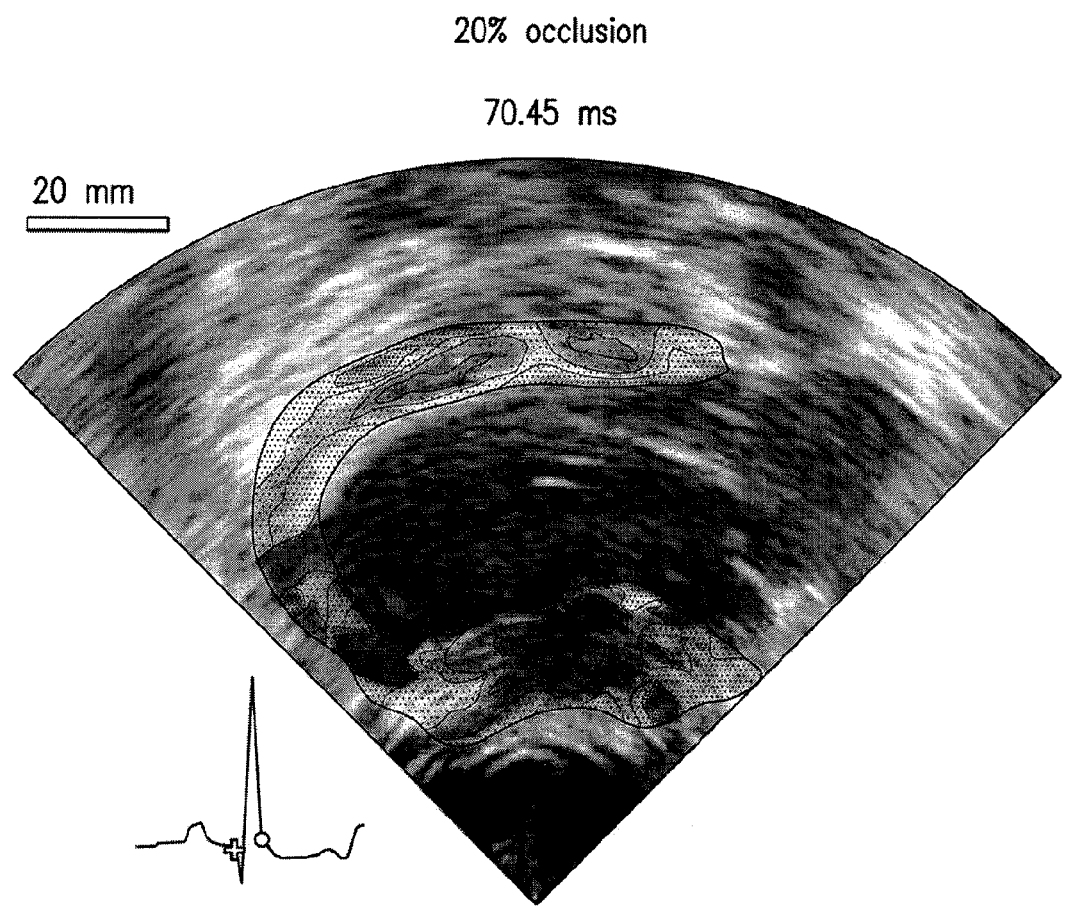
Figure 10D:
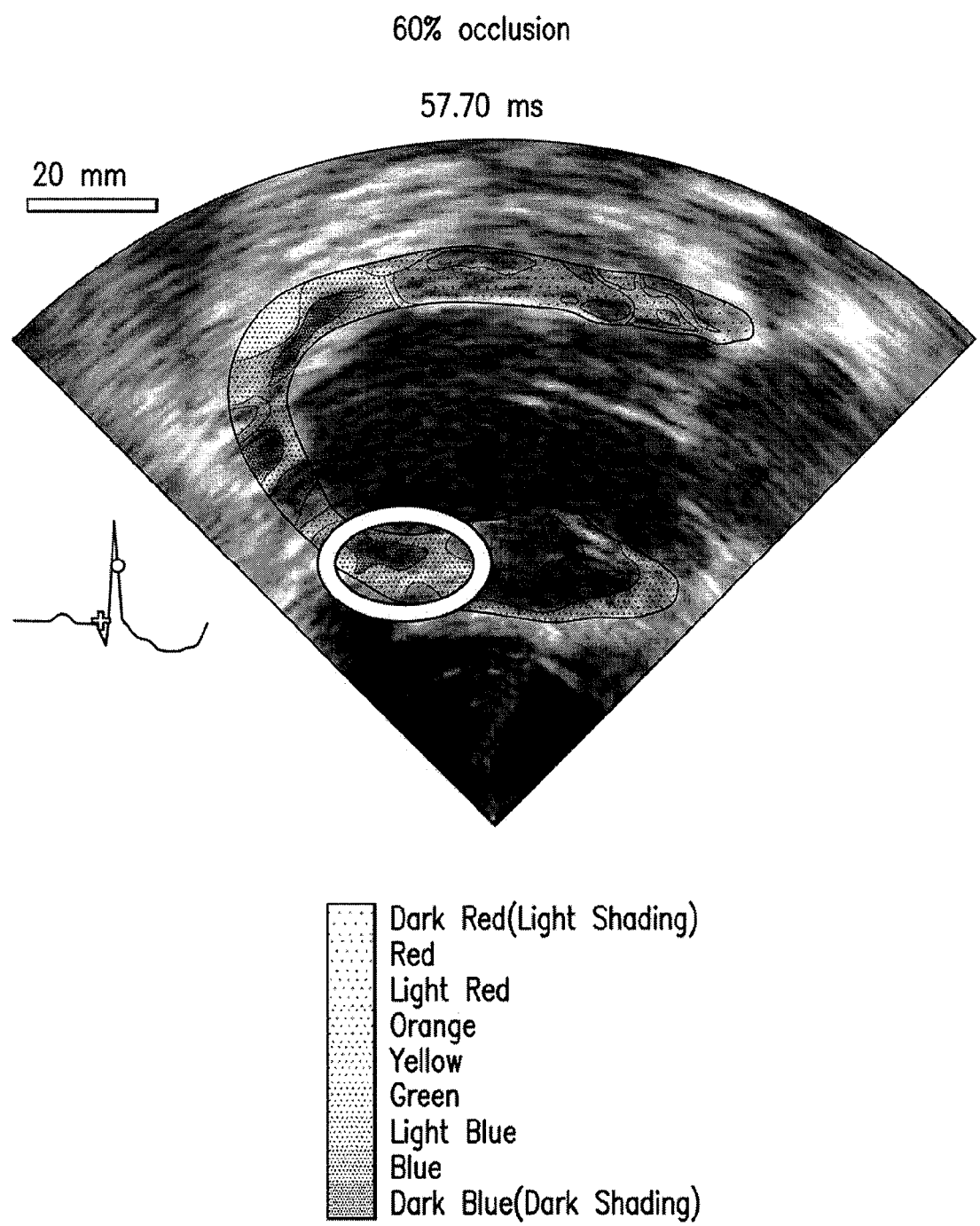
Figure 10E:
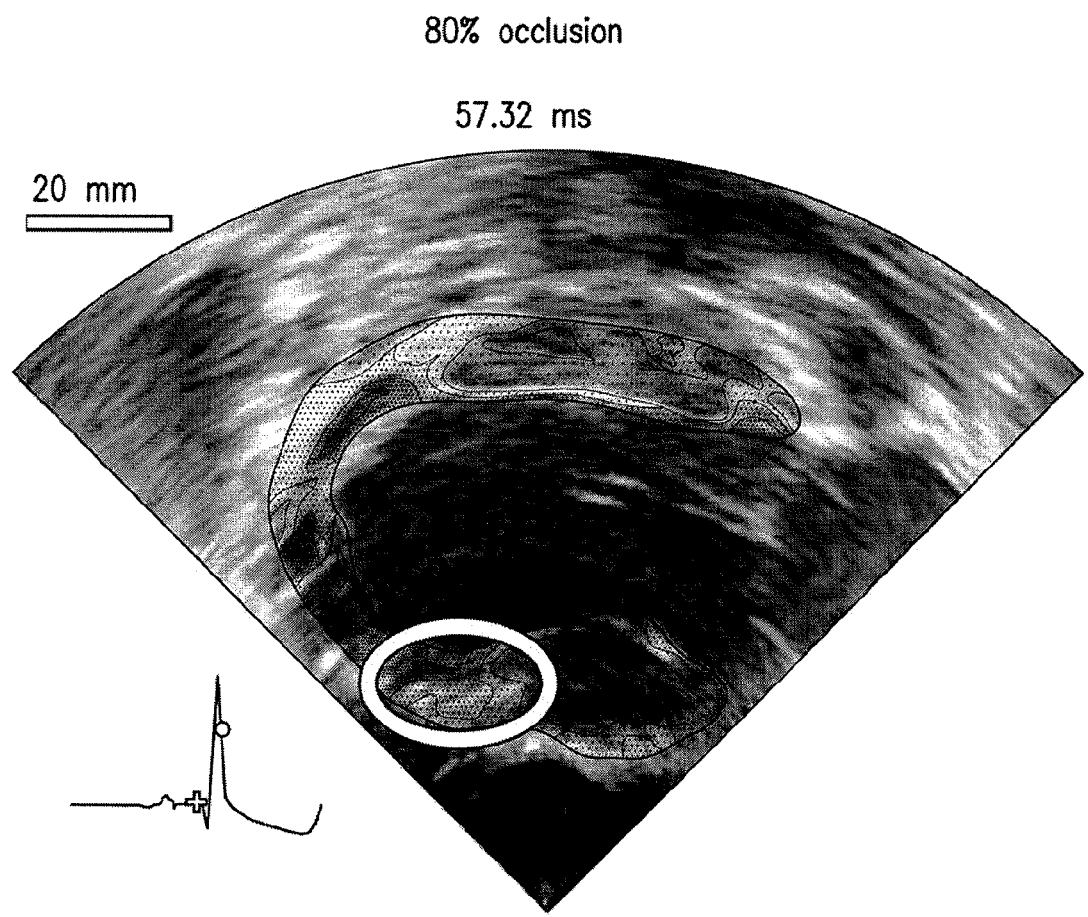
Figure 10F:
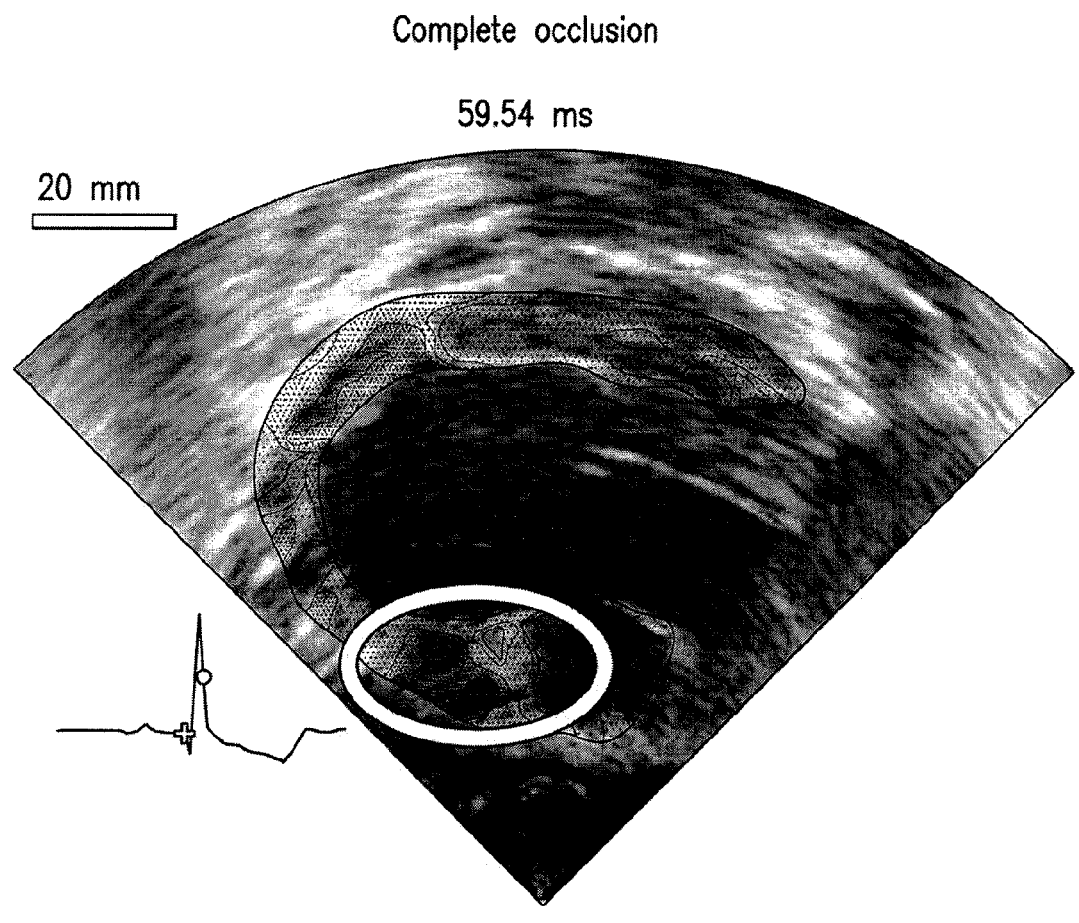
Figure 10G:
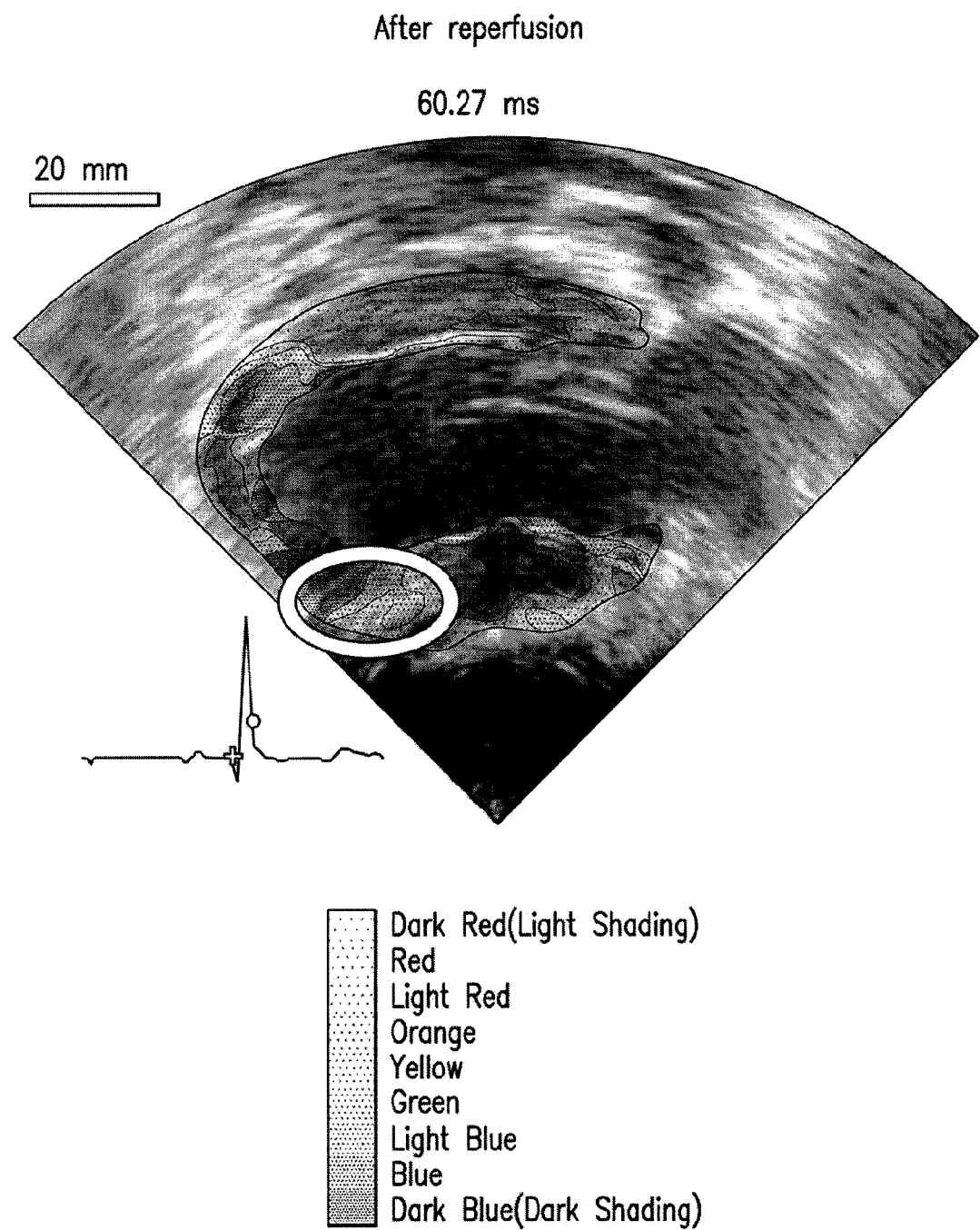
FIG. 10(g) illustrates the evolution of the electromechanical wave after reperfusion in accordance with an exemplary embodiment of the disclosed subject matter.

FIG. 10(a)-(f) shows the evolution of the EMW with different levels of ischemia, representing no occlusion, 20%, 40%, 60%, 80% and finally 100% occlusion in FIG. 10(f). The time at which the images in FIGS. 10(a)-(f) are displayed corresponds to the time at which the activated region covered the largest portion of the myocardium, i.e., immediately preceding the closing of the mitral valve. FIGS. 10(d)-(f) illustrate the ischemic region (light circle), which can be easily identified as the region through which the EMW cannot propagate. Comparison to FIGS. 10(a)-(c) indicates that the ischemic region is visible when the LAD is occluded at 60% and beyond. The ischemic region appears to grow with the occlusion level until it reaches a maximum size at 100% occlusion. After reperfusion, illustrated in FIG. 10(g), the size of the ischemic region in the posterior wall decreases.

Figure 10H:
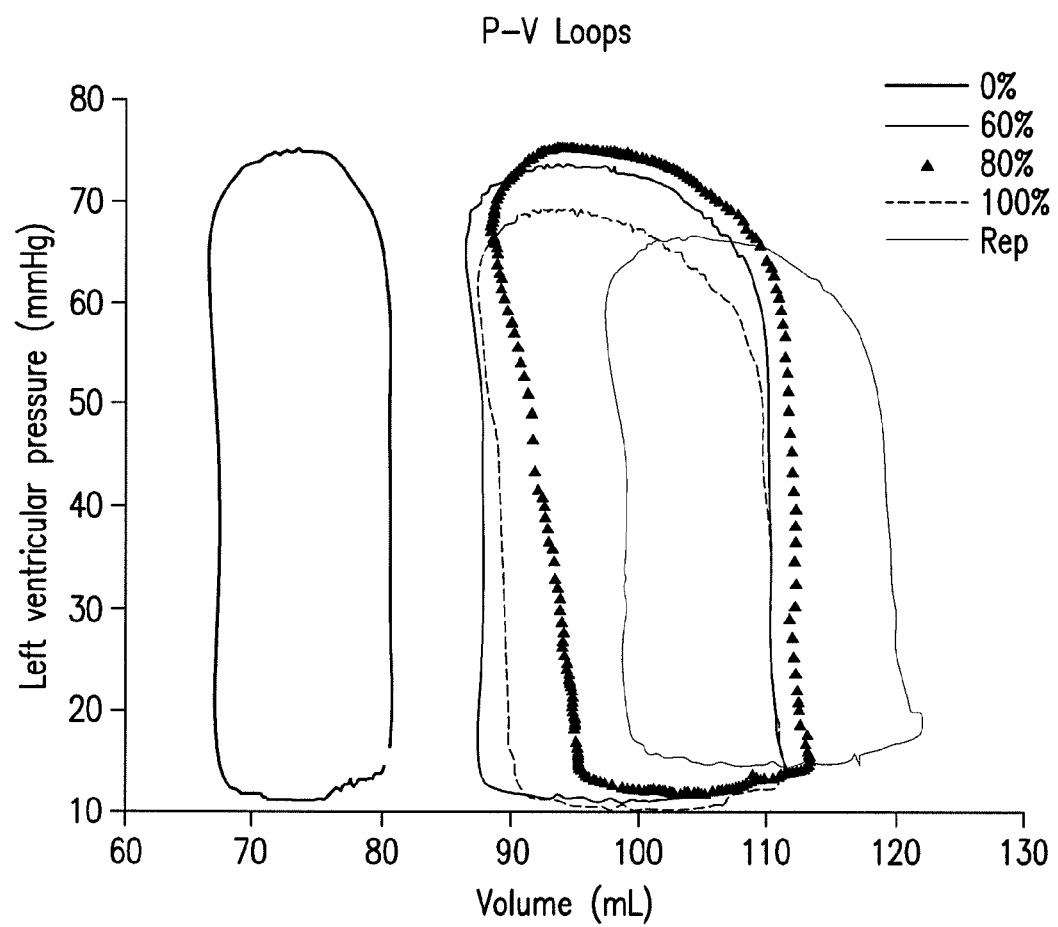
FIG. 10(h) illustrates the evolution of the P-V loop with the occlusion level in accordance with an exemplary embodiment of the disclosed subject matter.
Figure 10I:
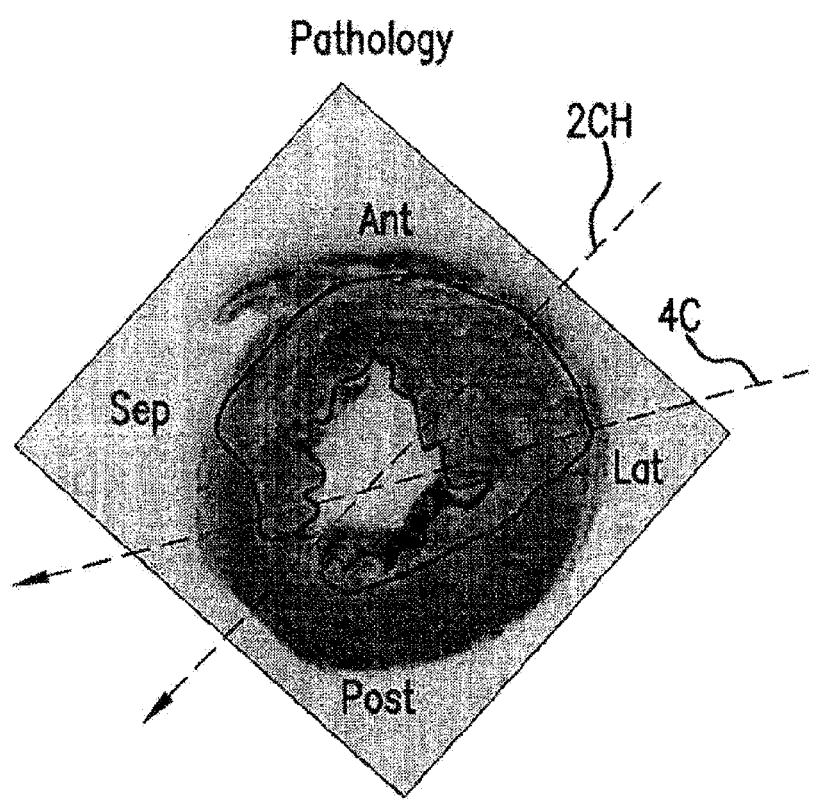
FIG. 10(i) illustrates pathological cross-section taken after reperfusion in accordance with an exemplary embodiment of the disclosed subject matter.

FIG. 10(h) illustrates the evolution of the P-V loop with the occlusion level. The presence of acute ischemia was assessed with pathology, after reperfusion, illustrated in FIG. 10(i). TTC is used to stain non-viable tissue, which generally spans a smaller region than the ischemic tissue. Reperfusion accentuates the size of this non-viable region. The slice shown in FIG. 10(i) is approximately at 3 cm from the apex.

FIG. 11(a)1-FIG. 11(c)3 illustrate a bi-plane (two-chamber+four-chamber) view of the same heart under different LAD coronary artery occlusion levels: normal (FIG. 11(a)), 60% occlusion (FIG. 11(b)) and 100% occlusion (FIG. 11(c)). The ischemia is visible in the anterior, posterior and lateral wall near the apex at 60% occlusion (light circles in FIG. 11(b)) and in the anterior, posterior, lateral, and septal wall at 100% occlusion (light circles in FIG. 11(c)). In the ischemic cases, the wave was initiated as in the normal case, but its propagation was impeded at the mid-apical level. After EMW propagation, a region that did not undergo thickening could be identified, which indicated an inability of the tissue to contract. The location of the ischemic region is consistent with the pathology findings as shown in FIG. 10(i).

Figure 12A:
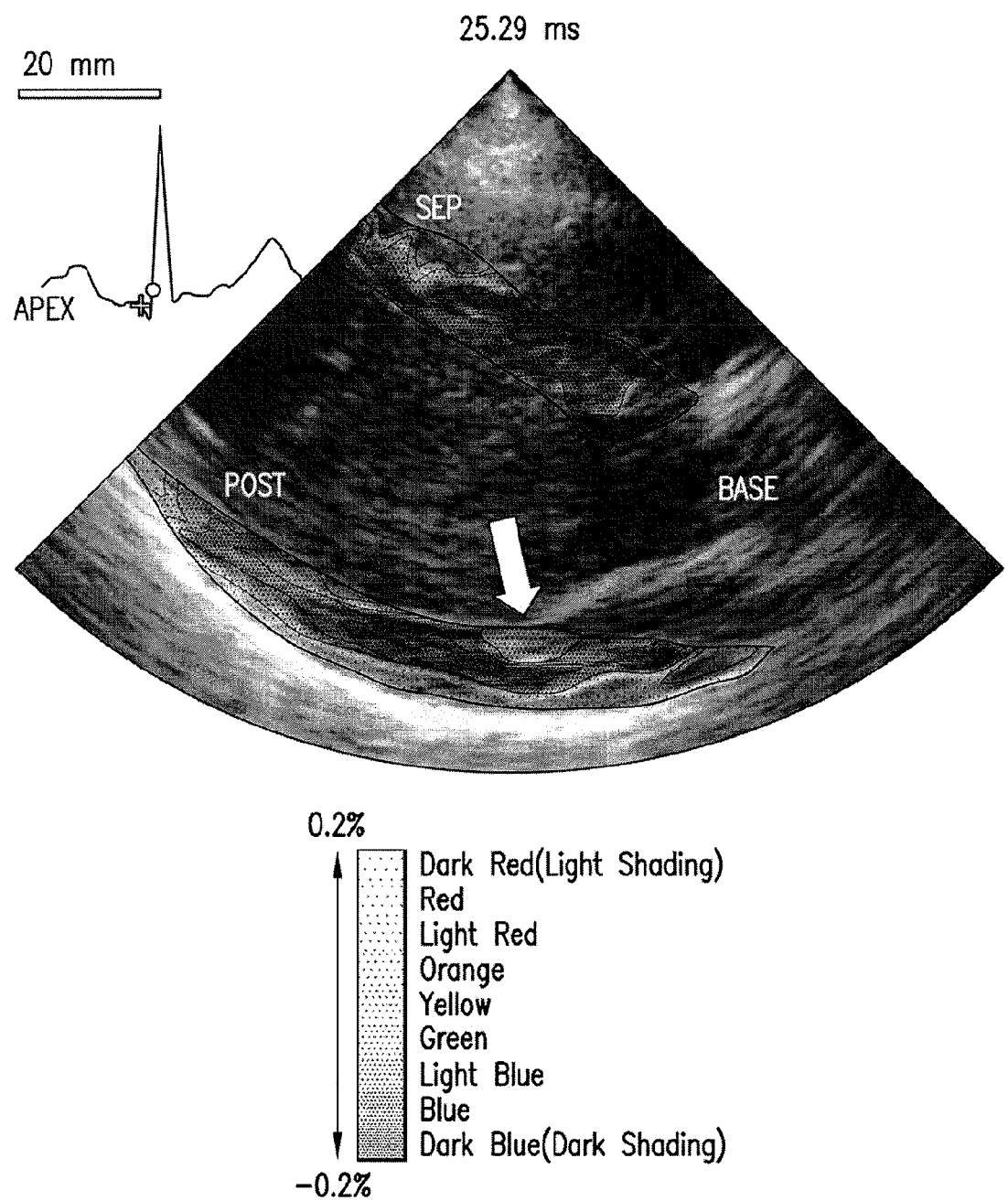
FIGS. 12(a)-(c) illustrate electromechanical strain maps in accordance with an exemplary embodiment of the disclosed subject matter.
Figure 12B:
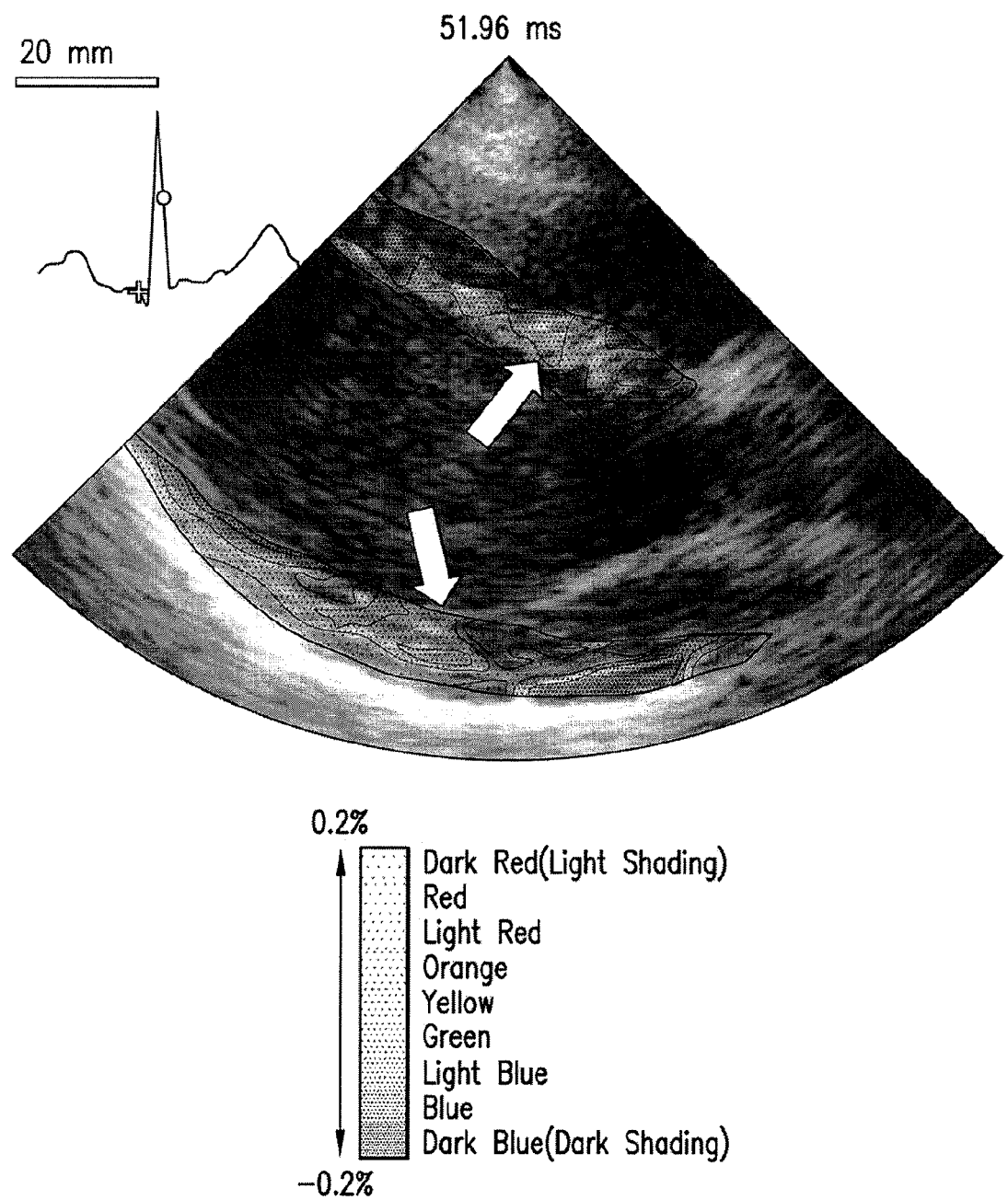
Figure 12C:
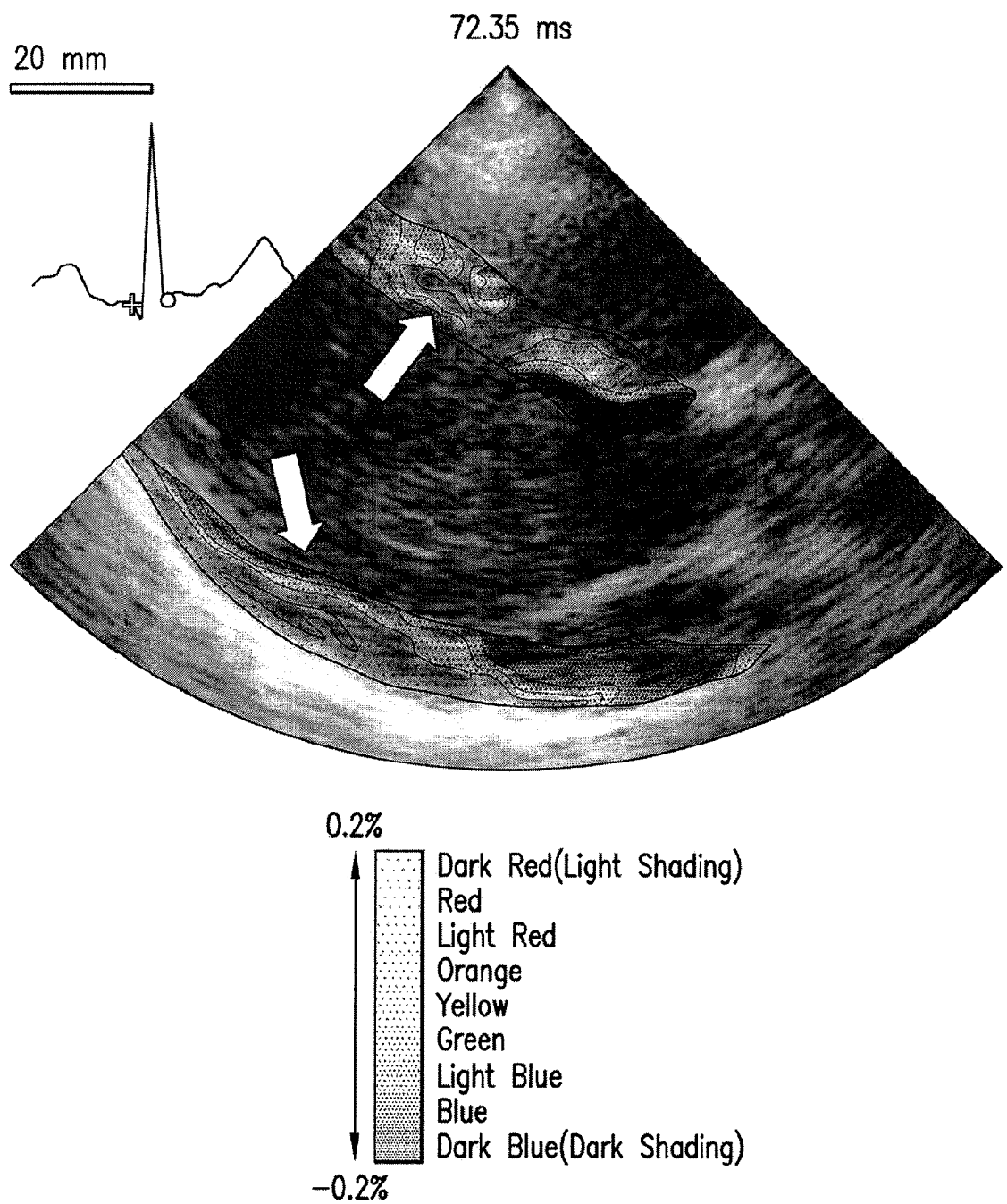

FIGS. 12(a)-(c) illustrate electromechanical strain maps at (a) 27 ms, (b) 52 ms and (c) 72 ms after the Q wave of the electrocardiogram in a healthy young human volunteer. They show two waves (arrows) propagating from base (right) to apex (left). The image frames were reconstructed from 5 sectors obtained at 390 frames per second using the motion-matching algorithm detailed above.

Figures 1, 13:
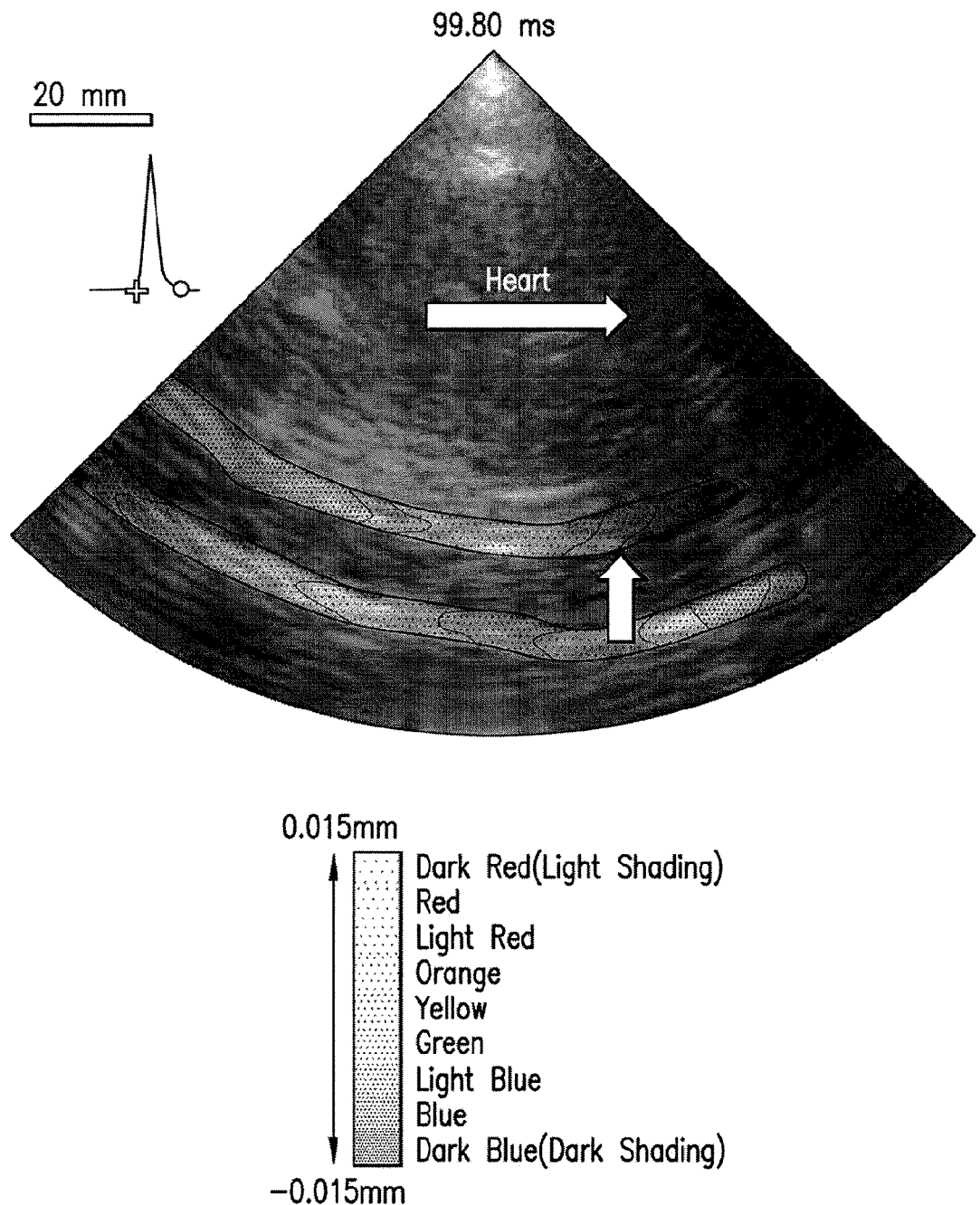
FIG. 13 illustrates an image of a pulse wave propagating through the abdominal aorta of a healthy human volunteer in accordance with an exemplary embodiment of the disclosed subject matter.
Figures 2, 13:
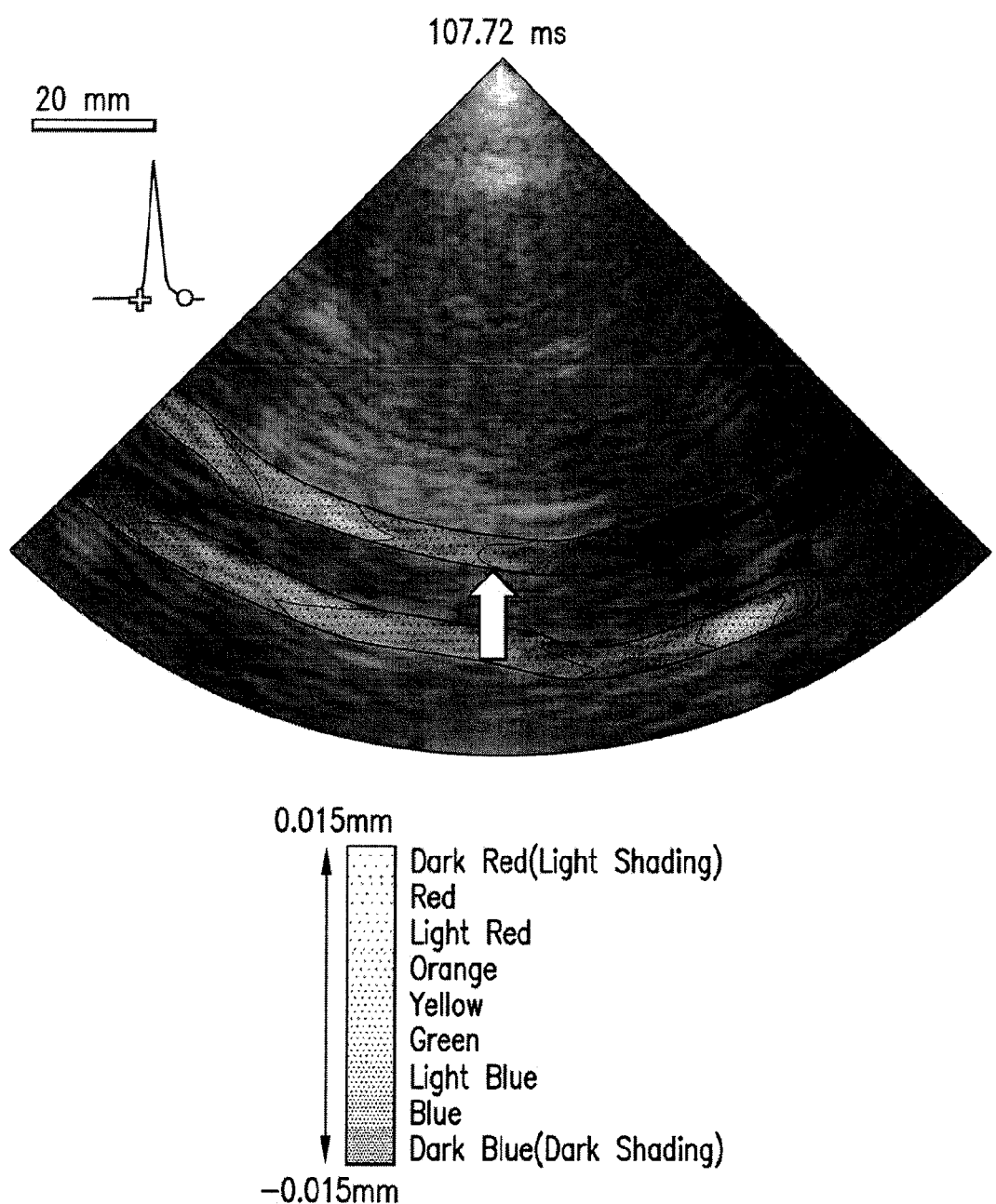
Figures 3, 13:
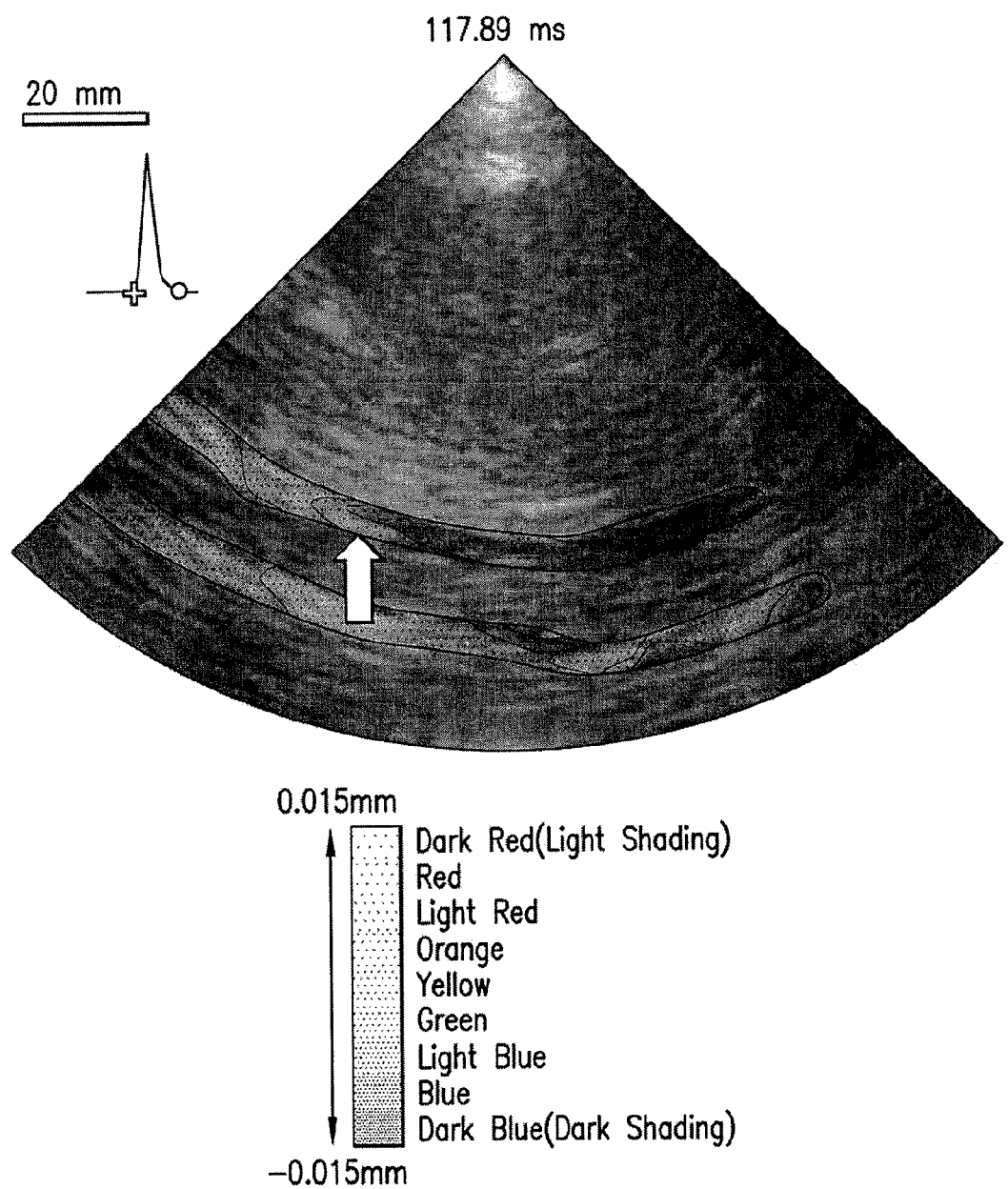

FIG. 13 illustrates an image of a pulse wave propagating through the abdominal aorta of a healthy human volunteer. The arrows indicate the propagation of the pulse wave, which is an indicator of the aorta's stiffness. The image frames were reconstructed from seven sectors acquired at 492 frames per second. The time indicated on each frame is measured from the onset of the QRS complex of the electrocardiogram. Light and dark shading indicate upward and downward motion, respectively.

FIG. 14(a)1-FIG. 14(b)3 illustrate electromechanical wave imaging of a patient undergoing cardiac resynchronization therapy with two different pacing schemes: FIG. 14(a) illustrates atrial and bi-ventricular pacing and FIG. 14(b) illustrates atrial and left-ventricular pacing. The image frames were reconstructed from five sectors acquired at 300 frames per second with the motion-matching algorithm and allow the detection of different wave propagation patterns (arrows) with different pacing schemes. The time indicated on each frame is measured from the onset of the QRS complex of the electrocardiogram. Light and dark shading indicate upward and downward motion, respectively.

Figure 15:
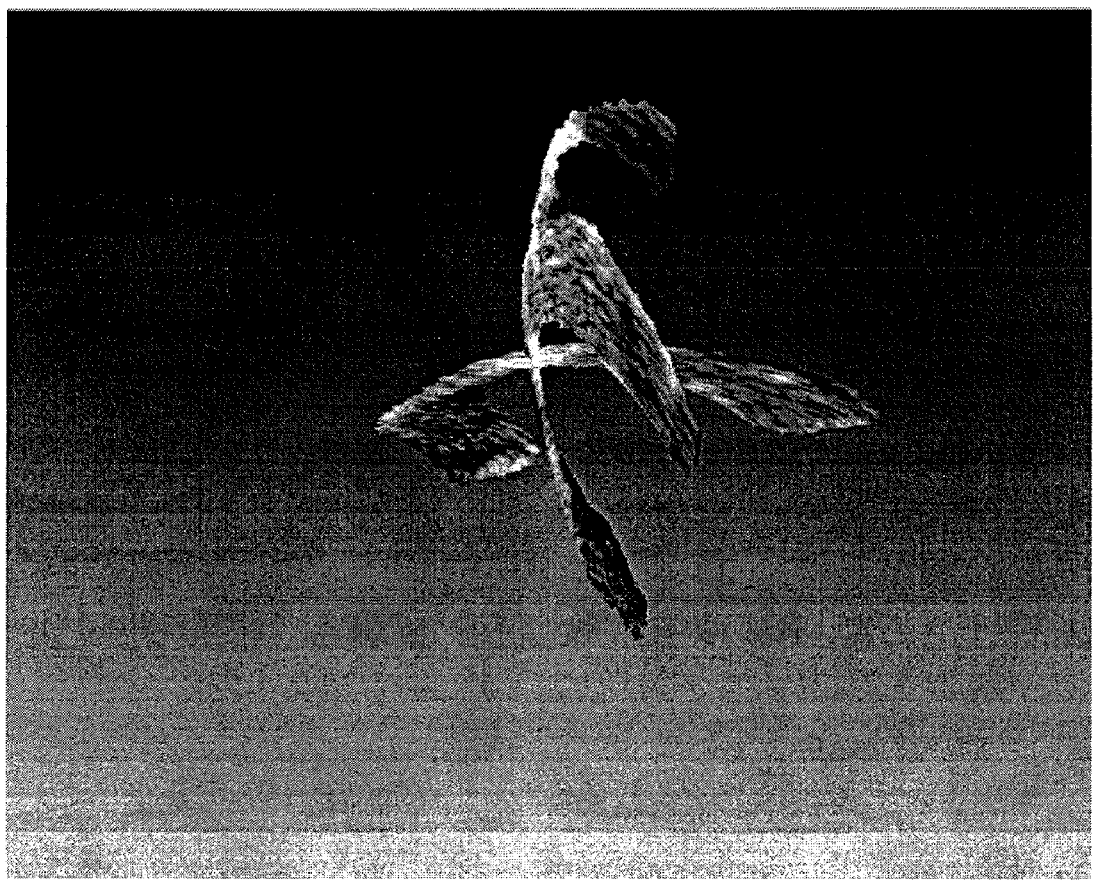
FIG. 15 illustrates a 3D electromechanical strain image in accordance with an exemplary embodiment of the disclosed subject matter.

FIG. 15 illustrates a 3D electromechanical strain image generated 250 in accordance with the above-described techniques.

In accordance with the principles of the disclosed subject matter a second experiment was conducted, with the approval of the Institutional Animal Care and Use Committee at Columbia University, on three mongrel dogs of either sex, ranging from 23 to 32 kg in weight. The dogs were prepared as detailed above with respect to the first experiment. In this experiment the dogs' hearts were imaged while the hearts were subject to various pacing schemes. Up-to twelve sonomicrometry crystals with a 2-mm diameter combined with bipolar electrodes were implanted in the ventricles. For endocardial and mid-wall crystals, an 18 G (18 gauge) needle was used for insertion. All crystals were maintained in position after placement using silk sutures. Pacing and electrophysiology measurements were performed using the crystals. Recording electrodes were located in the mid-wall along the two-chamber view and pacing electrodes were located on the epicardium along the four-chamber view. Ultrasound measurements were taken in accordance with the techniques detailed above.

FIGS. 16(a)-(e) illustrate the propagation of the electromechanical wave from a pacing lead location in the basal region of the lateral wall (as illustrated by the star in FIG. 16(a)). The white arrows in FIGS. 16(a)-(e) indicate the propagation direction of the electromechanical wave. FIG. 16(f) illustrates the activation of the electrocardiogram as the electromechanical wave propagates, with each of the time periods of FIGS. 16(a)-(e) indicated.

FIGS. 17(a)-(d) illustrate isochronal maps of four different pacing schemes in both anterior and posterior views. In each of FIGS. 17(a)-(d) the pacing lead location is indicated with a star. These isochronal maps were obtained by defining the onset of the electromechanical wave as the first time-point following the Q-wave, at which the temporal strain profile crosses zero. In FIGS. 17(a), (b) and (d) a unique origin of the electromechanical wave, e.g., the region with the shortest zero-crossing time, can be identified and that region coincides with the position of the pacing lead. In FIG. 17(c), when the pacing from the apical region of the antero-lateral wall, the pacing lead was located in the apical region between the two planes. As illustrated in FIGS. 17(a)-(d), the disclosed subject matter can be used to determine the propagation of the electromechanical wave from the location of a pacing lead.

FIG. 17(e) illustrates an isochronal map in both anterior and posterior views during sinus rhythm. As illustrated in FIG. 17(e), during sinus rhythm complex activation patterns result since activation originates from multiple locations following the Purkinje fiber network.

FIG. 18 illustrates the electromechanical wave onset time versus the time of electrical activation for five different pacing schemes corresponding to those illustrated in FIGS. 17(a)-(e). The pacing schemes are: Sinus Rhythm (FIG. 17(e)), left ventricle apical region (LVar; FIG. 17(c)), left ventricle base (LVb; FIG. 17(a)), right ventricle apex (RVa; FIG. 17(d)), and left ventricle apex (LVa; FIG. 17(b)). The electrical activation data was obtained using four recording electrodes placed in the two-chamber view plane for that purpose. As illustrated in FIG. 18, a linear relationship between the onset of the electromechnical wave and the electrical activation time was found in all four pacing schemes and during sinus rhythm. The linear relationship has a slope of 0.99±0.1 ($R^2$=0.88, $p<10^{-7}$) and an intercept of 14±7 ms (p=0.06).

Figure 19A:
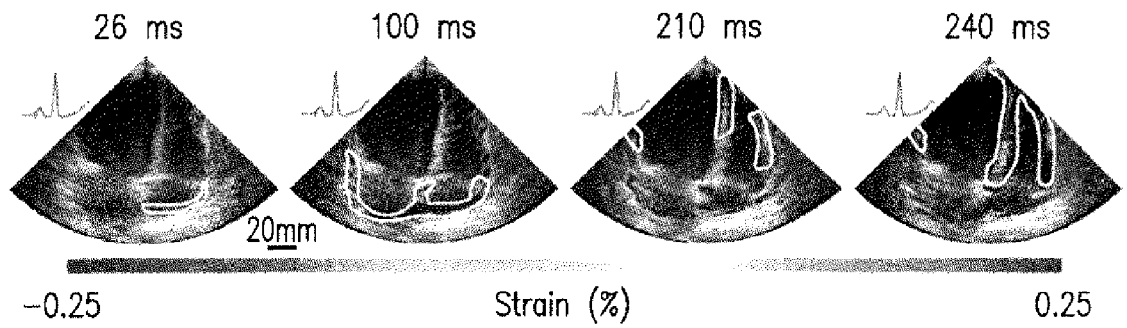
FIG. 19(*a*) illustrates the propagation of electromechanical waves in all four cardiac chambers of a healthy human subject in accordance with an exemplary embodiment of the disclosed subject matter.
Figure 19B:
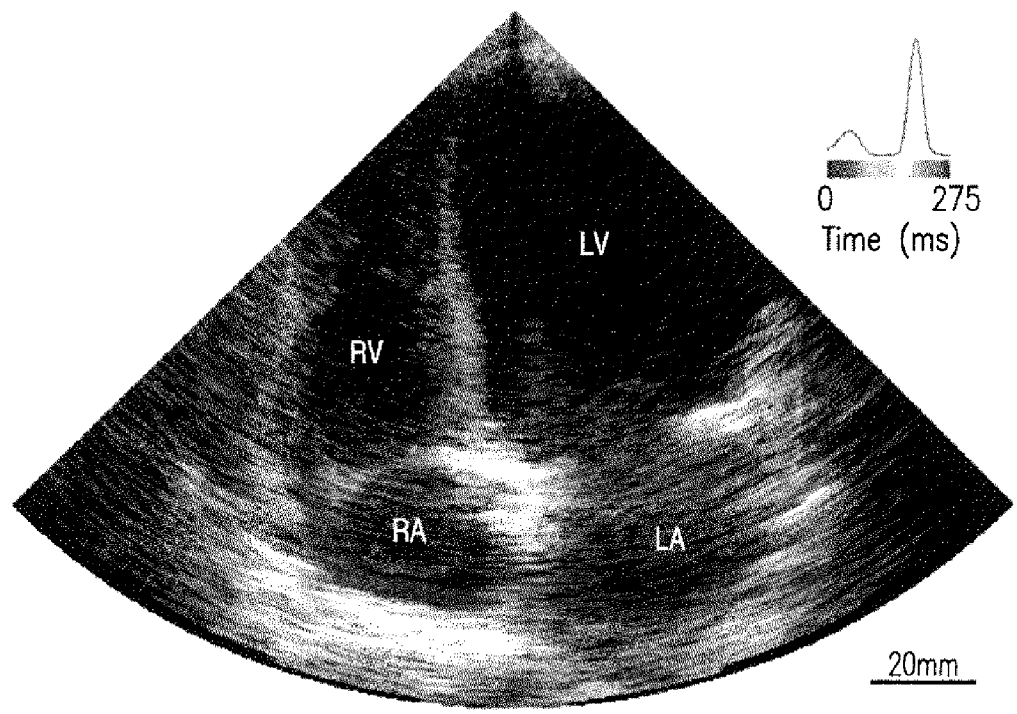

In accordance with the principles of the disclosed subject matter an experiment was conducted on two 23-year-old healthy human subjects; one male, one female. FIG. 19(a) shows the propagation of the electromechanical wave (outlined in white) in the 23-year-old female at 26.25 ms, 100.26 ms, 210.24 ms, and 240.16 ms. The time of activation in the atria of the subject was defined as the first occurrence following the onset of the P-wave at which the strains in absolute value exceeded 0.025%. Using this definition, the right atrium was activated 30-35 ms following the onset of the P-wave, and the electromechnical activation propagated toward the left atrium. As a result, immediately after the onset of the Q-wave, the ventricles were in a relaxation (or pre-stretched) state. The septum was activated first at the mid-level, and the electromechanical wave propagated towards the apex and base. FIG. 19(b) illustrates the corresponding isochronal representation of the electromechnical wave in FIG. 19(a). As illustrated in FIGS. 19(a)-(b), the propagation of the electromechanical wave can be imaged using the disclosed techniques in a human subject in vivo.

It will be understood that the foregoing is only illustrative of the principles described herein, and that various modifications can be made by those skilled in the art without departing from the scope and spirit of the disclosed subject matter. For example, the system and methods described herein are used for forming images of tissue displacements and strains. It is understood that that techniques described herein are useful for generating time sequences of tissue displacements and strains and/or other characteristics. Further, the techniques described have been performed on open-chested canines in order to validate with invasive procedures but it is understood the techniques are applicable to non-invasive measurements of cardiac activity. It is further understood that the techniques described herein are applicable to tissue measurements other than the examples given for cardiac tissue. Moreover, features of embodiments described herein can be combined and/or rearranged to create new embodiments.

We claim:

1. A method for imaging an electromechanical wave propagation through a tissue, comprising:
    acquiring tissue data for at least a first sector and a second sector of said tissue, said electromechanical wave propagating through said first and second sectors of said tissue;
    estimating a characteristic of at least a portion of said first sector and a characteristic of at least a portion of said second sector from said acquired tissue data;
    matching said estimated characteristic of said portion of said first sector with said estimated characteristic of said portion of said second sector;
    determining a time delay between said matched characteristic of said portion of said first sector and said matched characteristic of said portion of said second sector; and
    forming an image of said electromechanical wave propagating through said portion of said first sector and said portion of said second sector utilizing said determined time delay.

2. The method of claim 1, wherein said characteristic comprises a displacement.

3. The method of claim 1, wherein said characteristic comprises a strain.

4. The method of claim 1, wherein said characteristic comprises velocity.

5. The method of claim 1, wherein said characteristic comprises a strain rate.

6. The method of claim 1, wherein said characteristic comprises a stiffness.

7. The method of claim 2, wherein said displacement comprises axial displacement.

8. The method of claim 2, wherein said displacement comprises lateral displacement.

9. The method of claim 1, wherein forming said image comprises forming a one-dimensional image of said electromechanical wave propagating through said tissue.

10. The method of claim 1, wherein estimating said characteristic further comprises using a speckle-tracking technique.

11. The method of claim 1, further comprising:
    acquiring electrical activity data from said moving tissue; and
    determining a correspondence between said electrical activity and said estimated characteristic of said portion of said first sector and said estimated characteristic of said portion of said second sector.

12. A system for imaging an electromechanical wave propagation through a tissue, comprising:
    a non-transitory computer readable medium storing program instructions; and
    a processor adapted to receive tissue data for at least a first sector and a second sector of said tissue, said electromechanical wave propagating through said first and second sectors of said tissue,
    wherein said processor is operatively connected to said non-transitory computer readable medium and configured to execute said stored program instructions,
    wherein said processor is further configured such that upon execution of said stored program instructions, said processor:
    estimates a characteristic of at least a portion of said first sector and a characteristic of at least a portion of said second sector from said acquired tissue data, matches said estimated characteristic of said portion of said first sector with said estimated characteristic of said portion of said second sector;

determining a time delay between said matched characteristic of said portion of said first sector and said matched characteristic of said portion of said second sector; and forming an image of said electromechanical wave propagating through said portion of said first sector and said portion of said second sector utilizing said determined time delay.

13. The system of claim 12, further comprising a data acquisition device for acquiring data from two or more sectors of said tissue.

14. The system of claim 13, wherein said data acquisition device comprises an ultrasound device, an MRI device, or a CT device.

15. The system of claim 12, further comprising an electrical detection device configured to detect an electrical signal propagating through said tissue.

16. The method of claim 1, wherein forming said image comprises forming a two-dimensional image, a three-dimensional image, or a four-dimensional image of said electromechanical wave propagating through said tissue.

\* \* \* \* \*